United States Patent
Guzzo et al.

(10) Patent No.: US 8,101,632 B2
(45) Date of Patent: Jan. 24, 2012

(54) 5-FUROPYRIDINONE SUBSTITUTED INDAZOLES

(75) Inventors: Peter Robert Guzzo, Niskayuna, NY (US); Matthew David Surman, Albany, NY (US)

(73) Assignee: Albany Molecular Research, Inc., Albany, NY (US)

( * ) Notice: Subject to any disclaimer, the term of this patent is extended or adjusted under 35 U.S.C. 154(b) by 336 days.

(21) Appl. No.: 12/522,709

(22) PCT Filed: Jan. 9, 2008

(86) PCT No.: PCT/US2008/050609
§ 371 (c)(1),
(2), (4) Date: Aug. 19, 2009

(87) PCT Pub. No.: WO2008/086409
PCT Pub. Date: Jul. 17, 2008

(65) Prior Publication Data
US 2009/0318439 A1    Dec. 24, 2009

Related U.S. Application Data

(60) Provisional application No. 60/884,351, filed on Jan. 10, 2007, provisional application No. 60/951,202, filed on Jul. 21, 2007.

(51) Int. Cl.
*A61K 31/4355* (2006.01)
*C07D 491/048* (2006.01)

(52) U.S. Cl. ........................................ 514/302; 546/115

(58) Field of Classification Search .................. 546/115; 514/302
See application file for complete search history.

(56) References Cited

FOREIGN PATENT DOCUMENTS

| EP | 0 329 168 A2 | 8/1989 |
| EP | 1 741 703 A1 | 1/2007 |
| WO | 03/068230 A1 | 8/2003 |
| WO | 2005/085200 A1 | 9/2005 |

OTHER PUBLICATIONS

International Search Report for International Patent Application PCT/US2008/050609 (Jun. 11, 2008).
Written Opinion of the International Searching Authority for International Patent Application PCT/US2008/050609 (Jun. 11, 2008).
International Preliminary Report on Patentability for International Patent Application PCT/US2008/050609 (Jul. 14, 2009).

*Primary Examiner* — Rebecca Anderson
(74) *Attorney, Agent, or Firm* — LeClairRyan, a professional Corporation

(57) ABSTRACT

Compounds are disclosed. The compounds act as MCH1 modulators. Other embodiments are also disclosed.

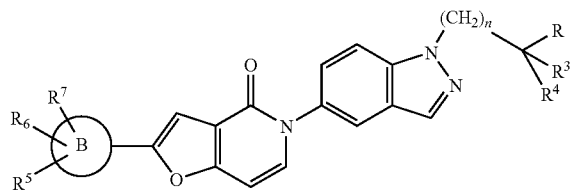

24 Claims, No Drawings

5-FUROPYRIDINONE SUBSTITUTED INDAZOLES

RELATED APPLICATIONS

This application is a U.S. national stage filing under 35 U.S.C. 371 of PCT International Patent Application No. PCT/US2008/050609, filed Jan. 9, 2008, which claims priority from U.S. provisional application No. 60/884,351, filed Jan. 10, 2007, and from U.S. provisional application No. 60/951,202, filed Jul. 21, 2007. The contents of all of the applications are incorporated herein by reference.

FIELD OF THE INVENTION

The invention relates to human melanin-concentrating hormone ($MCH_1$) receptor-selective antagonist 5-furopyridinone substituted indazoles that are useful for treating obesity, to pharmaceutical compositions comprising these compounds, and to methods for the treatment of obesity, anxiety, depression, and psychiatric disorders in a mammal.

BACKGROUND OF THE INVENTION

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, A. Chronic infusion of MCH causes obesity in mice Am. J. Physiol. Endocrinol. Metab. 284, E583, 2002) Mice lacking MCH are hypophagic and lean with increased metabolic rate, whereas animals over-expressing MCH gain excess weight on both standard and high fat diets. MCH is thought to have effects on other nervous system functions as well (Rocksz, L. L. Biological Examination of Melanin Concentrating Hormone 1: Multi-tasking from the hypothalamus Drug News Perspect 19(5), 273, 2006). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, M. D. Recent advances in the discovery of melanin-concentrating hormone receptor antagonists Curr. Opin. Drug Disc. & Dev. 9(4), 496, 2006).

SUMMARY OF THE INVENTION

There is provided, in accordance with an embodiment of the invention, a compound of formula I:

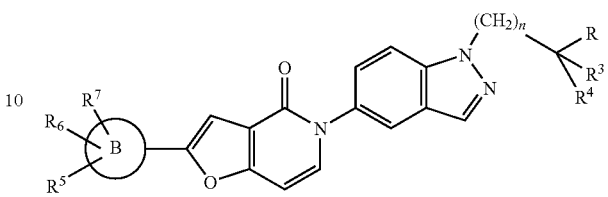

wherein
n is 1 or 2;
R is $NR^1R^2$, wherein $R^1$ and $R^2$ are each independently selected from H and optionally substituted alkyl, or $R^1$ and $R^2$, together with the N atom to which they are attached, form a 4-7 membered optionally substituted non-aromatic heterocyclic ring which optionally contains 1 or 2 heteroatoms in addition to the N atom shown;
$R^3$ and $R^4$ are each independently selected from H and alkyl, or R, $R^3$ and $R^4$ may combine to form an optionally substituted imidazolin-2-yl,
B is aryl or heteroaryl; and
$R^5$, $R^6$, $R^7$ are each independently selected from H, —OH, —O-alkyl, alkyl, halo, —$CF_3$, and —CN;
provided that the compound is not one of the following:

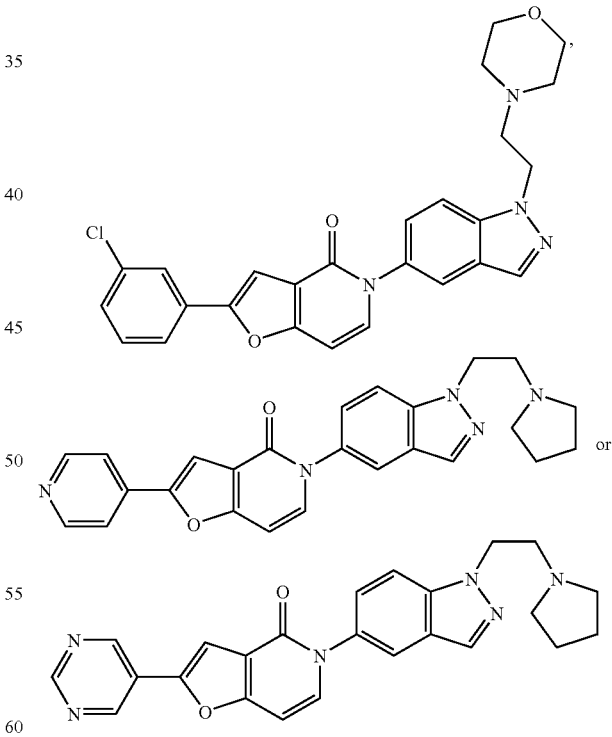

In accordance with some embodiments of the invention, R is selected from the group consisting of pyrrolidin-1-yl, morpholin-4-yl, piperazin-1-yl, 2-hydroxymethylpyrrolidin-1-yl, and 3-hydroxy-pyrrolidin-1-yl. In some embodiments, R is selected from S-2-hydroxymethylpyrrolidin-1-yl, R-2-hydroxymethylpyrrolidin-1-yl, S-3-hydroxypyrrolidin-1-yl and R-3-hydroxypyrrolidin-1-yl. In some embodiments, R, $R^3$ and $R^4$ combine to form imidazolin-2-yl which is optionally independently substituted at each of the 1-, 4- and 5-positions with alkyl. In accordance with some embodiments of the invention, $R^3$ and $R^4$ are both H. In some embodiments, n is 1. In other embodiments, n is 2.

In some embodiments of the invention, B is phenyl. In some embodiments, B, taken together with $R^5$, $R^6$ and $R^7$, is selected from the group consisting of phenyl, 4-chlorophenyl, 4-fluorophenyl, 3-chlorophenyl, 2-chlorophenyl, 4-trifluoromethylphenyl, 2-cyano-4-fluorophenyl, 2,4-dichlorophenyl, 4-chloro-2-fluorophenyl, 2-chloro-4-fluorophenyl, 4-chloro-2-methoxyphenyl, 2-fluorophenyl, 2,4-difluorophenyl, 2-fluoro-4-methylphenyl and 4-methylphenyl, In some embodiments of the invention, B is pyridine. In some embodiments, B, taken together with $R^5$, $R^6$ and $R^7$, is selected from the group consisting of 5-chloropyridin-2-yl, pyridin-3-yl, 5-fluoropyridin-2-yl, and pyridin-2-yl. In some embodiments of the invention, B is pyridazine. In some embodiments, B, taken together with $R^5$, $R^6$ and $R^7$, is 6-methylpyridazine-3-yl. In some embodiments of the invention, B is pyrimidine. In some embodiments, B, taken together with $R^5$, $R^6$ and $R^7$, is pyrimidin-2-yl.

In some embodiments of the invention, $R^5$, $R^6$, $R^7$ are each independently selected from H, —O-alkyl, alkyl, halo, —$CF_3$, and —CN.

In some embodiments of the invention, the compound is selected from one of the following:

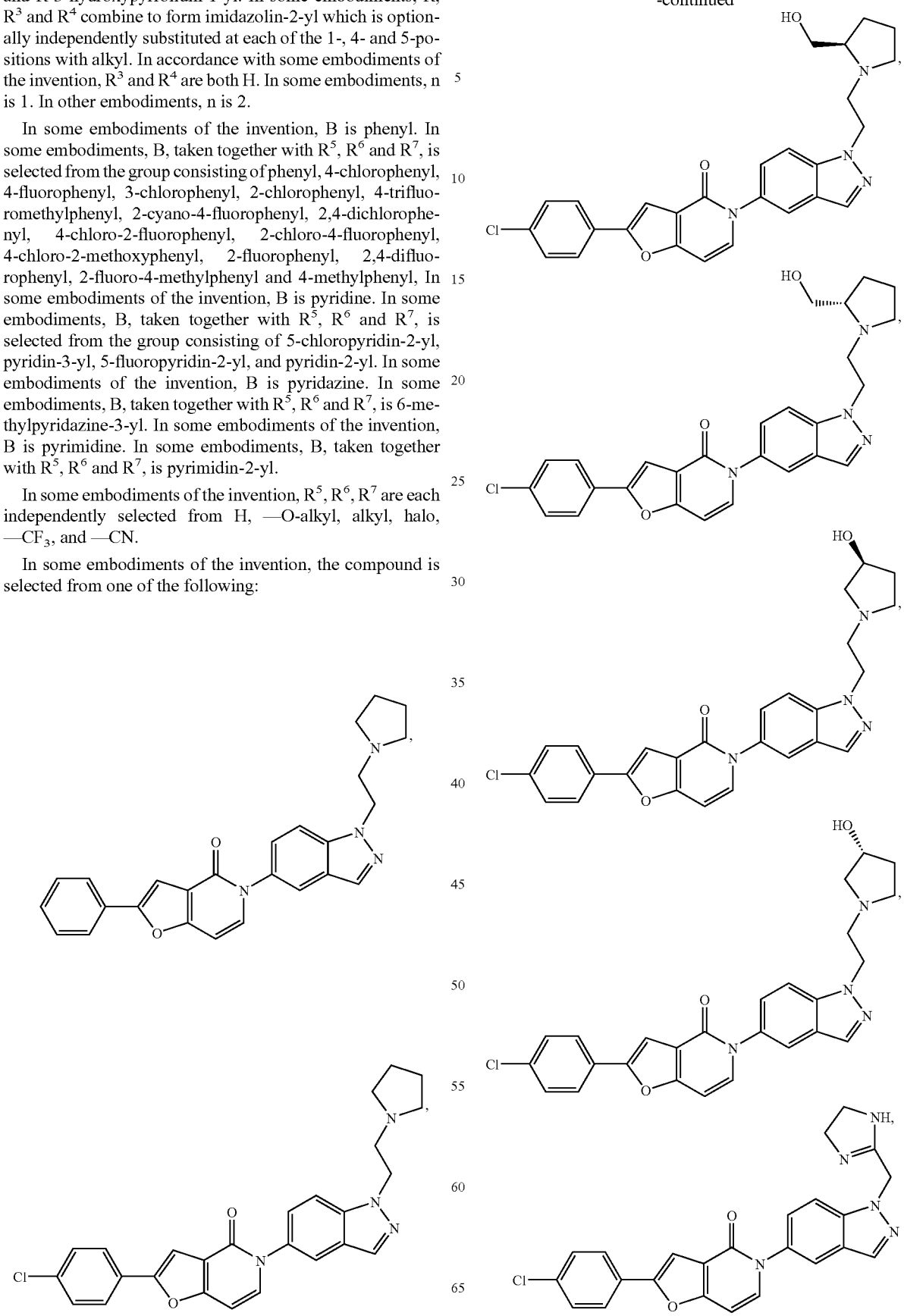

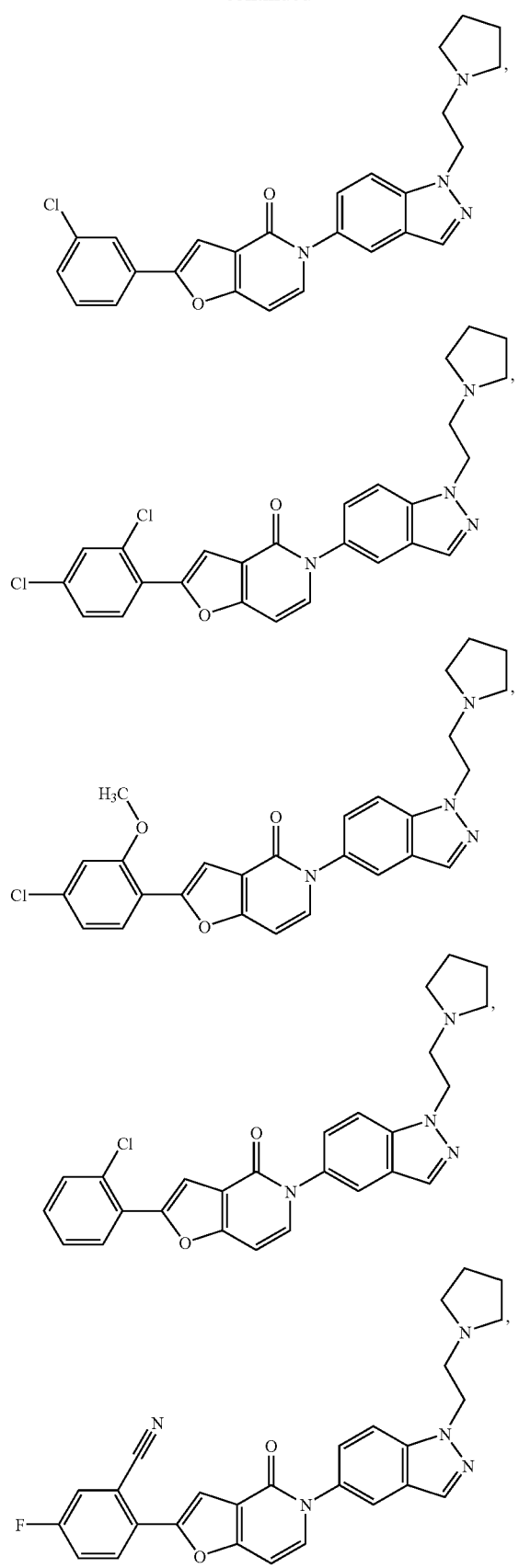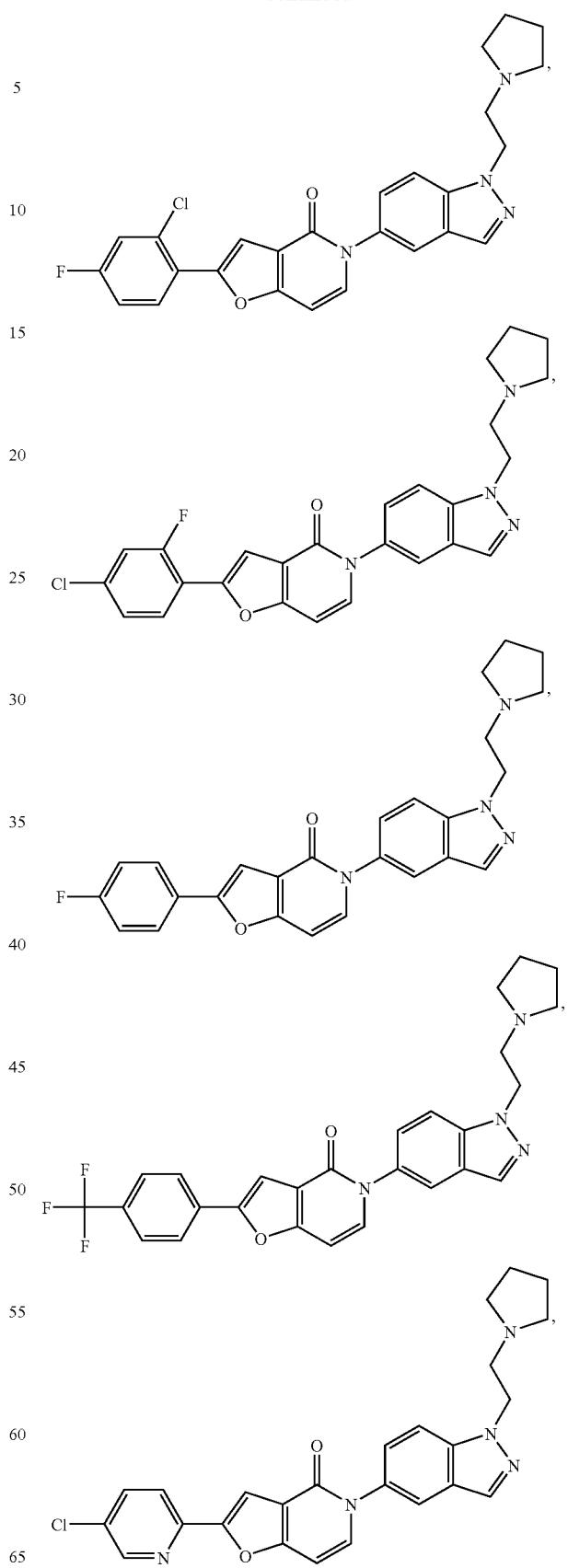

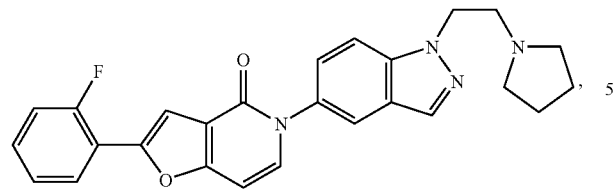

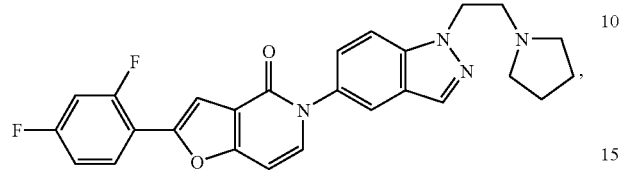

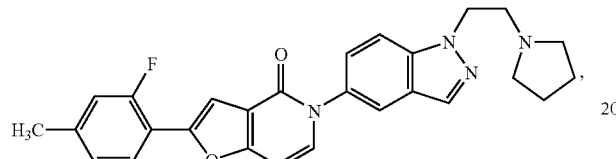

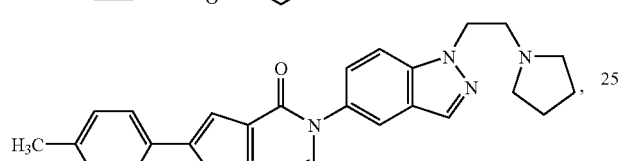

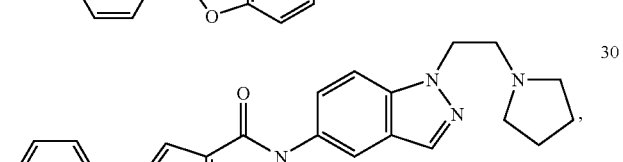

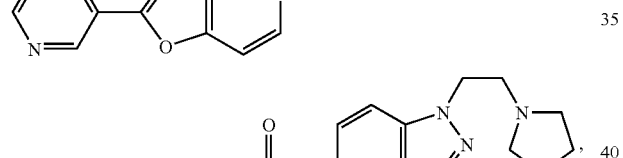

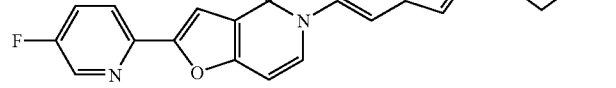

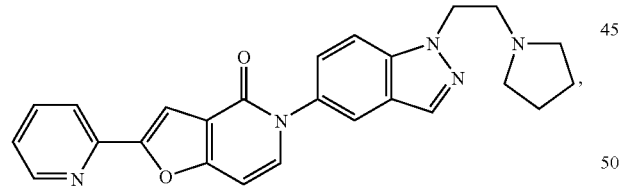

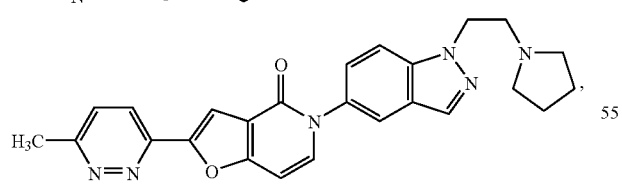

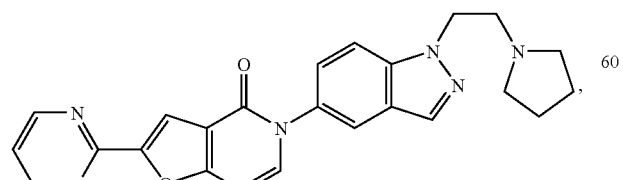

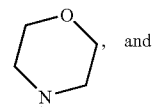, and

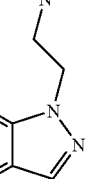

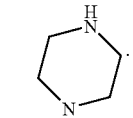.

In some embodiments of the invention, the compound is in pharmaceutically acceptable salt form. In some embodiments, the compound is the HCl salt form.

There is also provided, in accordance with embodiments of the invention, a pharmaceutical composition comprising a compound as described herein, and a pharmaceutically acceptable carrier, excipient or diluent therefore.

There is also provided, in accordance with embodiments of the invention, a method of treating obesity, comprising administering to a patient in need of obesity reduction an obesity-reducing effective amount of a compound as described herein.

There is also provided, in accordance with embodiments of the invention, a method of treating anxiety, comprising administering to a patient in need of such treatment a therapeutically effective amount of a compound as described herein.

There is also provided, in accordance with embodiments of the invention, a method of treating depression, comprising administering to a patient in need of such treatment a therapeutically effective amount of a compound as described herein.

There is also provided, in accordance with embodiments of the invention, a method of treating non-alcoholic fatty liver disease, comprising administering to a patient in need of such treatment a therapeutically effective amount of a compound as described herein.

There is also provided, in accordance with embodiments of the invention, a method of treating a disease or condition which is susceptible to treatment with an $MCH_1$ receptor modulator, comprising administering to a patient in need thereof a therapeutically effective amount of a compound as described herein.

Definitions

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

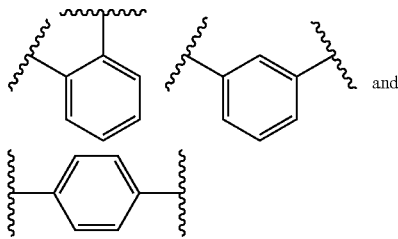

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

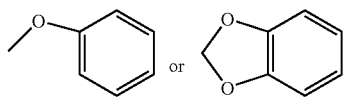

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, iodine and chlorine include $^3H$, $^{14}C$, $^{35}S$, $^{18}F$ $^{32}P$, $^{33}P$, $^{125}I$, and $^{36}Cl$, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Throughout this application, various references are referred to. Each of the patents, patent applications, patent publications, and references mentioned herein is hereby incorporated by reference in its entirety.

The term "mammal" is used in its dictionary sense. The term "mammal" includes, for example, mice, hamsters, rats, cows, sheep, pigs, goats, and horses, monkeys, dogs (e.g., Canis familiaris), cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound" is intended to include salts, solvates and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. In accordance with some embodiments of the invention, the salt is a hydrochloride salt.

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While it may be possible for compounds of formula I to be administered as the raw chemical, it will often be preferable to present them as part of a pharmaceutical composition. In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, notwithstanding the statement above regarding the term "compound" including salts thereof as well, so that independent claims reciting "a compound" will be understood as referring to salts thereof as well, if in an independent claim reference is made to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid, or as an oil-inwater liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myomositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, 20$^{th}$ Edition, 2000.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasally using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. Nos. 5,230,884, 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. Nos. 5,348,730, 6,436,367, WO 91/04011, and U.S. Pat. Nos. 6,294,153 and 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

Table 1 lists compounds representative of embodiments of the invention.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining compounds of formula I are presented below. Other compounds of formula I may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

Scheme 1

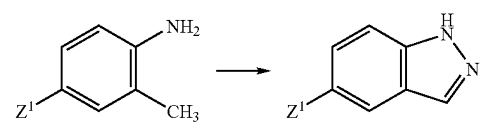

1 2

Compounds of formula 2 (wherein $Z^1$ is chlorine, bromine or iodine) can be prepared by treating compounds of formula 1 with $NaNO_2$ in acetic acid at room temperature.

Scheme 2

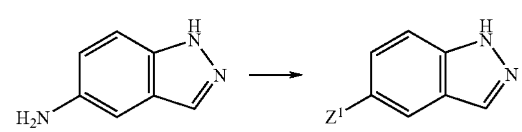

3 2

Alternatively, compounds of formula 2 can be prepared by treatment of amino indazoles 3 with $NaNO_2$ and copper halide.

Scheme 3

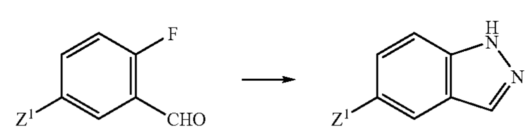

4 2

Alternatively, compounds of formula 2 can be prepared by treatment of aldehydes 4 with hydrazine under heated conditions.

Scheme 4

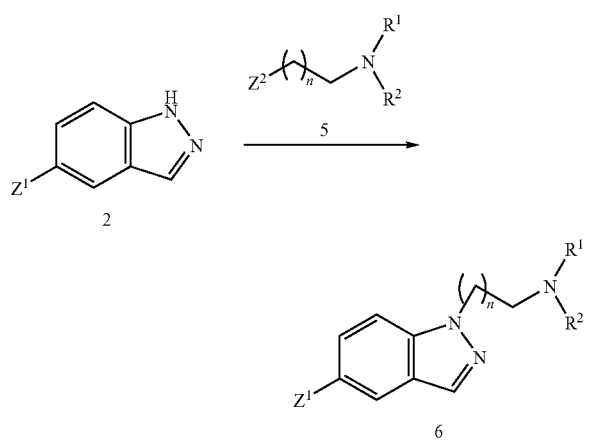

Compounds of formula 2 can be treated with base and compounds of formula 5 (wherein $Z^2$=halogen, methanesulfonate, toluenesulfonate or the like; n=1 or 2) under ambient temperature or heated conditions to give compounds of formula 6. Typical bases include but are not limited to cesium carbonate, potassium carbonate and sodium hydride. Typical solvents include but are not limited to N,N-dimethylformamide (DMF), dimethylsulfoxide (DMSO), acetonitrile and tetrahydrofuran (THF).

Scheme 5

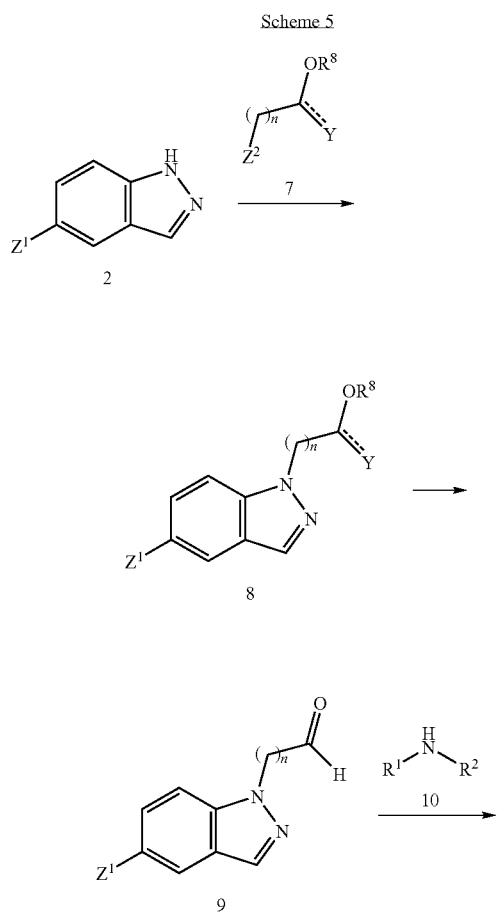

Alternatively, compounds of formula 2 can be treated with base and compounds of formula 7 (wherein $Z^2$=halogen, methanesulfonate, toluenesulfonate or the like; Y=O, $OR^9$ or H; $R^8$=an alkyl group, H or a protecting group such as tert-butyldimethylsilyl; $R^9$=alkyl; n=1 or 2) under ambient temperature or heated conditions to give compounds of formula 8. Typical bases include but are not limited to cesium carbonate, potassium carbonate and sodium hydride. Typical solvents include but are not limited to N,N-dimethylformamide, dimethylsulfoxide, acetonitrile and tetrahydrofuran. In the case where Y=$OR^9$, compounds of formula 8 can be treated under acidic reaction conditions to provide compounds of formula 9. In the case where Y=H and $R^8$=a protecting group, compounds of formula 8 can be treated under appropriate deprotecting conditions to provide compounds of formula 8, wherein $R^8$=H. In the case where Y=H and $R^8$=H, compounds of formula 8 can be treated with an oxidizing agent such as the Dess-Martin periodane or oxalyl chloride and DMSO to give compounds of formula 9. Treatment of compounds 9 with amines 10 and a reducing agent such as sodium borohydride, sodium cyanoborohydride, sodium triacetoxyborohydride, or picoline-borane complex can provide compounds of formula 11, wherein n=1 or 2.

Scheme 6

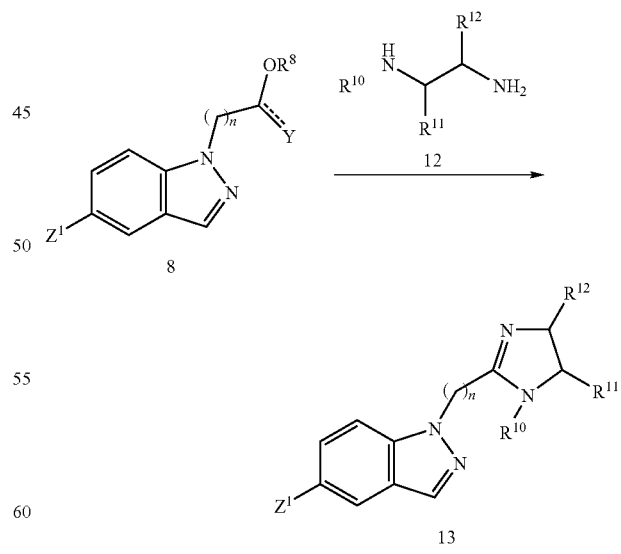

Additionally, in the case where Y=O and $R^8$=alkyl, compounds of formula 8 can be treated with diamines 12 (wherein $R^{10}$, $R^{11}$, $R^{12}$ are each independently H or alkyl) and trimethylaluminum to provide compounds of formula 13.

Scheme 7

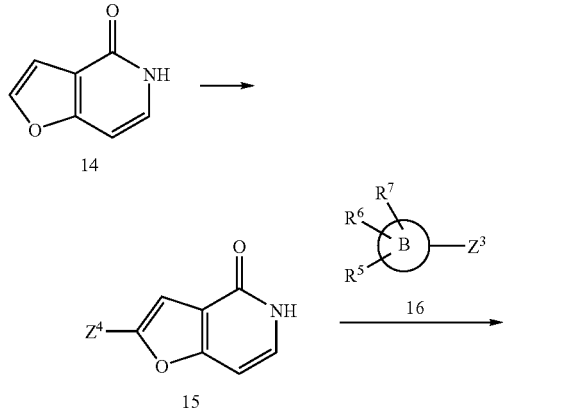

Compounds of formula 15 (wherein $Z^4$ is an activating group such as chlorine, bromine, iodine, $B(OH)_2$, $B(OR^{13})_2$, $SnR^{13}_3$ or the like and $R^{13}$=alkyl) can be prepared from furo[3,2-c]pyridin-4(5H)-one (compound 14). In the case where $Z^4$ is bromine, compound 14 can be treated with a brominating agent such as pyridinium hydrobromide perbromide in acetic acid under ambient temperature to heated conditions to give compounds of formula 15. In turn, treatment of compounds of formula 15 with compounds of formula 16 (wherein $Z^3$=chlorine, bromine, iodine, $B(OH)_2$, $B(OR^{13})_2$, $SnR^{13}_3$ or the like and $R^{13}$=alkyl), a catalyst such as palladium(0), and a base such as potassium carbonate under heated conditions can provide compounds of formula 17.

Scheme 8

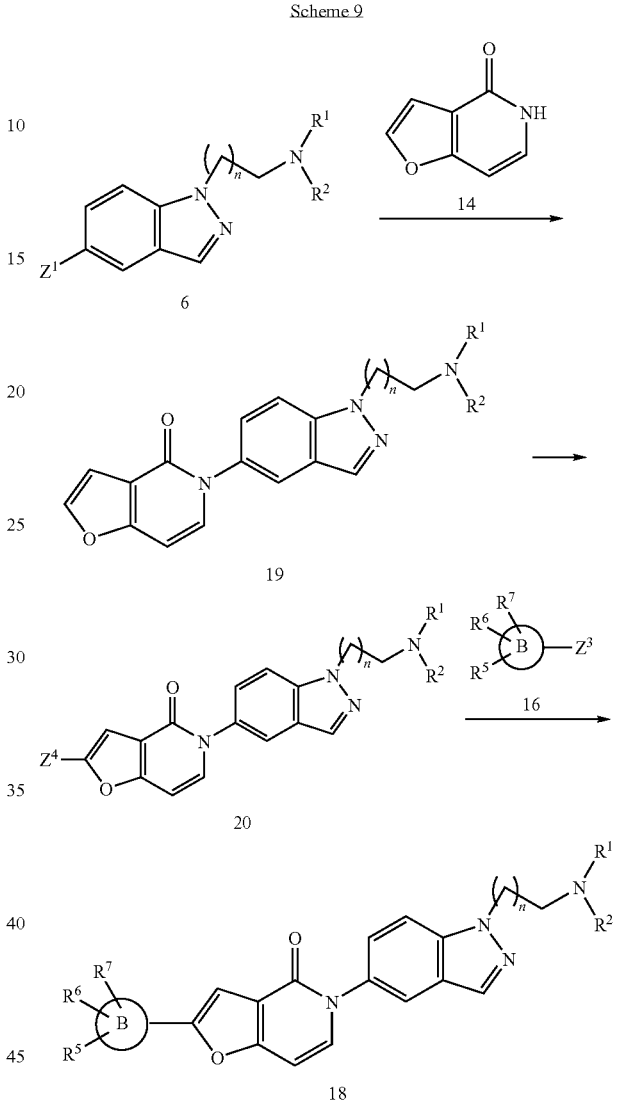

Compounds of formula 6 can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 17 to give compounds of formula 18.

Scheme 9

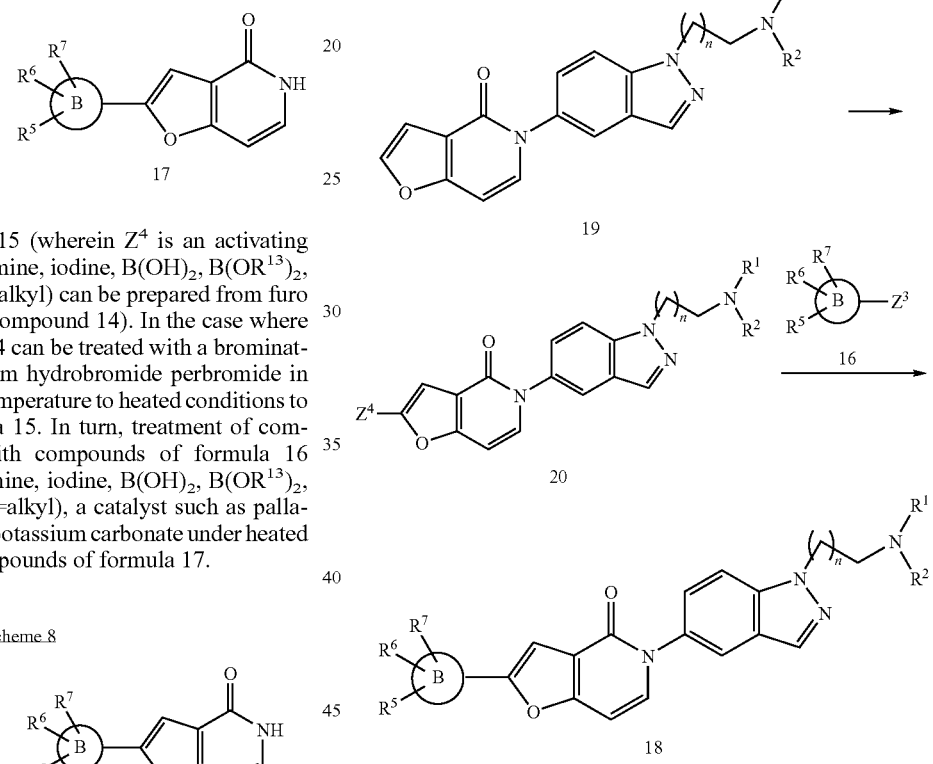

Alternatively, compounds of formula 6 can be treated under heated conditions with a catalyst such as copper iodide, a ligand such as trans-1,2-diaminocyclohexane or 8-hydroxyquinoline, a base such as potassium carbonate, cesium carbonate or potassium phosphate and furo[3,2-c]pyridin-4(5H)-one to give compounds of formula 19. In turn, an appropriate activating group can be installed on the furopyridinone ring to give compounds of formula 20 (wherein $Z^4$=chlorine, bromine, iodine, $B(OH)_2$, $B(OR^{13})_2$, $SnR^{13}_3$ or the like and $R^{13}$=alkyl). In the case where $Z^4$ is bromine, compounds of formula 19 can be treated with a brominating agent such as pyridinium hydrobromide perbromide in acetic acid under ambient temperature to heated conditions to give compounds of formula 20. Treatment of compounds of formula 20 with compounds of formula 16 (wherein $Z^3$=chlorine, bromine, iodine, $B(OH)_2$, $B(OR^{13})_2$, $SnR^{13}_3$ or the like and $R^{13}$=alkyl), a catalyst such as palladium(0), and a base such as potassium carbonate under heated conditions can provide compounds of formula 18.

Scheme 10

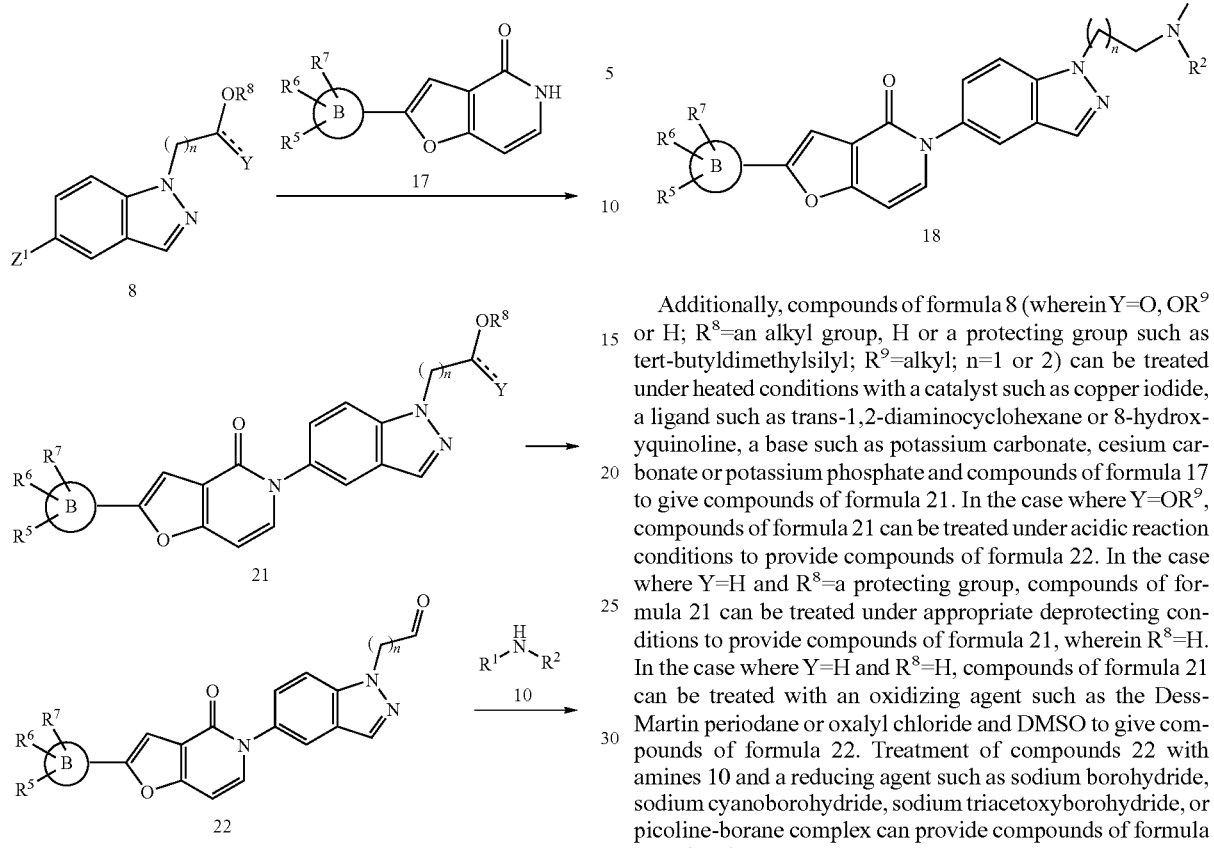

Additionally, compounds of formula 8 (wherein Y=O, OR$^9$ or H; R$^8$=an alkyl group, H or a protecting group such as tert-butyldimethylsilyl; R$^9$=alkyl; n=1 or 2) can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 17 to give compounds of formula 21. In the case where Y=OR$^9$, compounds of formula 21 can be treated under acidic reaction conditions to provide compounds of formula 22. In the case where Y=H and R$^8$=a protecting group, compounds of formula 21 can be treated under appropriate deprotecting conditions to provide compounds of formula 21, wherein R$^8$=H. In the case where Y=H and R$^8$=H, compounds of formula 21 can be treated with an oxidizing agent such as the Dess-Martin periodane or oxalyl chloride and DMSO to give compounds of formula 22. Treatment of compounds 22 with amines 10 and a reducing agent such as sodium borohydride, sodium cyanoborohydride, sodium triacetoxyborohydride, or picoline-borane complex can provide compounds of formula 18, wherein n=1 or 2.

Scheme 11

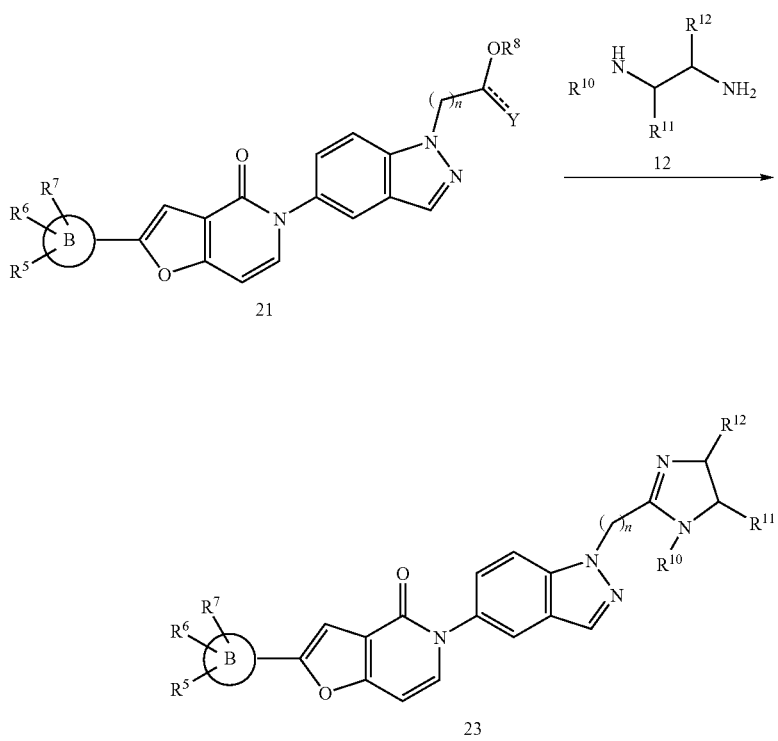

Additionally, in the case where Y=O and R⁸=alkyl, compounds of formula 21 can be treated with diamines 12 and trimethylaluminum to provide compounds of formula 23.

Scheme 12

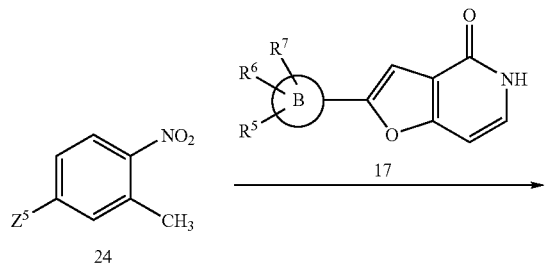

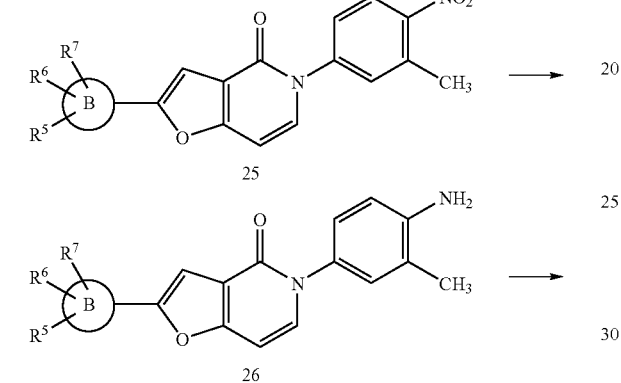

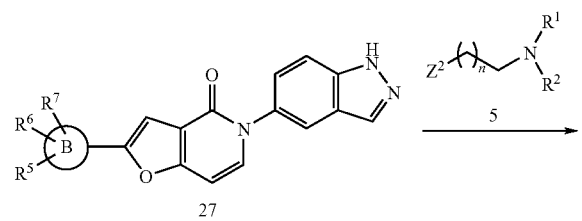

Alternatively, compounds of formula 24 (wherein Z⁵ is an activating group such as fluorine, chlorine, bromine or iodine) can be treated under heated conditions in a solvent such as DMF with a base such as sodium carbonate or cesium carbonate and compounds of formula 17 to give compounds of formula 25. In turn, compounds of formula 25 can be treated under reducing conditions such as SnCl₂, iron powder and NH₄Cl, or palladium on carbon under a hydrogen atmosphere to provide compounds of formula 26. Treatment of compounds 26 with NaNO₂ in acetic acid at room temperature can provide compounds of formula 27. Compounds 27 can be treated with a base and compounds of formula 5 (wherein Z²=halogen, methanesulfonate, toluenesulfonate or the like, n=2 or 3) under ambient temperature or heated conditions to give compounds of formula 18. Typical bases include but are not limited to cesium carbonate, potassium carbonate and sodium hydride. Typical solvents include but are not limited to N,N-dimethylformamide, dimethylsulfoxide, acetonitrile and tetrahydrofuran.

Scheme 13

Additionally, compounds of formula 27 can be treated with base and compounds of formula 7 (wherein Z²=halogen, methanesulfonate, toluenesulfonate or the like; Y=O, OR⁹ or H; R⁸=an alkyl group, H or a protecting group such as tert-butyldimethylsilyl; R⁹=alkyl; n=1 or 2) under ambient temperature or heated conditions to give compounds of formula 21. Typical bases include but are not limited to cesium carbonate, potassium carbonate and sodium hydride. Typical solvents include but are not limited to N,N-dimethylformamide, dimethylsulfoxide, acetonitrile and tetrahydrofuran.

Scheme 14

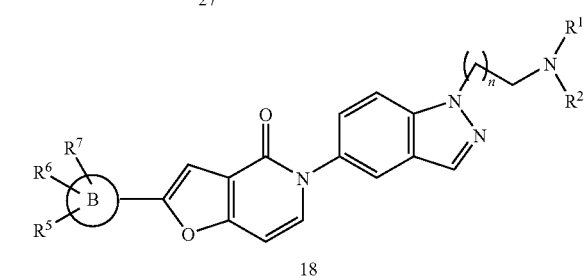

25

-continued

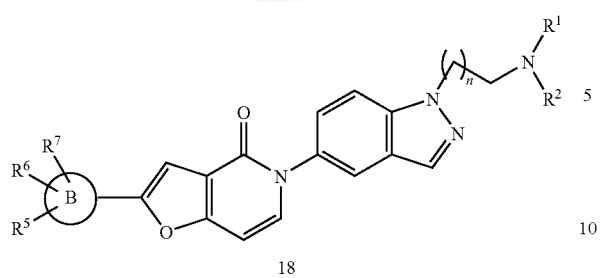

18

Alternatively, compounds of formula 27 can be treated with base and compounds of formula 28 (wherein n=1 or 2 and $Z^6$ and $Z^7$=halogen, methanesulfonate, toluenesulfonate or the like) under ambient temperature or heated conditions to give compounds of formula 29. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds of formula 29 with amines 10 under ambient temperature or heated conditions can provide compounds of formula 18 (wherein n=1 or 2).

Scheme 15

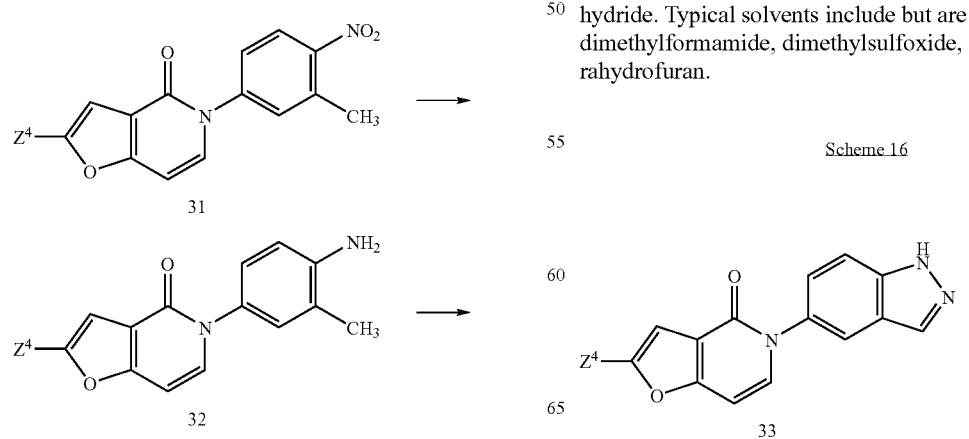

26

-continued

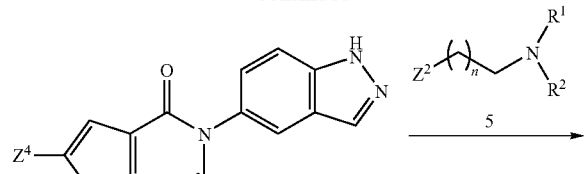

33

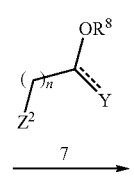

20

Alternatively, compounds of formula 20 can be made starting from compounds of formula 24. Compounds of formula 24 (wherein $Z^5$ is an activating group such as fluorine, chlorine, bromine or iodine) can be treated under heated conditions in a solvent such as DMF with a base such as sodium carbonate or cesium carbonate and furo[3,2-c]pyridin-4(5H)-one (compound 14) to give compounds of formula 30. In turn, an appropriate activating group can be installed on the furopyridinone ring to give compounds of formula 31 (wherein $Z^4$=chlorine, bromine, iodine, $B(OH)_2$, $B(OR^{13})_2$, $SnR^{13}_3$ or the like and $R^{13}$=alkyl). In the case where $Z^4$ is bromide, compounds of formula 30 can be treated with a brominating agent such as pyridinium hydrobromide perbromide in acetic acid under ambient to heated conditions to give compounds of formula 31. Compounds of formula 31 can be treated under reducing conditions such as $SnCl_2$ or iron powder and $NH_4Cl$ to provide compounds of formula 32. Treatment of compounds 32 with $NaNO_2$ in acetic acid at room temperature can provide compounds of formula 33. Compounds 33 can be treated with a base and compounds of formula 5 (wherein $Z^2$=halogen, methanesulfonate, toluenesulfonate or the like) under ambient temperature or heated conditions to give compounds of formula 20. Typical bases include but are not limited to cesium carbonate, potassium carbonate and sodium hydride. Typical solvents include but are not limited to N,N-dimethylformamide, dimethylsulfoxide, acetonitrile and tetrahydrofuran.

Scheme 16

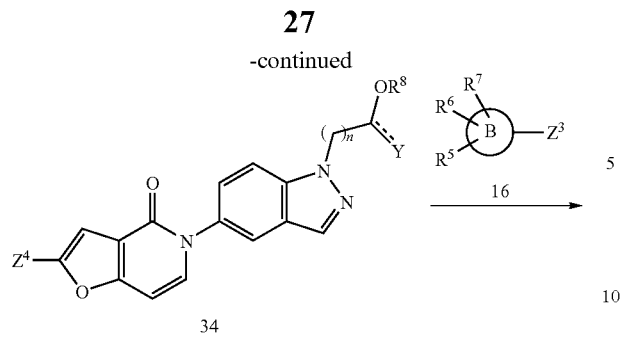

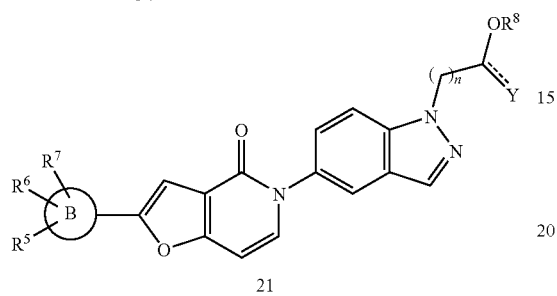

Additionally, compounds of formula 21 can be made starting from compounds of formula 33. Compounds of formula 33 can be treated with base and compounds of formula 7 (wherein $Z^2$=halogen, methanesulfonate, toluenesulfonate or the like; Y=O, $OR^9$ or H; $R^8$=an alkyl group, H or a protecting group such as tert-butyldimethylsilyl; $R^9$=alkyl; n=1 or 2) under ambient temperature or heated conditions to give compounds of formula 34. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds of formula 34 with compounds of formula 16 (wherein $Z^3$=chlorine, bromine, iodine, $B(OH)_2$, $B(OR^{13})_2$, $SnR^{13}_3$ or the like and $R^{13}$=alkyl), a catalyst such as palladium(0), and a base such as potassium carbonate under heated conditions can provide compounds of formula 21, which can be converted to compounds of formula 18 as shown above.

EXAMPLES

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS Ion trap electrospray ionization (ESI) or a mass Varian 1200L single quadrapole mass spectrometer (ESI). High performance liquid chromatograph (HPLC) analyses were obtained using a Luna C18 (2) column (250×4.6 mm, Phenomenex) with UV detection at 254 nm using a standard solvent gradient program (Method A).

Method A:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid

Example 1

Preparation of 2-Phenyl-5-(1-(2-(pyrrolidine-1-yl)ethyl)-1H-indazol-5-yl)furo[3,2-c]pyridine-4(5H)-one hydrochloride a) 2-Phenyl-5H-furo[3,2-c]pyridine-4-one Beilstein Registry number 7705392

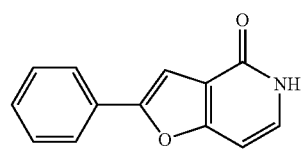

Chemical Formula: $C_{13}H_9NO_2$
Exact Mass: 211.06
Molecular Weight: 211.22

This molecule was prepared in accordance with the synthesis described in Krutosikova and Sleziak, *Collect. Czech. Chem. Commun.* 1996, 61, 1627-1636.

b) 5-Iodo-1H-indazole

Beilstein Registry Number 3262

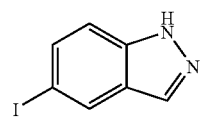

Chemical Formula: $C_7H_5IN_2$
Exact Mass: 243.95
Molecular Weight: 244.03

A solution of 4-iodo-2-methylaniline (10.0 g, 42.9 mmol) in glacial acetic acid (400 mL) was treated with a solution of $NaNO_2$ (2.96 g, 42.9 mmol) in water (10 mL). After stirring for 6 hours, the mixture was concentrated to dryness and dissolved in ethyl acetate (EtOAc). Filtration through a pad of silica gel (EtOAc) provided the title compound (10.4 g, 99%) as a deep purple solid. ESI MS m/z 245 $[M+H]^+$.

c) 5-Iodo-1-(2-(pyrrolidin-1-yl)ethyl)-1H-indazole

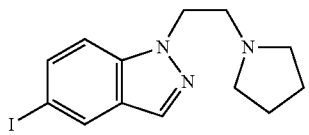

Chemical Formula: $C_{13}H_{16}IN_3$
Exact Mass: 341.04
Molecular Weight: 341.19

1-(2-Chloroethyl)pyrrolidine hydrochloride (9.88 g, 58.1 mmol) was added to a suspension of 5-iodo-1H-indazole (8.86 g, 36.3 mmol) and $Cs_2CO_3$ (50.8 g, 456 mmol) in anhydrous DMSO (100 mL) and the resulting suspension was stirred at 25° C. for 14 h. $H_2O$ (100 mL) was added and the aqueous solution was extracted with EtOAc (3×200 mL). The combined organic extracts were washed with brine (2×200 mL), dried over $MgSO_4$ and concentrated under reduced pressure. Flash chromatography on silica gel (9:1 $Et_2O/Et_3N$) afforded 6.473 g (52%) of the title compound as a yellow solid: $^1H$ NMR (300 MHz, $CDCl_3$) δ 8.08 (br d, J=13 Hz, 1H), 7.91 (d, J=0.9 Hz, 1H), 7.60 (dd, J=87, 1.3 Hz, 1H), 7.25 (d, J=8.7 Hz, 1H), 4.50 (t, J=7.4 Hz, 2H), 2.98 (t, J=7.4 Hz, 2H), 2.59-2.50 (m, 4H), 1.82-1.70 (m, 4H).

d) 2-Phenyl-5-(1-(2-(pyrrolidine-1-yl)ethyl)-1H-indazol-5-yl)furo[3,2-c]pyridine-4(5H)-one

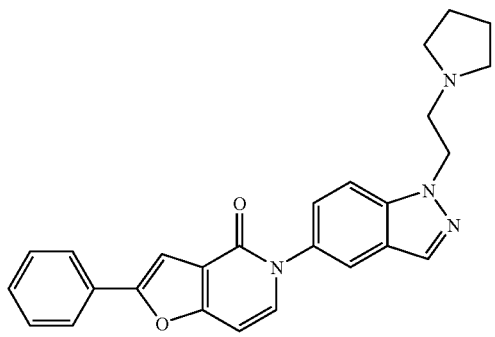

Chemical Formula: $C_{26}H_{24}N_4O_2$
Exact Mass: 424.19
Molecular Weight: 424.49

A solution of 5-iodo-1-(2-(pyrrolidin-1-yl)ethyl)-1H-indazole (0.316 g, 0.923 mmol) in N-methylpyrrolidone (NMP) (2.7 mL) was added to 2-phenyl-5H-furo[3,2-c]pyridine-4-one (0.232 g, 1.10 mmol), $Cs_2CO_3$ (0.601 g, 1.84 mmol), trans-1,2-diaminocyclohexane (21.2 mL, 0.184 mmol) and CuI (0.210 g, 1.10 mmol) and deoxygenated with argon for 30 minutes. After stirring at 110° C. for 48 hours, the reaction mixture was cooled and diluted with MeOH (3 mL) and a solution of 7:1 MeOH/$NH_4OH$ (3 mL) and filtered through Celite. The filtrate was concentrated and then suspended with $CH_2Cl_2$ (20 mL) and water (20 mL) and extracted with $CH_2Cl_2$ (4×50 mL). The combined organics were dried ($Na_2SO_4$) and concentrated. Purification by flash chromatography (silica gel, $CH_2Cl_2$/(80:18:2 $CH_2Cl_2$/MeOH/$NH_4OH$), 100:0 to 0:100) yielded the title compound (29.6 mg, 7%) as a brown solid: $^1H$ NMR (500 MHz, $CDCl_3$) δ 8.05 (s, 1H), 7.80 (d, J=7.5 Hz, 2H), 7.73 (d, J=2.0 Hz, 1H), 7.57 (d, J=9.0 Hz, 1H), 7.47-7.42 (m, 3H), 7.37-7.33 (m, 3H), 6.68 (d, J=7.5 Hz, 1H), 4.60 (t, J=7.0 Hz, 2H), 3.06 (br m, 2H), 2.62 (br m, 4H), 1.81 (br m, 4H); ESI MS m/z 425 [M+H]$^+$; HPLC (Method A) 96.4% (AUC), $t_R$=15.0 mm.

e) 2-Phenyl-5-(1-(2-(pyrrolidine-1-yl)ethyl)-1H-indazol-5-yl)furo[3,2-c]pyridine-4(5H)-one hydrochloride

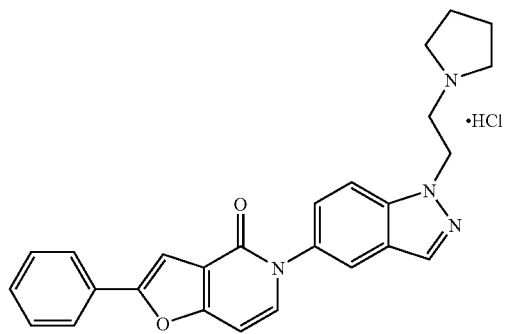

Chemical Formula: $C_{26}H_{25}ClN_4O_2$
Exact Mass: 460.17
Molecular Weight: 460.96

A solution of 2-phenyl-5-(1-(2-(pyrrolidine-1-yl)ethyl)-1H-indazol-5-yl)furo[3,2-c]pyridine-4(5H)-one (27.6 mg, 0.065 mmol) in $CH_2Cl_2$ (0.5 mL) was treated with anhydrous HCl in diethyl ether (65.0 μL, 0.065 mmol, 1.0 M). After stirring at ambient temperature for one hour, the reaction mixture was diluted with $Et_2O$ (50 mL). The resulting solids were collected by filtration and dried in a vacuum oven to yield the title compound (14.6 mg, 48%) as a brown solid. $^1H$ NMR (500 MHz, DMSO-$d_6$) δ 10.07 (br s, 0.5H), 8.28 (s, 1H), 7.92-7.89 (m, 4H), 7.66 (d, J=7.5 Hz, 1H), 7.56-7.48 (m, 4H), 7.40 (t, J=7.5 Hz, 1H), 6.91 (d, J=7.5 Hz, 1H), 4.87 (t, J=6.0 Hz, 2H), 3.77-3.73 (m, 2H), 3.56-3.55 (m, 2H), 3.09-3.06 (m, 2H), 2.01 (br m, 2H), 1.89-1.84 (br m, 2H); ESI MS m/z 425 [M+H]$^+$; HPLC (Method A) 95.4% (AUC), $t_R$=15.3 min.

Example 2

Preparation of 2-(4-Chlorophenyl)-5-(1-(2-(pyrrolidine-1-yl)ethyl)-1H-indazol-5-yl)furo[3,2-c]pyridine-4(5H)-one hydrochloride a) 2-(4-Chlorophenyl)-5H-furo[3,2-c]pyridine-4-one

Beilstein Registry number 7708433.

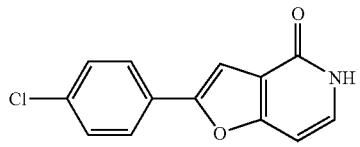

Chemical Formula: $C_{13}H_8ClNO_2$
Exact Mass: 245.02
Molecular Weight: 245.66

This molecule was prepared in accordance with the synthesis described in Krutosikova and Sleziak, *Collect. Czech. Chem. Commun.* 1996, 61, 1627-1636.

b) 5-Bromo-1-(2-(pyrrolidin-1-yl)ethyl)-1H-indazole

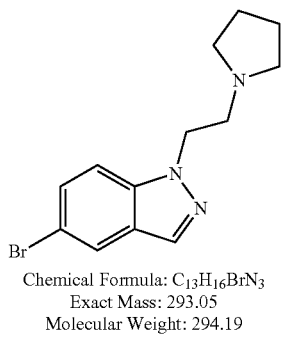

Chemical Formula: C₁₃H₁₆BrN₃
Exact Mass: 293.05
Molecular Weight: 294.19

Following the procedure of Example 1 (steps b-c), but substituting 4-bromo-2-methylaniline for 4-iodo-2-methylaniline, the title compound was prepared as an orange oil: $^1$H NMR (500 MHz, CDCl₃) δ 7.93 (s, 1H), 7.86 (d, J=1.8 Hz, 1H), 7.45 (dd, J=8.8, 17 Hz, 1H), 7.34 (d, J=8.9 Hz, 1H), 4.51 (t, J=7.2 Hz, 2H), 3.00 (t, J=7.3 Hz, 2H), 2.56 (m, 4H), 179-1.76 (m, 4H); ESI MS m/z 294 [M+H]⁺.

c) 2-(4-Chlorophenyl)-5-(1-(2-(pyrrolidine-1-yl)ethyl)-1H-indazol-5-yl)furo[3,2-c]pyridine-4(5H)-one

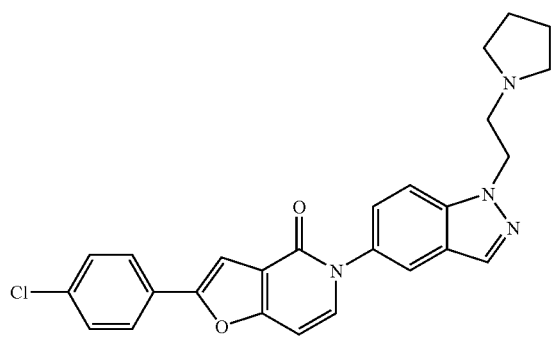

Chemical Formula: C₂₆H₂₃ClN₄O₂
Exact Mass: 458.15
Molecular Weight: 458.94

A solution of 5-bromo-1-(2-(pyrrolidin-1-yl)ethyl)-1H-indazole (0.349 g, 1.18 mmol) in NMP (3.3 mL) was added to 2-(4-chlorophenyl)-5H-furo[3,2-c]pyridine-4-one (0.347 g, 1.41 mmol), Cs₂CO₃ (0.768 g, 2.36 mmol), trans-1,2-bis(methylamino) cyclohexane (0.035 mL, 0.236 mmol) and CuI (0.269 g, 1.41 mmol) and deoxygenated with argon for 30 minutes. After stirring at 110° C. for 48 hours, the reaction mixture was cooled and diluted with CH₂Cl₂ (10 mL) and water (10 mL) and extracted with CH₂Cl₂ (4×50 mL). The organics were filtered through Celite and concentrated. Purification by flash chromatography (silica gel, CH₂Cl₂/(80:18:2 CH₂Cl₂/MeOH/NH₄OH), 100:0 to 0:100) followed by preparative HPLC (Phenomenex Luna C18 (2), 250.0×50.0 mm, 10 micron, H₂O with 0.05% trifluoroacetic acid (TFA) and CH₃CN with 0.05% TFA) yielded the title compound (7.5 mg, 13%) as a light yellow solid: ESI MS m/z 459 [M+H]⁺.

d) 2-(4-Chlorophenyl)-5-(1-(2-(pyrrolidine-1-yl)ethyl)-1H-indazol-5-yl)furo[3,2-c]pyridine-4(5H)-one hydrochloride

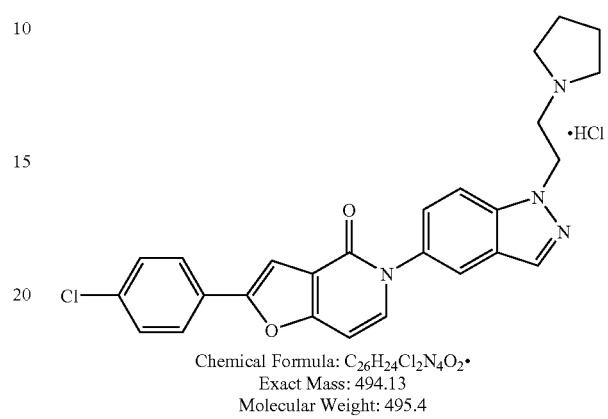

Chemical Formula: C₂₆H₂₄Cl₂N₄O₂·
Exact Mass: 494.13
Molecular Weight: 495.4

A solution of 2-(4-chlorophenyl)-5-(1-(2-(pyrrolidine-1-yl)ethyl)-1H-indazol-5-yl)furo[3,2-c]pyridine-4(5H)-one (6.7 mg, 0.014 mmol) in CDCl₃ (0.7 mL) was treated with anhydrous HCl in diethyl ether (14.5 µL, 0.014 mmol, 1.0 M). After stirring at ambient temperature for one hour, the reaction mixture was concentrated, dissolved in CH₃CN and H₂O, partially concentrated, then lyophilized to yield the title compound (6.5 mg, 91%) as a light yellow solid: $^1$H NMR (500 MHz, DMSO-d₆) δ 9.81 (br s, 0.5H), 8.28 (s, 1H), 7.92-7.89 (m, 4H), 7.68 (d, J=7.5 Hz, 1H), 7.63 (s, 1H), 7.56 (d, J=8.5 Hz, 2H), 7.53 (dd, J=9.0, 1.5 Hz, 1H), 6.91 (d, J=7.5 Hz, 1H), 4.86 (t, J=6.0 Hz, 2H), 3.76 (t, J=6.0 Hz, 2H), 3.57-3.56 (m, 2H), 3.11-3.07 (m, 2H), 2.01 (br m, 2H), 1.87-1.84 (br m, 2H); ESI MS m/z 459 [M+H]⁺; HPLC (Method A) 97.0% (AUC), $t_R$=17.0 min.

Example 3

Preparation of (R)-2-(4-chlorophenyl)-5-(1-(2-(2-hydroxymethyl)pyrrolidin-1-yl)ethyl)-1H-indazol-5-yl)furo[3,2-c]pyridine-4(5H)-one hydrochloride a) 1-(2,2-Dimethoxyethyl)-5-iodo-1H-indazole

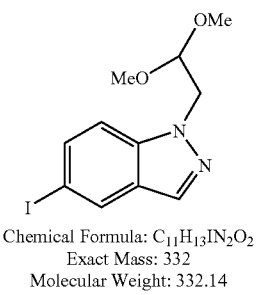

Chemical Formula: C₁₁H₁₃IN₂O₂
Exact Mass: 332
Molecular Weight: 332.14

To a solution of 5-iodio-1H-indazole (8.28 g, 33.9 mmol) in DMSO (104 mL) was added 2-bromoacetaldehyde dimethyl acetal (7.9 mL, 68 mmol) and Cs₂CO₃ (44.1 g, 136 mmol). The reaction mixture was stirred at 40° C. for 18 h; then the reaction mixture was diluted with H₂O (100 mL) and EtOAc (175 mL). The partitioned material was extracted with EtOAc (4×175 mL). The organics were washed with brine (2×100 mL), dried (Na₂SO₄), filtered, and concentrated. Purification by flash chromatography (silica gel, (hexanes with 0.1% Et₃N)/(EtOAc with 0.1% Et₃N), 100:0 to 90:10) yielded the title compound (4.49 g, 46%) as a light orange powder: ¹H NMR (500 MHz, CDCl₃) δ 8.07 (d, J=1.0 Hz, 1H), 7.92 (d, J=0.5 Hz, 1H), 7.60 (dd, J=9.0, 1.5 Hz, 1H), 7.28 (d, J=9.0 Hz, 1H), 4.71 (t, J=5.5 Hz, 1H), 4.44 (d, J=5.5 Hz, 2H), 3.33 (s, 6H).

b) 2-(4-Chlorophenyl)-5-(1-(2,2-dimethoxyethyl)-1H-indazol-5-yl)furo[3,2-c]pyridine-4-one

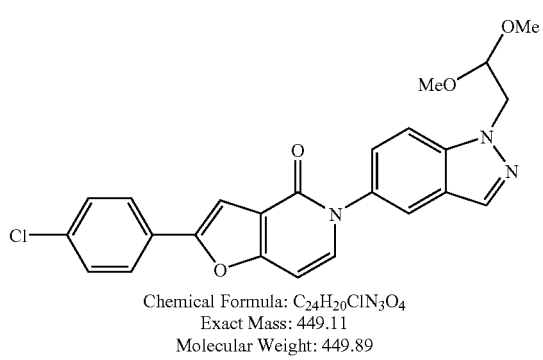

Chemical Formula: C₂₄H₂₀ClN₃O₄
Exact Mass: 449.11
Molecular Weight: 449.89

To a solution of 1-(2,2-dimethoxyethyl)-5-iodo-1H-indazole (3.14 g, 9.46 mmol) in DMSO (11.2 mL) was added 2-(4-chlorophenyl)-5H-furo[3,2-c]pyridine-4-one (2.32 g, 9.46 mmol), Cs₂CO₃ (3.39 g, 10.4 mmol), 8-hydroxyquinoline (0.274 g, 1.89 mmol) and CuI (2.16 g, 11.4 mmol). The solution was evacuated for 15 minutes under high vacuum then backfilled with argon. The process was repeated three times. The reaction mixture was stirred at 128° C. for 5 h; then the reaction mixture was cooled to 100° C. and maintained at this temperature for 18 h. The reaction mixture was diluted with 10% NH₄OH in H₂O (100 mL) and the resulting solids were washed with an additional 10% NH₄OH in H₂O solution (300 mL). The solids were dissolved in CH₂Cl₂ (100 mL) and washed with H₂O (2×50 mL). The organics were filtered to remove any excess solids and then concentrated. Purification by flash chromatography (silica gel, hexanes with 0.1% Et₃N to hexanes/MTBE/EtOAc 35:1.25:0.25 with 0.1% Et₃N, to hexanes/MTBE/EtOH 35:1.25:0.25 with 0.1% Et₃N, to CH₂Cl₂/(80:18:2 CH₂Cl₂/MeOH/NH₄OH), 1:1) yielded the title compound (1.78 g, 41%) as a brown solid: ¹H NMR (500 MHz, CDCl₃) δ 8.06 (s, 1H), 7.73-7.71 (m, 3H), 7.60 (d, J=9.0 Hz, 1H), 7.43-7.41 (m, 3H), 7.35 (d, J=7.5 Hz, 1H), 7.25 (s, 1H), 6.67 (d, J=7.5 Hz, 1H), 4.78 (t, J=5.5 Hz, 1H), 4.51 (d, J=5.0 Hz, 2H), 3.38 (s, 6H); ESI MS m/z 450 [M+H]⁺.

c) 2-(4-Chlorophenyl)-5-(1-(2,2-dihydroxyethyl)-1H-indazol-5-yl)furo[3,2-c]pyridine-4-one

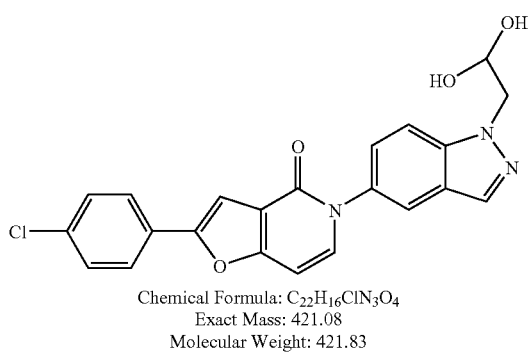

Chemical Formula: C₂₂H₁₆ClN₃O₄
Exact Mass: 421.08
Molecular Weight: 421.83

To a solution of 2-(4-chlorophenyl)-5-(1-(2,2-dimethoxyethyl)-1H-indazol-5-yl)furo[3,2-c]pyridine-4-one (1.66 g, 3.69 mmol) in THF (36 mL) at 40° C. was added HCl in H₂O (36 mL, 2.0 M). The solution was heated to 70° C. for 3 h then to 80° C. for 2 h. The reaction mixture was diluted with H₂O (75 mL) and CH₂Cl₂ (75 mL). The resulting solids were collected by filtration and dried to yield the title compound (1.00 g, 64%) as a light brown solid. ESI MS m/z 422 [M+H]⁺.

d) (R)-2-(4-Chlorophenyl)-5-(1-(2-(2-hydroxymethyl)pyrrolidin-1-yl)ethyl)-1H-indazol-5-yl)furo[3,2-c]pyridine-4-one

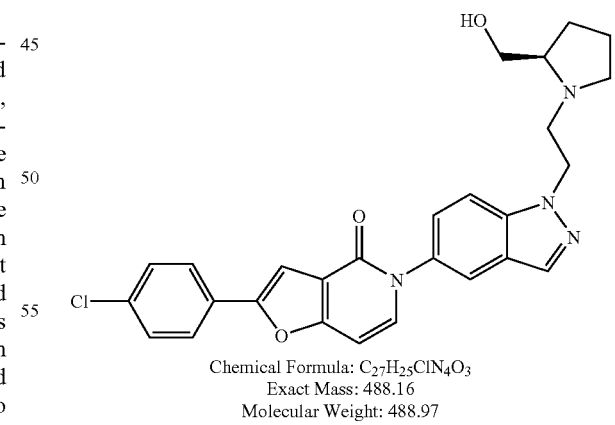

Chemical Formula: C₂₇H₂₅ClN₄O₃
Exact Mass: 488.16
Molecular Weight: 488.97

To a solution of 2-(4-chlorophenyl)-5-(1-(2,2-dihydroxyethyl)-1H-indazol-5-yl)furo[3,2-c]pyridine-4-one (86 mg, 0.20 mmol) in CH₂Cl₂ (2.0 mL), MeOH (1.0 mL) and AcOH (0.30 mL) was added (R)-2-hydroxymethylpyrrolidine (60 μL, 0.61 mmol) and picoline-borane complex (21.8 mg, 0.204 mmol) The solution was stirred at ambient temperature for 18 h. The reaction mixture was concentrated and then diluted with 1 N HCl (2.0 mL) and stirred at ambient temperature for 45 minutes. The mixture was made basic with NaHCO₃ and extracted with CH₂Cl₂ (3×15 mL). The organics were dried (Na₂SO₄), filtered, and concentrated. Purification by flash chromatography (silica gel, CH₂Cl₂/EtOH with 10% NH₄OH, 97.5:2.5) gave the title compound (65 mg, 65%) as an off-white powder: ¹H NMR (500 MHz, CDCl₃) δ 8.07 (s, 1H), 7.73-7.71 (m, 3H), 7.51 (d, J=9.0 Hz, 1H), 7.45 (d, J=2.0 Hz, 1H), 7.42 (d, J=8.5 Hz, 2H), 7.36 (d, J=7.5 Hz, 1H), 7.25 (s, 1H), 6.67 (d, J=7.5 Hz, 1H), 4.57-4.47 (m, 2H), 3.46 (dd, J=11.0, 3.5 Hz, 1H), 3.43-3.37 (m, 1H), 3.27 (d, J=10.5 Hz, 1H), 3.20 (dt, J=10.0, 3.0 Hz, 1H), 2.90-2.86 (m, 1H), 2.71-2.68 (m, 1H), 2.53 (br s, 1H), 2.424-2.37 (m, 1H), 1.87-1.64 (m, 4H); ESI MS m/z 489 [M+H]⁺; HPLC (Method A) >99% (AUC), $t_R$=15.7 min.

e) (R)-2-(4-Chlorophenyl)-5-(1-(2-(2-hydroxymethyl)pyrrolidin-1-yl)ethyl)-1H-indazol-5-yl)furo[3,2-c]pyridine-4-one hydrochloride

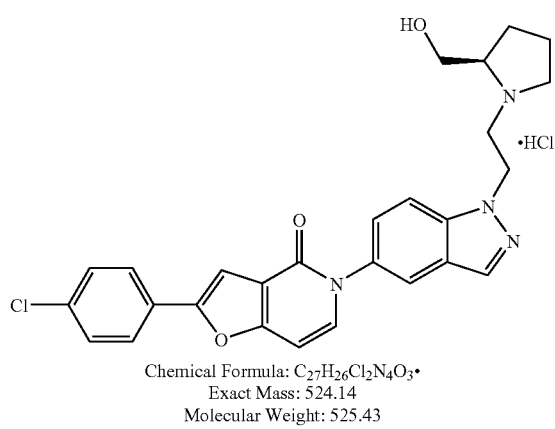

Chemical Formula: C₂₇H₂₆Cl₂N₄O₃·
Exact Mass: 524.14
Molecular Weight: 525.43

A solution of (R)-2-(4-chlorophenyl)-5-(1-(2-(2-hydroxymethyl)pyrrolidin-1-yl)ethyl)-1H-indazol-5-yl)furo[3,2-c]pyridine-4-one (65 mg, 0.13 mmol) in CH₂Cl₂ (2.0 mL) was treated with anhydrous HCl in diethyl ether (0.13 mL, 0.13 mmol, 1.0 M). After stirring at ambient temperature for 3 h, the solids were concentrated and dried to yield the title compound (63.5 mg, 90%) as an off-white solid: ¹H NMR (500 MHz, DMSO-d₆) δ 9.77 (br s, 1H), 8.25 (s, 1H), 7.92-7.89 (m, 4H), 7.69 (d, J=7.5 Hz, 1H), 7.63 (s, 1H), 7.57-7.51 (m, 3H), 6.91 (d, J=7.5 Hz, 1H), 5.52-5.51 (m, 1H), 4.94-4.85 (m, 2H), 3.96-3.94 (m, 1H), 3.81-3.78 (m, 1H), 3.71-3.65 (m, 3H), 3.57-3.35 (m, 1H), 3.18-3.13 (m, 1H), 2.11-1.98 (m, 2H), 1.88-1.72 (m, 2H); ESI MS m/z 489 [M+H]⁺; HPLC (Method A) >99% (AUC), $t_R$=16.3 min.

Example 4

Preparation of (S)-2-(4-Chlorophenyl)-5-(1-(2-(2-hydroxymethyl)pyrrolidin-1-yl)ethyl)-1H-indazol-5-yl)furo[3,2-c]pyridine-4(5H)-one hydrochloride a) (S)-2-(4-Chlorophenyl)-5-(1-(2-(2-hydroxymethyl)pyrrolidin-1-yl)ethyl)-1H-indazol-5-yl)furo[3,2-c]pyridine-4-one

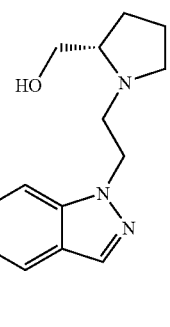

Chemical Formula: C₂₇H₂₅ClN₄O₃
Exact Mass: 488.16
Molecular Weight: 488.97

Following the procedure of Example 3, but substituting (S)-2-hydroxymethylpyrrolidine for (R)-2-hydroxymethylpyrrolidine, the title compound (64.9 mg, 65%) was prepared as an off-white solid: ¹H NMR (500 MHz, CDCl₃) δ 8.07 (s, 1H), 7.73-7.71 (m, 3H), 7.51 (d, J=8.5 Hz, 1H), 7.46-7.41 (m, 3H), 7.36 (d, J=7.0 Hz, 1H), 7.25 (s, 1H), 6.67 (d, J=7.5 Hz, 1H), 4.57-4.48 (m, 2H), 3.46 (dd, J=11.0, 3.5 Hz, 1H), 3.43-3.37 (m, 1H), 3.28-3.26 (m, 1H), 3.20 (dt, J=9.5, 2.5 Hz, 1H), 2.90-2.86 (m, 1H), 2.72-2.68 (m, 1H), 2.53 (br s, 1H), 2.42-2.37 (m, 1H), 1.87-1.65 (m, 4H); ESI MS m/z 489 [M+H]⁺; HPLC (Method A) >99% (AUC), $t_R$=15.7 min.

b) (S)-2-(4-Chlorophenyl)-5-(1-(2-(2-hydroxymethyl)pyrrolidin-1-yl)ethyl)-1H-indazol-5-yl)furo[3,2-c]pyridine-4-one hydrochloride

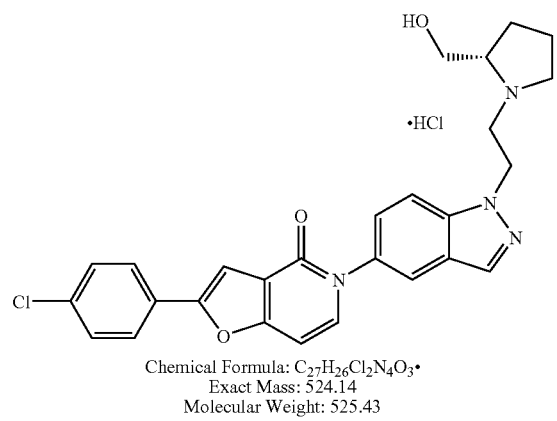

Chemical Formula: C₂₇H₂₆Cl₂N₄O₃·
Exact Mass: 524.14
Molecular Weight: 525.43

Following the procedure of Example 3, but substituting (S)-2-(4-chlorophenyl)-5-(1-(2-(2-hydroxymethyl)pyrrolidin-1-yl)ethyl)-1H-indazol-5-yl)furo[3,2-c]pyridine-4-one for (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (58 mg, 84%) was prepared as an off-white solid: $^1$H NMR (500 MHz, DMSO-$d_6$) δ 9.62 (br s, 1H), 8.27 (s, 1H), 7.92-7.88 (m, 4H), 7.68 (d, J=7.5 Hz, 1H), 7.63 (s, 1H), 7.57-7.52 (m, 3H), 6.91 (d, J=7.5 Hz, 1H), 5.54-5.53 (m, 1H), 4.93-4.84 (m, 2H), 3.96-3.94 (m, 1H), 3.81-3.78 (m, 1H), 3.70-3.65 (m, 3H), 3.57-3.56 (m, 1H), 3.17-3.14 (m, 1H), 2.12-1.99 (m, 2H), 1.88-1.72 (m, 2H); ESI MS m/z 489 [M+H]$^+$; HPLC (Method A) >99% (AUC), $t_R$=16.4 min.

Example 5

Preparation of (S)-2-(4-chlorophenyl)-5-(1-(2-(3-hydroxy)pyrrolidin-1-yl)ethyl)-1H-indazol-5-yl)furo[3,2-c]pyridine-4(5H)-one hydrochloride a) (S)-2-(4-Chlorophenyl)-5-(1-(2-(3-hydroxypyrrolidin-1-yl)ethyl)-1H-indazol-5-yl)furo[3,2-c]pyridine-4-one

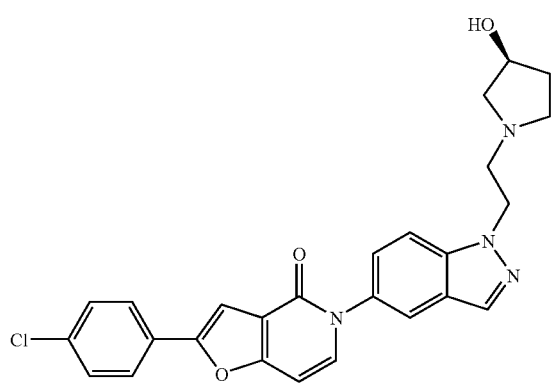

Chemical Formula: $C_{26}H_{23}ClN_4O_3$
Exact Mass: 474.15
Molecular Weight: 474.94

Following the procedure of Example 3, but substituting (S)-3-hydroxypyrrolidine for (R)-2-hydroxymethylpyrrolidine, the title compound (11.5 mg, 45%) was prepared as an off-white solid: $^1$H NMR (500 MHz, CDCl$_3$) δ 8.05 (s, 1H), 7.73-7.15 (m, 3H), 7.55 (d, J=9.0 Hz, 1H), 7.44-7.41 (m, 3H), 7.35 (d, J=7.5 Hz, 1H), 7.25 (s, 1H), 6.67 (d, J=7.5 Hz, 1H), 4.56 (t, J=7.0 Hz, 2H), 4.32 (s, 1H), 3.04 (t, J=7.0 Hz, 2H), 2.98-2.93 (m, 1H), 2.73 (d, J=9.5 Hz, 1H), 2.57-2.54 (m, 1H), 2.39-2.34 (m, 1H), 2.16-2.14 (m, 1H), 1.79-1.72 (m, 2H); ESI MS m/z 475 [M+H]$^+$; HPLC (Method A) 96.2% (AUC), $t_R$=16.2 min.

b) (S)-2-(4-Chlorophenyl)-5-(1-(2-(3-hydroxypyrrolidin-1-yl)ethyl)-1H-indazol-5-yl)furo[3,2-c]pyridine-4-one hydrochloride

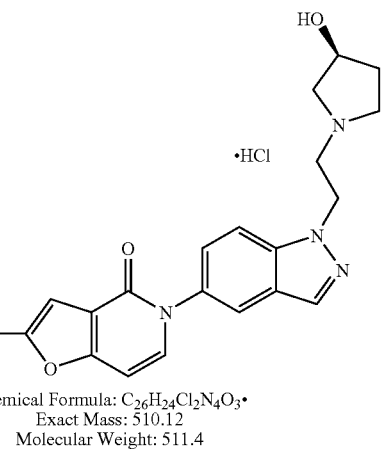

Chemical Formula: $C_{26}H_{24}Cl_2N_4O_3$·
Exact Mass: 510.12
Molecular Weight: 511.4

Following the procedure of Example 3, but substituting (S)-2-(4-chlorophenyl)-5-(1-(2-(3-hydroxypyrrolidin-1-yl)ethyl)-1H-indazol-5-yl)furo[3,2-c]pyridine-4-one for (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (11.2 mg, 91%) was prepared as an off-white solid: $^1$H NMR (500 MHz, DMSO-$d_6$) δ 10.24 (br s, 1H), 8.28-8.27 (m, 1H), 7.92-7.87 (m, 4H), 7.68 (d, J=7.5 Hz, 1H), 7.55 (dd, J=7.0, 2.0 Hz, 2H), 7.52 (d, J=9.0 Hz, 1H), 6.90 (d, J=7.5 Hz, 1H), 5.48 (s, 1H), 4.88-4.87 (m, 2H), 4.44-4.37 (m, 1H), 3.80-3.61 (m, 3H), 3.41 (br s, 1H), 3.15-3.00 (m, 2H), 2.23 (br s, 1H), 1.96-1.82 (m, 2H); ESI MS m/z 475 [M+H]$^+$; HPLC (Method A) 95.3% (AUC), $t_R$=15.5 min.

Example 6

Preparation of (R)-2-(4-Chlorophenyl)-5-(1-(2-(3-hydroxy)pyrrolidin-1-yl)ethyl)-1H-indazol-5-yl)furo[3,2-c]pyridine-4(5H)-one hydrochloride a) (R)-2-(4-Chlorophenyl)-5-(1-(2-(3-hydroxypyrrolidin-1-yl)ethyl)-1H-indazol-5-yl)furo[3,2-c]pyridine-4-one

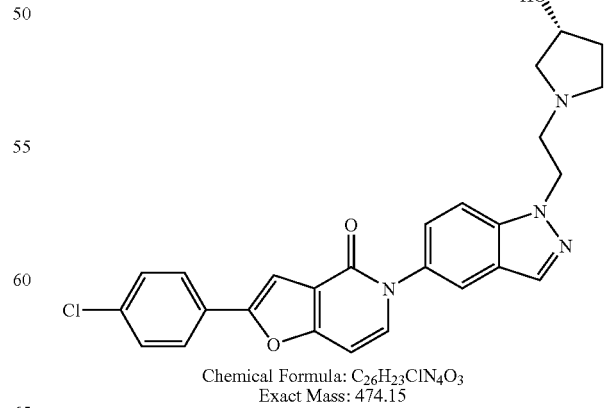

Chemical Formula: $C_{26}H_{23}ClN_4O_3$
Exact Mass: 474.15
Molecular Weight: 474.94

Following the procedure of Example 3, but substituting (R)-3-hydroxypyrrolidine for (R)-2-hydroxymethylpyrrolidine, the title compound (21.8 mg, 29%) was prepared as an off-white solid: $^1$H NMR (300 MHz, CDCl$_3$) δ 8.05 (s, 1H), 7.74-7.54 (m, 5H), 7.44-7.41 (m, 3H), 7.36 (d, J=7.8 Hz, 1H), 6.67 (d, J=7.2 Hz, 1H), 4.57 (t, J=6.9 Hz, 2H), 4.32 (s, 1H), 3.04 (t, J=6.9 Hz, 2H), 3.00-2.93 (m, 1H), 2.74 (d, J=9.9 Hz, 1H), 2.58-2.53 (m, 1H), 2.40-2.32 (m, 1H), 2.20-2.12 (m, 1H), 1.86-1.71 (m, 2H); ESI MS m/z 475 [M+H]$^+$; HPLC (Method A) 97.4% (AUC), t$_R$=15.7 min.

b) (R)-2-(4-Chlorophenyl)-5-(1-(2-(3-hydroxypyrrolidin-1-yl)ethyl)-1H-indazol-5-yl)furo[3,2-c]pyridine-4-one hydrochloride

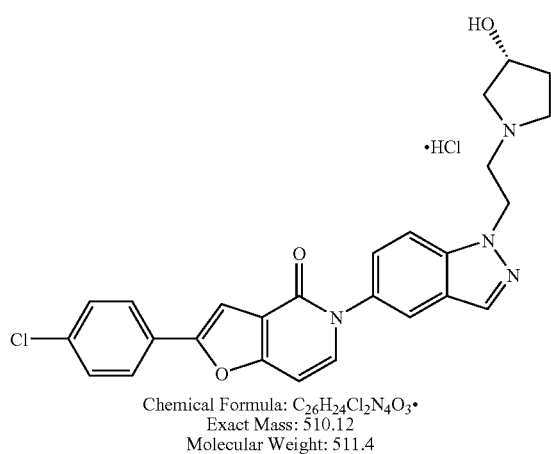

Chemical Formula: C$_{26}$H$_{24}$Cl$_2$N$_4$O$_3$·
Exact Mass: 510.12
Molecular Weight: 511.4

Following the procedure of Example 3, but substituting (R)-2-(4-chlorophenyl)-5-(1-(2-(3-hydroxypyrrolidin-1-yl)ethyl)-1H-indazol-5-yl)furo[3,2-c]pyridine-4-one for the (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (22.2 mg, quantitative) was prepared as an off-white solid: mp 242-246° C. (decomposition); ESI MS m/z 475 [M+H]$^+$; HPLC (Method A) 97.6% (AUC), t$_R$=15.4 min.

Example 7

Preparation of 2-(4-Chlorophenyl)-5-(1-((4,5dihydro-1H-imidazol-2-yl)methyl)-1H-indazol-5-yl)furo[3,2-c]pyridine-4(5H)-one hydrochloride a) Furo[3,2-c]pyridin-4(5H)-one Beilstein Registry Number 742679

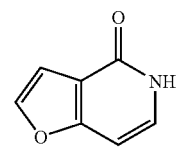

Chemical Formula: C$_7$H$_5$NO$_2$
Exact Mass: 135.03
Molecular Weight: 135.12

This compound was prepared in accordance with the procedure of Koreňova, et al., *Collect. Czech. Chem. Commun.* 1997, 52, 192-198.

b) 2-Bromo-5-(3-methyl-4-nitrophenyl)furo[3,2-c]pyridin-4(5H)-one

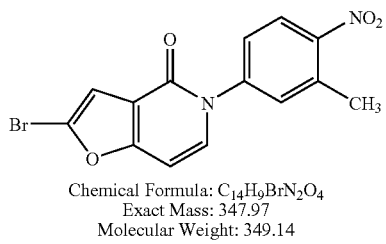

Chemical Formula: C$_{14}$H$_9$BrN$_2$O$_4$
Exact Mass: 347.97
Molecular Weight: 349.14

4-Fluoro-2-methyl-1-nitrobenzene (2.3 mL, 19 mmol) was added to a suspension of furo[3,2-c]pyridin-4(5H)-one (2.115 g, 15.67 mmol) and Cs$_2$CO$_3$ (5.097 g, 15.67 mmol) in anhydrous DMF (100 mL) and the resulting suspension was heated to 125° C. and stirred for 15 h. H$_2$O was added and the aqueous suspension was filtered. The solid was dried under reduced pressure to afford 4.6 g of crude 5-(3-methyl-4-nitrophenyl)furo[3,2-c]pyridin-4(5H)-one, which was used without further purification.

Pyridinium hydrobromide perbromide (1.14 g, 3.57 mmol) was added to a solution of crude 5-(3-methyl-4-nitrophenyl)furo[3,2-c]pyridin-4(5H)-one (963 mg, 3.57 mmol) in AcOH (10 mL) under a stream of N$_2$ and the resulting suspension was heated to ≈45° C. for 2 h. The suspension was concentrated under reduced pressure and the residue was diluted in H$_2$O. The resulting aqueous suspension was filtered and the solid was dried under reduced pressure to afford 1.7 g of a yellow solid. Flash chromatography on silica gel (4:1 hexanes/EtOAc) yielded the title compound (417 mg, 34%) as a yellow solid: $^1$H NMR (500 MHz, CDCl$_3$) δ 8.13 (d, J=8.4 Hz, 1H), 7.44-7.38 (m, 2H), 7.22 (d, J=7.5 Hz, 1H), 6.96 (s, 1H), 6.65 (d, J=7.5 Hz, 1H), 2.67 (s, 3H); ESI MS m/z 349 [M+H]$^-$.

c) 2-Bromo-5-(1H-indazol-5-yl)furo[3,2-c]pyridin-4(5H)-one

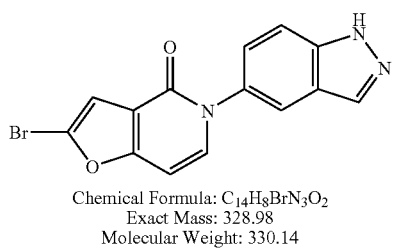

Chemical Formula: C$_{14}$H$_8$BrN$_3$O$_2$
Exact Mass: 328.98
Molecular Weight: 330.14

Fe powder (1.30 g, 23.2 mmol) and NH$_4$Cl (69 mg, 1.3 mmol) were added to a suspension of 2-bromo-5-(3-methyl-4-nitrophenyl)furo[3,2-c]pyridin-4(5H)-one (896 mg, 2.58 mmol) in 4:1 EtOH/H$_2$O (60 mL) and the resulting suspension was heated at reflux for 14 h. The suspension was filtered through Celite, while warm, and the filtrate was concentrated to afford 800 mg of crude 5-(4-amino-3-methylphenyl)-2-bromofuro[3,2-c]pyridin-4(5H)-one as a yellow solid.

NaNO$_2$ (174 mg, 2.52 mmol) was added to a solution of crude 5-(4-amino-3-methylphenyl)-2-bromofuro[3,2-c]pyridin-4(5H)-one (800 mg, 2.52 mmol) in 5:1 AcOH/H$_2$O (24 mL) and the resulting solution was stirred at 25° C. for 14 h. The solution was concentrated under reduced pressure. Flash chromatography on silica gel (49:1 CH$_2$Cl$_2$/MeOH) afforded the title compound (373 mg, 44%) as a yellow solid: $^1$H NMR (300 MHz, CDCl$_3$) δ 13.30-13.25 (br s, 1H, NH), 8.16 (s, 1H), 7.81 (d, J=1.8 Hz, 1H), 7.69 (d, J=7.5 Hz, 1H), 7.64 (d, J=8.7 Hz, 1H), 7.35 (dd, J=8.7, 1.8 Hz, 1H), 7.19 (d, J=0.6 Hz, 1H), 6.85 (dd, J=7.5, 0.6 Hz, 1H).

d) Methyl-2(5-(2-bromo-4-oxofuro[3,2-c]pyridine-5(4H)-yl) 1H-indazol-1-yl)acetate

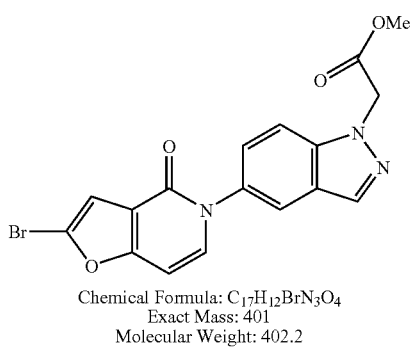

Chemical Formula: C$_{17}$H$_{12}$BrN$_3$O$_4$
Exact Mass: 401
Molecular Weight: 402.2

To a solution of 2-bromo-5-(1H-indazol-5-yl)furo[3,2-c]pyridin-4(5H)-one (1.13 g, 3.41 mmol) in DMSO (10.5 mL) was added methyl bromoacetate (0.64 mL, 6.8 mmol) and Cs$_2$CO$_3$ (4.44 g, 13.6 mmol). The reaction mixture was stirred at ambient temperature for 18 h; then additional methyl bromoacetate (0.30 mL) was added. After 3 h, additional methyl bromoacetate (0.30 mL) was added. The reaction mixture was stirred for 3.5 h and then the reaction mixture was diluted with H$_2$O (50 mL) and extracted with CH$_2$Cl$_2$ (4×25 mL). The extracts were washed with brine (3×25 mL), dried (Na$_2$SO$_4$) and concentrated. Purification by flash chromatography (silica gel, CH$_2$Cl$_2$/MTBE, 4:1) yielded the title compound (0.77 g, 56%) as a light yellow solid: $^1$H NMR (500 MHz, CDCl$_3$) δ 8.10 (s, 1H), 7.73 (s, 1H), 7.43 (s, 2H), 7.30 (d, J=7.5 Hz, 1H), 6.97 (s, 1H), 6.60 (d, J=7.0 Hz, 1H), 5.21 (s, 2H), 3.77 (s, 3H).

e) Methyl-2-(5-(2-(4-chlorophenyl)-4-oxofuro[3,2-c]pyridin-5(4H)-yl)-1H-indazol-1-yl)acetate

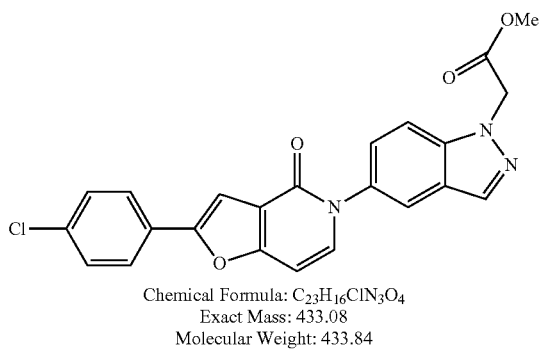

Chemical Formula: C$_{23}$H$_{16}$ClN$_3$O$_4$
Exact Mass: 433.08
Molecular Weight: 433.84

To a solution of methyl-2(5-(2-bromo-4-oxofuro[3,2-c]pyridine-5(4H)-yl)1H-indazol-1-yl)acetate (0.77 g, 19 mmol) in DMSO (44 mL) was added 4-chlorophenyl boronic acid (0.32 g, 2.1 mmol), K$_2$CO$_3$ (0.52 g, 3.8 mmol) and bis(triphenylphosphine)palladium (II) chloride (0.13 g, 0.19 mmol). The solution was evacuated for 15 minutes under high vacuum then backfilled with argon. The process was repeated three times. The reaction mixture was stirred at 90° C. for 2 h; then the reaction mixture was diluted with H$_2$O (20 mL) and extracted with CH$_2$Cl$_2$ (3×40 mL). The extracts were washed with brine (2×50 mL), dried (Na$_2$SO$_4$), filtered and concentrated. Purification by flash chromatography (silica gel, CH$_2$Cl$_2$/MTBE, 100:0 to 1:1) yielded the title compound (0.38 mg, 46%) as a light yellow solid: $^1$H NMR (300 MHz, CDCl$_3$) δ 8.12 (s, 1H), 7.77-7.63 (m, 4H), 7.53-7.41 (m, 4H), 7.35 (d, J=7.5 Hz, 1H), 6.68 (dd, J=7.5, 0.9 Hz, 1H), 5.22 (s, 2H), 3.78 (s, 3H); ESI MS m/z 434 [M+H]$^+$.

f) 2-(4-Chlorophenyl)-5-(1-((4,5-dihydro-1H-imidazol-2-yl)methyl)-1H-indazol-5-yl)furo[3,2-c]pyridine-4(5H)-one

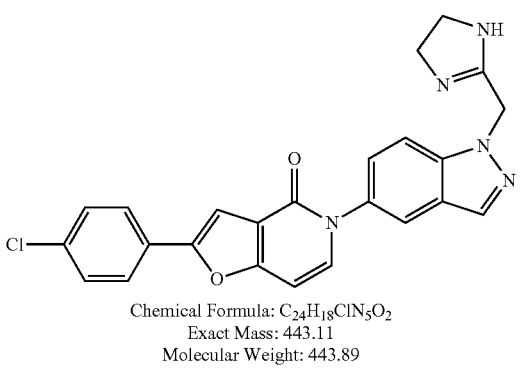

Chemical Formula: C$_{24}$H$_{18}$ClN$_5$O$_2$
Exact Mass: 443.11
Molecular Weight: 443.89

To a 0° C. solution of ethylenediamine (68 mL, 1.0 mmol) in toluene (0.36 mL) was slowly added trimethyl aluminium (0.50 mL, 10 M in toluene) over ten minutes. The solution was allowed to stir at 0° C. for 5 minutes; then a suspension of methyl-2-(5-(2-(4-chlorophenyl)-4-oxofuro[3,2-c]pyridin-5

(4H)-yl)-1H-indazol-1-yl)acetate (0.22 g, 0.50 mmol) in toluene (7.27 mL) was added and the reaction mixture was heated to reflux. The reaction mixture was stirred at reflux for 18 h; then the reaction mixture was diluted with $H_2O$ (2 mL) and the solids were removed by filtration. The filtrate was extracted with $CH_2Cl_2$ (3×20 mL) and the extracts were dried ($Na_2SO_4$), filtered and concentrated. Purification by flash chromatography (silica gel, $CH_2Cl_2$/9:1 EtOH with $NH_4OH$, 100:0 to 90:10) yielded the title compound (47.6 mg, 21%) as an off-white solid: $^1$H NMR (500 MHz, DMSO-$d_6$) δ 8.15 (s, 1H), 7.91 (d, J=9.0 Hz, 1H), 7.83 (d, J=1.5 Hz, 1H), 7.74 (d, J=9.0 Hz, 1H), 7.69 (d, J=7.5 Hz, 1H), 7.64 (s, 1H), 7.57-7.55 (m, 2H), 7.42 (dd, J=9.0, 2.0 Hz, 2H), 6.89 (d, J=7.0 Hz, 1H), 5.21 (s, 2H) 3.51 (br s, 1H), 3.30 (s, 4H); ESI MS m/z 444 [M+H]$^+$; HPLC (Method A) 95.7% (AUC), $t_R$=15.8 min.

g) 2-(3-Chlorophenyl)-5-(1-(2-(4,5-dihydroimidazol-2-yl)ethyl)-1H-indazol-5-yl)furo[3,2-c]pyridine-4(5H)-one hydrochloride

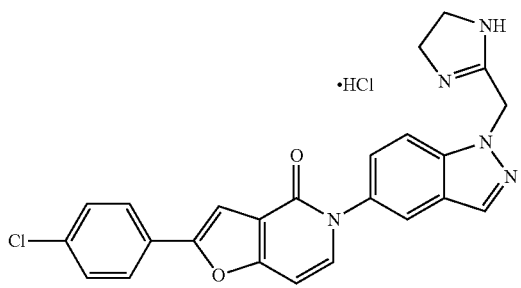

Chemical Formula: $C_{24}H_{19}Cl_2N_5O_2 \cdot$
Exact Mass: 479.09
Molecular Weight: 480.35

Following the procedure of Example 3, but substituting 2-(3-chlorophenyl)-5-(1-(2-(pyrrolidine-1-yl)ethyl)-1H-indazol-5-yl)furo[3,2-c]pyridine-4(5H)-one for (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (41.7 mg, 86%) was prepared as an off-white solid: $^1$H NMR (500 MHz, DMSO-$d_6$) δ 10.14 (br s, 2H), 8.33 (s, 1H), 7.92-7.87 (m, 4H), 7.66 (d, J=7.5 Hz, 1H), 7.63 (s, 1H), 7.57-7.54 (m, 3H), 6.92 (d, J=7.5 Hz, 1H), 5.69 (s, 2H), 3.86 (s, 4H); ESI MS m/z 444 [M+H]$^+$, HPLC (Method A) 95.3% (AUC), $t_R$=15.5 min.

Example 8

Preparation of 2-(3-Chlorophenyl)-5-(1-(2-(pyrrolidine-1-yl)ethyl)-1H-indazol-5-yl)furo[3,2-c]pyridine-4(5H)-one hydrochloride a) 2-(3-Chlorophenyl)-5H-furo[3,2-c]pyridine-4-one

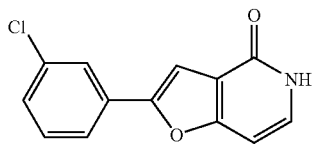

Chemical Formula: $C_{13}H_8ClNO_2$
Exact Mass: 245.02
Molecular Weight: 245.66

This molecule was prepared in accordance with the synthesis described in Krutosikova and Sleziak, Collect. Czech. Chem. Commun. 1996, 61, 1627-1636: $^1$H NMR (500 MHz, DMSO-$d_6$) δ 11.53 (s, 1H), 7.91 (t, J=1.5 Hz, 1H), 7.81 (d, J=7.5 Hz, 1H), 7.60 (s, 1H), 7.50 (t, J=8.0 Hz, 1H), 7.42 (dd, J=7.0, 1.0 Hz, 1H), 7.35 (t, J=7.0 Hz, 1H), 6.70 (d, J=7.0 Hz, 1H).

b) 2-(3-Chlorophenyl)-5-(3-methyl-4-nitrophenyl)furo[3,2-c]pyridin-4(5H)-one

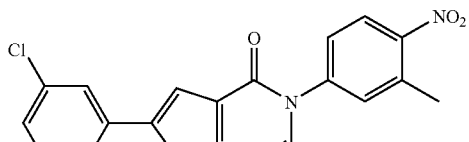

Chemical Formula: $C_{20}H_{13}ClN_2O_4$
Exact Mass: 380.06
Molecular Weight: 380.78

To a solution of 2-(3-chlorophenyl)-5H-furo[3,2-c]pyridine-4-one (1.00 g, 4.08 mmol) in DMF (9.46 mL) was added 5-fluoro-2-nitrotoluene (0.57 mL, 4.7 mmol) and $Cs_2CO_3$ (1.32 g, 4.08 mmol). After stirring at 120° C. for 48 h, the reaction mixture was cooled and the solids were collected by filtration. The solids were washed with EtOAc (300 ml) to yield the title compound (1.22 g, 78%) as a golden yellow solid: $^1$H NMR (500 MHz, DMSO-$d_6$) δ 8.14 (d, J=8.6 Hz, 1H), 7.97 (t, J=17 Hz, 1H), 7.86 (d, J=6.9 Hz, 1H), 7.74 (s, 1H), 7.73 (d, J=7.0 Hz, 1H), 7.68 (d, J=2 Hz, 1H), 7.60 (dd, J=8.0, 2.2 Hz, 1H), 7.53 (t, J=8.0 Hz, 1H), 7.46-7.44 (m, 1H), 6.97 (d, J=7.5 Hz, 1H), 2.58 (s, 3H).

b) 5-(4-Amino-3-methylphenyl)-2-(3-chlorophenyl)furo[3,2-c]pyridine-4(5H)-one

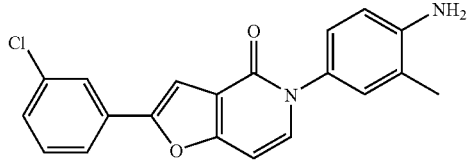

Chemical Formula: $C_{20}H_{15}ClN_2O_2$
Exact Mass: 350.08
Molecular Weight: 350.8

A solution of 2-(3-chlorophenyl)-5-(3-methyl-4-nitrophenyl)furo[3,2-c]pyridin-4(5H)-one (1.20 g, 3.15 mmol) in EtOH (21.2 mL) and $H_2O$ (5.16 mL) was treated with iron powder (1.52 g, 28.3 mmol) and $NH_4Cl$ (72.2 mg, 1.35 mmol). After stirring at reflux for 18 h, the reaction mixture was filtered through Celite® and the filtrate was concentrated to yield the title compound (1.02 g, 92%) as a light orange solid: $^1H$ NMR (300 MHz, DMSO-$d_6$) δ 7.95 (s, 1H), 7.84 (d, J=7.5 Hz, 1H), 7.67 (s, 1H), 7.55-7.42 (m, 3H), 6.94-6.78 (m, 3H), 6.67 (d, J=8.4 Hz, 1H), 5.11 (s, 2H), 2.09 (s, 3H).

c) 2-(3-Chlorophenyl)-5-(1H-indazol-5-yl)furo[3,2-c]pyridin-4(5H)-one

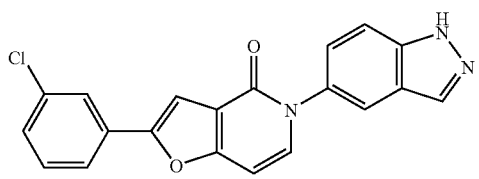

Chemical Formula: $C_{20}H_{12}ClN_3O_2$
Exact Mass: 361.06
Molecular Weight: 361.78

A solution of 5-(4-amino-3-methylphenyl)-2-(3-chlorophenyl)furo[3,2-c]pyridine-4(5H)-one (1.02 g, 2.91 mmol) in AcOH (23 mL) was treated with a solution of $NaNO_2$ (0.20 g, 2.9 mmol) in $H_2O$ (0.65 mL). After stirring at ambient temperature for 12 h, the reaction mixture was concentrated. The resulting solid was partitioned in $CH_2Cl_2$ and water. Any solids were removed by filtration. The filtrate was extracted with $CH_2Cl_2$ (4×30 mL). The organics were dried ($Na_2SO_4$), filtered, recombined with the removed solids and concentrated. Purification by flash chromatography (silica gel, $CH_2Cl_2$/MeOH, 100:0 to 90:10) gave the title compound (0.409 g, 40%) as a tan solid: $^1H$ NMR (300 MHz, DMSO-$d_6$) δ 13.29 (s, 1H), 8.17 (m, 1H), 7.96 (t, J=1.8 Hz, 1H), 7.87-7.83 (m, 2H), 7.73-7.71 (m, 2H), 7.65 (d, J=8.7 Hz, 1H), 7.52 (t, J=8.1 Hz, 1H), 7.46-7.43 (m, 1H), 7.38 (dd, J=9.0, 2.1 Hz, 1H), 6.89 (d, J=7.8 Hz, 1H).

d) 2-(3-Chlorophenyl)-5-(1-(2-(pyrrolidine-1-yl)ethyl)-1H-indazol-5-yl)furo[3,2-c]pyridine-4(5H)-one

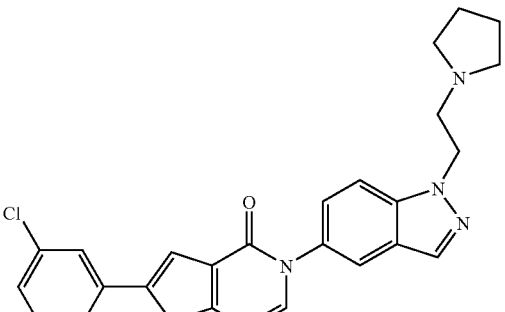

Chemical Formula: $C_{26}H_{23}ClN_4O_2$
Exact Mass: 458.15
Molecular Weight: 458.94

To a solution of 2-(3-chlorophenyl)-5-(1H-indazol-5-yl)furo[3,2-c]pyridin-4(5H)-one (0.365 g, 0.732 mmol) in DMSO (1.5 mL) and NMP (0.94 mL) was added (2-chloroethyl)pyrrolidine hydrochloride (0.273 g, 1.61 mmol) and $Cs_2CO_3$ (1.43 g, 4.39 mmol). The reaction mixture was stirred at ambient temperature for 18 h; then the reaction mixture was diluted with $H_2O$ (10 mL) and EtOAc (20 mL). The desired solids were collected by filtration. Purification by flash chromatography (silica gel, $CH_2Cl_2$/(80:18:2 $CH_2Cl_2$/MeOH/$NH_4OH$), 100:0 to 0:100) yielded the title compound (83.8 mg, 25%) as a light yellow solid: $^1H$ NMR (500 MHz, $CDCl_3$) δ 8.05 (s, 1H), 7.79 (t, J=2.0 Hz, 1H), 7.72 (d, J=1.5 Hz, 1H), 7.66 (d, J=7.5 Hz, 1H), 7.56 (d, J=9.0 Hz, 1H), 7.42 (dd, J=8.5, 2.0 Hz, 1H), 7.39-7.35 (m, 2H), 7.33-7.31 (m, 1H), 7.29 (s, 1H), 6.68 (d, J=7.5 Hz, 1H), 4.58 (t, J=7.5 Hz, 2H), 3.03 (t, J=7.0 Hz, 2H), 2.60 (m, 4H), 1.80 (m, 4H); ESI MS m/z 459 [M+H]$^+$; HPLC (Method A) >99% (AUC), $t_R$=16.7 min.

e) 2-(3-Chlorophenyl)-5-(1-(2-(pyrrolidine-1-yl)ethyl)-1H-indazol-5-yl)furo[3,2-c]pyridine-4(5H)-one hydrochloride

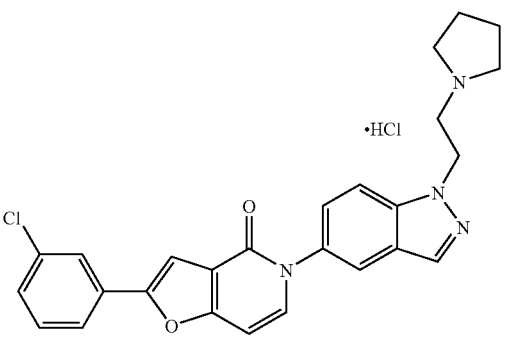

Chemical Formula: $C_{26}H_{23}ClN_4O_2$
Exact Mass: 458.15
Molecular Weight: 458.94

A solution of 2-(3-chlorophenyl)-5-(1-(2-(pyrrolidine-1-yl)ethyl)-1H-indazol-5-yl)furo[3,2-c]pyridine-4(5H)-one (83.mg, 0.18 mmol) in CH$_2$Cl$_2$ (1.5 mL) was treated with anhydrous HCl in diethyl ether (0.18 μL, 0.18 mmol, 1.0 M). After stirring at ambient temperature for 3 h, the solids were collected by filtration and dried to yield the title compound (76.3 mg, 84%) as a light yellow solid: $^1$H NMR (500 MHz, DMSO-d$_6$) δ 9.97 (br s, 1H), 8.24 (s, 1H), 7.96 (t, J=2.0 Hz, 1H), 7.92-7.85 (m, 3H), 7.71 (s, 1H), 7.69 (d, J=7.5 Hz, 1H), 7.54-7.51 (m, 2H), 7.45 (dd, J=8.0, 1.5 Hz, 1H), 6.92 (d, J=8.0 Hz, 1H), 4.87 (t, J=6.0 Hz, 2H), 3.75-3.74 (m, 2H), 3.55 (br m, 2H), 3.08 (br m, 2H), 2.01 (br m, 2H), 1.85-1.84 (br m, 2H); ESI MS m/z 459 [M+H]$^+$; HPLC (Method A) >99% (AUC), t$_R$=16.0 min.

Example 9

Preparation of 2-(2,4-Dichlorophenyl)-5-(1-(2-(pyrrolidin-1-yl)ethyl)-1H-indazol-5-yl)furo[3,2-c]pyridin-4(5H)-one hydrochloride a) 5-(1-(2-(Pyrrolidin-1-yl)ethyl)-1H-indazol-5-yl)furo[3,2-c]pyridin-4(5H)-one

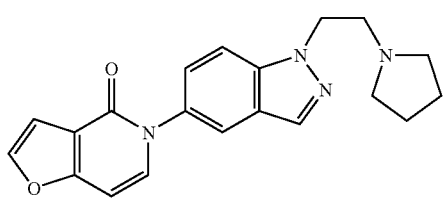

Chemical Formula: C$_{20}$H$_{20}$N$_4$O$_2$
Exact Mass: 348.16
Molecular Weight: 348.4

Furo[3,2-c]pyridin-4(5H)-one (402 mg, 2.98 mmol), 5-iodo-1-(2-(pyrrolidin-1-yl)ethyl)-1H-indazole (1.22 g, 3.58 mmol), CuI (682 mg, 3.58 mmol), Cs$_2$CO$_3$ (1.07 g, 3.28 mmol) and 8-hydroxyquinoline (87 mg, 0.60 mmol) were diluted with anhydrous DMSO (4 mL) and the resulting suspension was degassed for 45 min under reduced pressure. The suspension was put under an atmosphere of Ar, heated to 130° C. and stirred for 20 h. The suspension was cooled, H$_2$O (10 mL) was added and the aqueous suspension was filtered. The solid was washed with NH$_4$OH, dissolved in CH$_2$Cl$_2$ and dried over Na$_2$SO$_4$. The resulting solution was concentrated under reduced pressure to afford 1.516 g of a brown solid. Flash chromatography on silica gel (7:3 Et$_2$O/Et$_3$N) yielded the title compound (475 mg, 46%) as a light yellow powder: $^1$H NMR (500 MHz, CDCl$_3$) δ 8.04 (d, J=0.5 Hz, 1H), 7.70 (dd, J=2, 0.5 Hz, 1H), 7.58-7.52 (m, 2H), 7.41 (dd, J=8.5, 2.0 Hz, 1H), 7.33 (d, J=7.3 Hz, 1H), 7.04 (dd, J=3.5, 18 Hz, 1H), 6.64 (d, J=7.3 Hz, 1H), 4.57 (t, J=7.5 Hz, 2H), 3.03 (t, J=7.5 Hz, 2H), 2.65-2.55 (m, 4H), 1.84-1.72 (m, 4H).

b) 2-Bromo-5-(1-(2-(pyrrolidin-1-yl)ethyl)-1H-indazol-5-yl)furo[3,2-c]pyridin-4(5H)-one

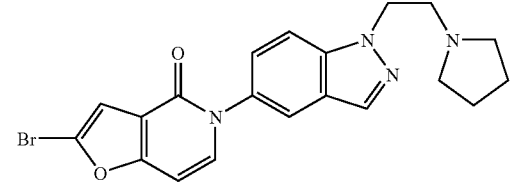

Chemical Formula: C$_{20}$H$_{19}$N$_4$O$_2$
Exact Mass: 426.07
Molecular Weight: 427.29

Pyridinium hydrobromide perbromide (1.68 g, 5.24 mmol) was added to a solution of 5-(1-(2-(pyrrolidin-1-yl)ethyl)-1H-indazol-5-yl)furo[3,2-c]pyridin-4(5H)-one (1.22 g, 3.49 mmol) in AcOH (35 mL) under a stream of N$_2$ and the resulting suspension was heated to 45° C. for 45 min. The suspension was cooled and the AcOH was removed under reduced pressure. The residue was diluted with 1:1 H$_2$O/saturated NaHCO$_3$ solution (50 mL) and the resulting aqueous solution was extracted with CH$_2$Cl$_2$ (3×50 mL). The combined organic extracts were dried over Na$_2$SO$_4$ and concentrated under reduced pressure to yield 2.5 g of a purple solid. Flash chromatography on silica gel [9:1 Et$_2$O/(9:1 MeOH/Et$_3$N)] afforded 550 mg (~80% pure) of the title compound as a white powder: $^1$H NMR (500 MHz, CDCl$_3$) δ 8.01 (d, J=0.5 Hz, 1H), 7.69 (dd, J=1.8, 0.5 Hz, 1H), 7.54 (d, J=8.8 Hz, 1H), 7.39 (dd, J=8.8, 18 Hz, 1H), 7.31 (d, J=7.3 Hz, 1H), 6.96 (d, J=0.5 Hz, 1H), 6.60 (dd, J=7.3, 0.5 Hz, 1H), 4.57 (t, J=7.3 Hz, 2H), 3.02 (t, J=7.3 Hz, 2H), 2.62-2.56 (m, 4H), 1.83-1.77 (m, 4H); ESI MS m/z 427 [M+H]$^+$.

c) 2-(2,4-Dichlorophenyl)-5-(1-(2-(pyrrolidin-1-yl)ethyl)-1H-indazol-5-yl)furo[3,2-c]pyridin-4(5H)-one hydrochloride

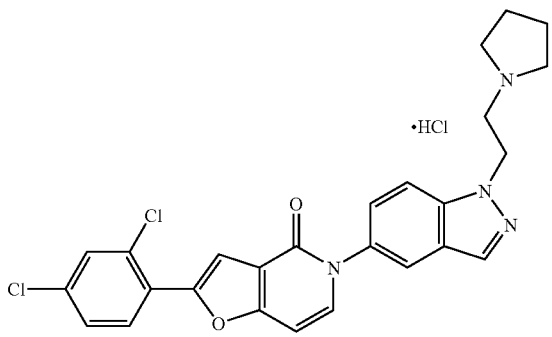

Chemical Formula: C$_{26}$H$_{23}$Cl$_3$N$_4$O$_2$
Exact Mass: 528.09
Molecular Weight: 529.85

2-Bromo-5-(1-(2-(pyrrolidin-1-yl)ethyl)-1H-indazol-5-yl)furo[3,2-c]pyridin-4(5H)-one (73 mg, 0.17 mmol), 2,4-dichlorophenylboronic acid (36 mg, 0.19 mmol), K$_2$CO$_3$ (47 mg, 0.34 mmol) and Pd(PPh$_3$)$_2$Cl$_2$ (12 mg, 0.017 mmol) were diluted with anhydrous DMSO (4 mL) and the resulting suspension was degassed under reduced pressure for 45 min. The suspension was place under an atmosphere of Ar and heated to 95° C. for 1.75 h. The suspension was cooled and H₂O was added. The aqueous suspension was filtered, the solid was diluted with CH₂Cl₂ and the resulting solution was dried over Na₂SO₄ and concentrated under reduced pressure to afford 50 mg of a pink solid. Flash chromatography on silica gel [9:1 Et₂O/(4:1 MeOH/Et₃N)] yielded 24 mg (29%) of 2-(2,4-dichlorophenyl)-5-(1-(2-(pyrrolidin-1-yl)ethyl)-1H-indazol-5-yl)furo[3,2-c]pyridin-4(5H)-one as a white powder. A solution of 2-(2,4-dichlorophenyl)-5-(1-(2-(pyrrolidin-1-yl)ethyl)-1H-indazol-5-yl)furo[3,2-c]pyridin-4(5H)-one (17 mg, 0.035 mmol) in CH₂Cl₂ (5 mL) was treated with anhydrous HCl in diethyl ether (0.04 mL, 0.04 mmol, 1.0 M) and the resulting solution was stirred at 25° C. for 1 h. The solution was concentrated under reduced pressure with Et₂O to afford the title compound as a white powder: mp 258-260° C.; $^1$H NMR (500 MHz, DMSO-$d_6$) δ 9.74-9.82 (br s, 1H, NH), 8.29 (s, 1H), 7.99 (d, J=8.5 Hz, 1H), 7.92-7.87 (m, 2H), 7.84 (d, J=2.0 Hz, 1H), 7.74 (d, J=7.5 Hz, 1H), 7.63 (dd, J=8.5, 2.0 Hz, 1H), 7.59 (s, 1H), 7.53 (br d, J=9.5 Hz, 1H), 6.94 (d, J=7.5 Hz, 1H), 4.87 (t, J=5.5 Hz, 2H), 3.80-3.70 (m, 2H), 3.61-3.52 (m, 2H), 3.15-3.02 (m, 2H), 2.08-1.92 (m, 2H), 1.90-1.79 (m, 2H); ESI MS m/z 493 [M+H]$^+$.

Example 10

Preparation of 2-(4-Chloro-2-methoxyphenyl)-5-(1-(2-(pyrrolidin-1-yl)ethyl)-1H-indazol-5-yl)furo[3,2-c]pyridin-4(5H)-one hydrochloride

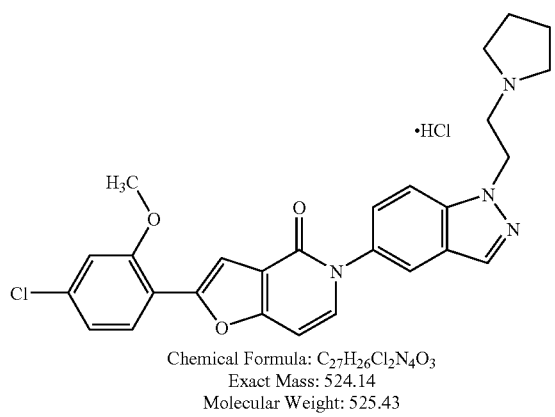

Chemical Formula: C₂₇H₂₆Cl₂N₄O₃
Exact Mass: 524.14
Molecular Weight: 525.43

2-Bromo-5-(1-(2-(pyrrolidin-1-yl)ethyl)-1H-indazol-5-yl)furo[3,2-c]pyridin-4(5H)-one (78 mg, 0.18 mmol), 4-chloro-2-methoxyphenylboronic acid (38 mg, 0.20 mmol), K₂CO₃ (51 mg, 0.37 mmol) and Pd(PPh₃)₂Cl₂ (13 mg, 0.018 mmol) were diluted with anhydrous DMSO (4 mL) and the resulting suspension was degassed under reduced pressure for 45 min. The suspension was place under an atmosphere of Ar and heated to 95° C. for 2 h. The suspension was cooled and H₂O was added. The aqueous suspension was extracted with EtOAc and the combined organic extracts were washed with brine, dried over Na₂SO₄ and concentrated under reduced pressure to afford 47 mg of a white powder. Flash chromatography on silica gel [9:1 Et₂O/(1:1 MeOH/Et₃N)] yielded 20 mg of a white powder. Final purification by preparative HPLC (Phenomenex Luna C18 (2), 250.0×50.0 mm, 10 micron, H₂O with 0.05% TFA and CH₃CN with 0.05% TFA) yielded 9 mg (10%) of 2-(4-chloro-2-methoxyphenyl)-5-(1-(2-(pyrrolidin-1-yl)ethyl)-1H-indazol-5-yl)furo[3,2-c]pyridin-4(5H)-one as a white solid. Following the procedure of Example 9, the HCl salt was made to give the title compound as a white solid: mp 240-242° C.; $^1$H NMR (500 MHz, DMSO-$d_6$) δ 10.15-10.01 (br s, 1H, NH), 8.28 (s, 1H), 7.94-7.85 (m, 3H), 7.69 (d, J=7.2 Hz, 1H), 7.52 (dd, J=6.7, 1.8 Hz, 1H), 7.36 (s, 1H), 7.31 (d, J=1.8 Hz, 1H), 7.19 (dd, J=8.4, 1.8 Hz, 1H), 6.91 (d, J=7.2 Hz, 1H), 4.88 (t, J=6.0 Hz, 2H), 4.03 (s, 3H), 3.78-3.70 (m, 2H), 3.62-3.50 (m, 2H), 3.14-3.00 (m, 2H), 2.08-1.96 (m, 2H), 1.90-1.80 (m, 2H); ESI MS m/z 489 [M+H]$^+$.

Example 11

Preparation of 2-(2-Chlorophenyl)-5-(1-(2-(pyrrolidin-1-yl)ethyl)-1H-indazol-5-yl)furo[3,2-c]pyridin-4(5H)-one hydrochloride

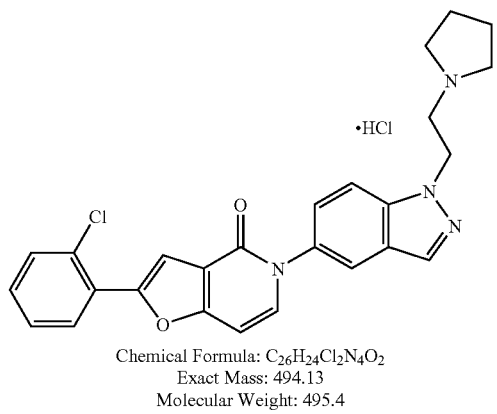

Chemical Formula: C₂₆H₂₄Cl₂N₄O₂
Exact Mass: 494.13
Molecular Weight: 495.4

2-Bromo-5-(1-(2-(pyrrolidin-1-yl)ethyl)-1H-indazol-5-yl)furo[3,2-c]pyridin-4(5H)-one (80 mg, 0.19 mmol), 2-chlorophenylboronic acid (32 mg, 0.21 mmol), K₂CO₃ (52 mg, 0.38 mmol) and Pd(PPh₃)₂Cl₂ (13 mg, 0.019 mmol) were diluted with anhydrous DMSO (4 mL) and the resulting suspension was degassed under reduced pressure for 45 min. The suspension was place under an atmosphere of Ar and heated to 95° C. for 2 h. The suspension was cooled and H₂O was added. The aqueous suspension was extracted with EtOAc and the combined organic extracts were washed with brine, dried over Na₂SO₄ and concentrated under reduced pressure to afford 77 mg of a white powder. Flash chromatography on silica gel [9:1 CH₂Cl₂/(9:1 MeOH/Et₃N)] yielded 56 mg of a white powder. Final purification by preparative HPLC (Phenomenex Luna C18 (2), 250.0×50.0 mm, 10 micron, H₂O with 0.05% TFA and CH₃CN with 0.05% TFA) yielded 31 mg (36%) of 2-(2-chlorophenyl)-5-(1-(2-(pyrrolidin-1-yl)ethyl)-1H-indazol-5-yl)furo[3,2-c]pyridin-4(5H)-one as a white powder. Following the procedure of Example 9, the HCl salt was prepared to afford the title compound as a white solid: mp 102-104° C.; $^1$H NMR (500 MHz, DMSO-$d_6$) δ 9.90-9.80 (br s, 1H, NH), 8.29 (s, 1H), 7.98 (dd, J=8.0, 1.5 Hz, 1H), 7.93-7.89 (m, 2H), 7.73 (d, J=7.3 Hz, 1H), 7.66 (dd, J=8.0, 1.5 Hz, 1H), 7.57-7.51 (m, 3H), 7.46 (ddd, J=8.0, 8.0, 15 Hz, 1H), 6.94 (d, J=7.3 Hz, 1H), 4.87 (t, J=6.0 Hz, 2H), 3.79-3.72 (m, 2H), 3.60-3.52 (m, 2H), 3.13-3.02 (m, 2H), 2.08-1.97 (m, 2H), 1.90-1.81 (m, 2H); ESI MS m/z 459 [M+H]$^+$.

Example 12

Preparation of 5-Fluoro-2-(4-oxo-5-(1-(2-(pyrrolidin-1-yl)ethyl)-1H-indazol-5-yl)-4,5-dihydrofuro[3,2-c]pyridin-2-yl)benzonitrile hydrochloride

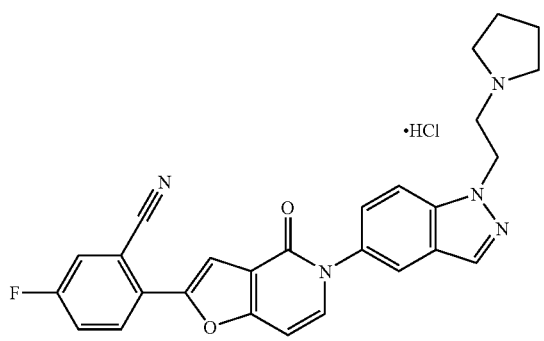

Chemical Formula: $C_{27}H_{23}ClFN_5O_2$
Exact Mass: 503.15
Molecular Weight: 503.96

Following the procedure of Example 11, but substituting 2-cyano-4-fluorophenylboronic acid for 2-chlorophenylboronic acid, adding additional 2-cyano-4-fluorophenylboronic acid and $K_2CO_3$ after 4 h and a total reaction time of 5 h, the title compound (22 mg, 23%) was prepared as a white powder: mp 120-122° C.; $^1$H NMR (500 MHz, DMSO-$d_6$) δ 8.29 (s, 1H), 8.13 (dd, J=8.8, 5.5 Hz, 1H), 8.07 (dd, J=8.8, 2.5 Hz, 1H), 7.94-7.89 (m, 2H), 7-79 (dd, J=8.5, 2.5 Hz, 1H), 7.76 (d, J=7.5 Hz, 1H), 7.69 (s, 1H), 7.54 (dd, J=9.0, 1.5 Hz, 1H), 6.94 (d, J=7.5 Hz, 1H), 4.90-4.82 (m, 2H), 3.81-3.71 (m, 2H), 3.63-3.50 (m, 2H), 3.15-3.03 (m, 2H), 2.08-1.97 (m, 2H), 1.92-1.80 (m, 2H); ESI MS m/z 468 [M+H]$^+$.

Example 13

Preparation of 2-(2-Chloro-4-fluorophenyl)-5-(1-(2-(pyrrolidin-1-yl)ethyl)-1H-indazol-5-yl)furo[3,2-c]pyridin-4(5H)-one hydrochloride

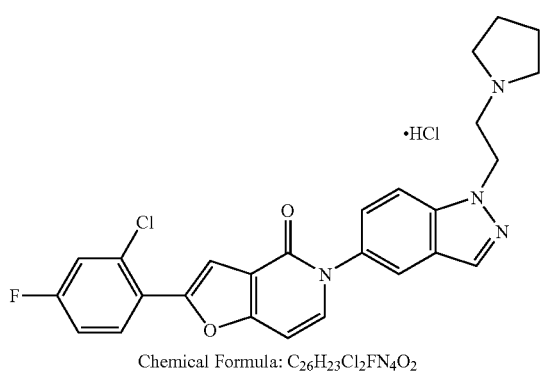

Chemical Formula: $C_{26}H_{23}Cl_2FN_4O_2$
Exact Mass: 512.12
Molecular Weight: 513.39

Following the procedure of Example 11, but substituting 2-chloro-4-fluorophenylboronic acid for 2-chlorophenylboronic acid, the title compound (32 mg, 34%) was prepared as a white powder: mp 140-142° C.; $^1$H NMR (500 MHz, DMSO-$d_6$) δ 10.20-10.10 (br s, 1H, NH), 8.29 (s, 1H), 8.01 (dd, J=8.3, 6.0 Hz, 1H), 7.92 (d, J=9.0 Hz, 1H), 7.90 (d, J=1.8 Hz, 1H), 7.71 (d, J=6.5 Hz, 1H), 7.68 (dd, J=9.0, 2.8 Hz, 1H), 7.53 (dd, J=9.0, 1.8 Hz, 1H), 7.51 (s, 1H), 7.44 (ddd, J=8.3, 8.0, 2.8 Hz, 1H), 6.93 (d, J=6.5 Hz, 1H), 4.89 (t, J=6.3 Hz, 2H), 3.76-3.70 (m, 2H), 3.58-3.52 (m, 2H), 3.10-3.02 (m, 2H), 2.05-1.98 (m, 2H), 1.90-1.81 (m, 2H); ESI MS m/z 477 [M+H]$^+$.

Example 14

Preparation of 2-(4-Chloro-2-fluorophenyl)-5-(1-(2-(pyrrolidin-1-yl)ethyl)-1H-indazol-5-yl)furo[3,2-c]pyridin-4(5H)-one hydrochloride

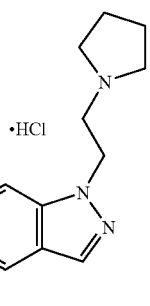

Chemical Formula: $C_{26}H_{23}Cl_2FN_4O_2$
Exact Mass: 512.12
Molecular Weight: 513.39

Following the procedure of Example 11, but substituting 4-chloro-2-fluorophenylboronic acid for 2-chlorophenylboronic acid, the title compound (31 mg, 33%) was prepared as a white powder: mp 256-258° C.; $^1$H NMR (500 MHz, DMSO-$d_6$) δ 10.12-10.05 (br s, 1H, NH), 8.28 (s, 1H), 7.96 (dd, J=8.5, 8.5 Hz, 1H), 7.94-7.88 (m, 2H), 7.74 (d, J=7.5 Hz, 1H), 7.68 (d, J=11.0 Hz, 1H), 7.52 (br d, J=8.5 Hz, 1H), 7.48 (d, J=8.5 Hz, 1H), 7.36 (s, 1H), 6.94 (d, J=7.5 Hz, 1H), 4.92-4.80 (m, 2H), 3.80-3.71 (m, 2H), 3.60-3.49 (m, 2H), 3.13-3.01 (m, 2H), 2.07-1.92 (m, 2H), 1.90-1.80 (m, 2H); ESI MS m/z 477 [M+H]+.

Example 15

Preparation of 2-(4-Fluorophenyl)-5-(1-(2-(pyrrolidin-1-yl)ethyl)-1H-indazol-5-yl)furo[3,2-c]pyridin-4(5H)-one hydrochloride a) 2-Bromo-5-(1-(2-(pyrrolidin-1-yl)ethyl)-1H-indazol-5-yl)furo[3,2-c]pyridin-4(5H)-one

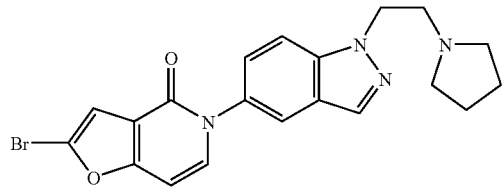

Chemical Formula: C20H19BrN4O2
Exact Mass: 426.07
Molecular Weight: 427.29

1-(2-Chloroethyl)pyrrolidine hydrochloride (213 mg, 1.25 mmol) was added to a suspension of 2-bromo-5-(1H-indazol-5-yl)furo[3,2-c]pyridin-4(5H)-one (187 mg, 0.570 mmol) and Cs2CO3 (1.11 g, 3.42 mmol) in anhydrous DMSO (3 mL) and the resulting suspension was stirred at 25° C. for 14 h. H2O (10 mL) was added and the aqueous suspension was filtered. The solid was dried under reduced pressure. Flash chromatography on silica gel [4.75:4.75:0.5 MTBE/CH2Cl2/(9:1 EtOH/NH4OH)] afforded the title compound (113 mg, 47%) as a light yellow powder with data matching those reported in Example 9.

b) 2-(4-Fluorophenyl)-5-(1-(2-(pyrrolidin-1-yl)ethyl)-1H-indazol-5-yl)furo[3,2-c]pyridin-4(5H)-one hydrochloride

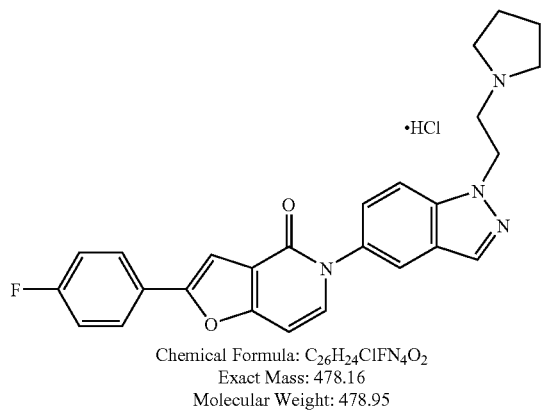

Chemical Formula: C26H24ClFN4O2
Exact Mass: 478.16
Molecular Weight: 478.95

2-Bromo-5-(1-(2-(pyrrolidin-1-yl)ethyl)-1H-indazol-5-yl)furo[3,2-c]pyridin-4(5H)-one (82 mg, 0.19 mmol), 4-fluorophenylboronic acid (30 mg, 0.21 mmol), K2CO3 (53 mg, 0.38 mmol) and Pd(PPh3)2Cl2 (13 mg, 0.019 mmol) were diluted with anhydrous DMSO (2 mL) and the resulting suspension was degassed under reduced pressure for 45 min. The suspension was place under an atmosphere of Ar and heated to 95° C. for 2.5 h. The suspension was cooled and H2O was added. The resulting aqueous suspension was filtered and the solid was dried under reduced pressure to afford 67 mg of a tan powder. Flash chromatography on silica gel [85:15 MTBE/(9:1 EtOH/Et3N)] afforded 26 mg of an off-white powder. The powder was dissolved in CH2Cl2 (10 mL) and activated charcoal was added. The resulting suspension was stirred at 25° C. for 10 min. The suspension was filtered through Celite and the filtrate was concentrated under reduced pressure to give 22 mg of an off-white powder. Final purification by preparative HPLC (Phenomenex Luna C18 (2), 250.0×50.0 mm, 10 micron, H2O with 0.05% TFA and CH3CN with 0.05% TFA) yielded 17 mg (20%) of 2-(4-fluorophenyl)-5-(1-(2-(pyrrolidin-1-yl)ethyl)-1H-indazol-5-yl)furo[3,2-c]pyridin-4(5H)-one as a white powder. Following the procedure of Example 9, the HCl salt was prepared to afford the title compound as a white powder: mp 218-220° C.; 1H NMR (500 MHz, DMSO-d6) δ 9.90-9.82 (br s, 1H, NH), 8.28 (s, 1H), 7.95 (dd, J=9.0, 5.0 Hz, 2H), 7.92-7.89 (m, 2H), 7.67 (d, J=7.5 Hz, 1H), 7.56 (s, 1H), 7.53 (br d, J=9.0 Hz, 1H), 7.36 (dd, J=9.0, 9.0 Hz, 2H), 6.91 (d, J=7.5 Hz, 1H), 4.91-4.83 (m, 2H), 3.80-3.72 (m, 2H), 3.63-3.51 (m, 2H), 3.14-3.05 (m, 2H), 2.09-1.98 (m, 2H), 1.90-1.80 (m, 2H); ESI MS m/z 443 [M+H]+.

Example 16

Preparation of 5-(1-(2-(Pyrrolidin-1-yl)ethyl)-1H-indazol-5-yl)-2-(4-(trifluoro-methyl)phenyl)furo[3,2-c]pyridin-4(5H)-one hydrochloride

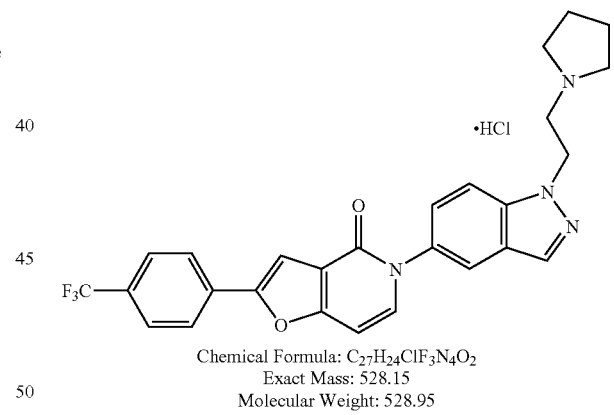

Chemical Formula: C27H24ClF3N4O2
Exact Mass: 528.15
Molecular Weight: 528.95

2-Bromo-5-(1-(2-(pyrrolidin-1-yl)ethyl)-1H-indazol-5-yl)furo[3,2-c]pyridin-4(5H)-one (83 mg, 0.20 mmol), 4-(trifluoromethyl)phenylboronic acid (41 mg, 0.21 mmol), K2CO3 (54 mg, 0.39 mmol) and Pd(PPh3)2Cl2 (14 mg, 0.020 mmol) were diluted with anhydrous DMSO (2 mL) and the resulting suspension was degassed under reduced pressure for 45 min. The suspension was placed under an atmosphere of Ar and heated to 95° C. for 2 h. The suspension was cooled and H2O was added. The resulting aqueous suspension was filtered and the solid was dried under reduced pressure to afford 78 mg of a tan powder. Flash chromatography on silica gel [9:1 CH2Cl2/(9:1 MeOH/Et3N)] afforded 38 mg of an off-white powder. Final purification using a strong cation exchanger (SCX) column (MeOH to 7:1 MeOH/NH4OH) afforded 16 mg (17%) of 5-(1-(2-(pyrrolidin-1-yl)ethyl)-1H- indazol-5-yl)-2-(4-(trifluoromethyl)phenyl)furo[3,2-c]pyridin-4(5H)-one as a white powder. Following the procedure of Example 9, the HCl salt was prepared to afford the title compound as a white powder: mp 252-254° C., $^1$H NMR (500 MHz, DMSO-$d_6$) δ 9.79-9.68 (br s, 1H, NH), 8.29 (s, 1H), 8.12 (d, J=8.0 Hz, 2H), 7.94-7.88 (m, 2H), 7.86 (d, J=8.0 Hz, 2H), 7.81 (s, 1H), 7.73 (d, J=7.0 Hz, 1H), 7.56-7.51 (m, 1H), 6.95 (d, J=7.0 Hz, 1H), 4.90-4.82 (m, 2H), 3.79-3.71 (m, 2H), 3.62-3.53 (m, 2H), 3.15-3.04 (m, 2H), 2.09-1.99 (m, 2H), 1.93-1.81 (m, 2H); ESI MS m/z 493 [M+H]$^+$.

Example 17

2-(5-Chloropyridin-2-yl)-5-(1-(2-(pyrrolidin-1-yl)ethyl)-1H-indazol-5-yl)furo[3,2-c]pyridin-4(5H)-one dihydrochloride

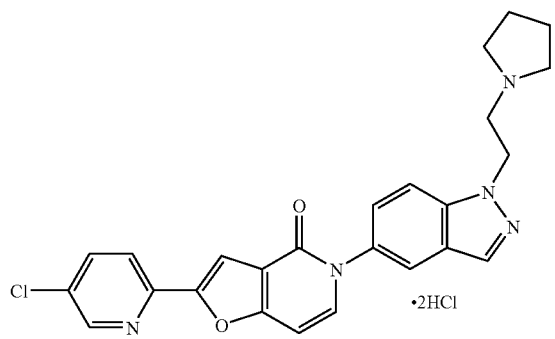

Chemical Formula: C$_{25}$H$_{24}$Cl$_3$N$_5$O$_2$
Exact Mass: 531.1
Molecular Weight: 532.85

2-Bromo-5-(1-(2-(pyrrolidin-1-yl)ethyl)-1H-indazol-5-yl)furo[3,2-c]pyridin-4(5H)-one (145 mg, 0.340 mmol), Pd(PPh$_3$)$_2$Cl$_2$ (39 mg, 0.034 mmol) and hexamethylditin (0.14 mL, 0.68 mmol) were diluted with anhydrous DMSO (4 mL) and the resulting solution was bubbled with N$_2$ while being heated to 80° C. Once the oil bath temperature reached 80° C., the bubbling was discontinued, and the reaction mixture was stirred at 80° C. for 45 min under N$_2$ atmosphere. The solution was cooled and diluted with EtOAc (50 mL). The resulting organic solution was washed with brine (2×50 mL), dried over Na$_2$SO$_4$ and concentrated under reduced pressure. The residue, 2-bromo-5-chloropyridine (174 mg, 0.340 mmol) and Pd(PPh$_3$)$_4$ (39 mg, 0.034 mmol) were diluted with anhydrous DMSO (4 mL). The resulting solution was degassed with N$_2$, heated to 110° C. and held at this temperature for 18 h. The solution was cooled, EtOAc (40 mL) was added and the resulting solution was washed with H$_2$O (10 mL). The organic solution was washed with brine (2×20 mL), dried over Na$_2$SO$_4$ and concentrated under reduced pressure to afford 55 mg of a tan powder. Flash chromatography on silica gel [9:1 CH$_2$Cl$_2$/(9:1 MeOH/Et$_3$N)] yielded 46 mg of a white powder. Final purification by preparative HPLC (Phenomenex Luna C18 (2), 250.0×50.0 mm, 10 micron, H$_2$O with 0.05% TFA and CH$_3$CN with 0.05% TFA) yielded 2-(5-chloropyridin-2-yl)-5-(1-(2-(pyrrolidin-1-yl)ethyl)-1H-indazol-5-yl)furo[3,2-c]pyridin-4(5H)-one (9 mg, 6%) as a white powder. According to the procedure of Example 9, the HCl salt was prepared to afford the title compound as a white solid mp 268-270° C.; $^1$H NMR (500 MHz, DMSO-$d_6$) δ 9.72-9.60 (br s, 1H, NH), 8.72 (d, J=2.5 Hz, 1H), 8.28 (s, 1H), 8.08 (dd, J=8.5, 2.5 Hz, 1H), 7.98 (d, J=8.5 Hz, 1H), 7.94-7.89 (m, 2H), 7.74 (d, J=7.5 Hz, 1H), 7.65 (s, 1H), 7.54 (br d, J=8.0 Hz, 1H), 6.95 (d, J=7.5 Hz, 1H), 4.90-4.82 (m, 2H), 3.80-3.73 (m, 2H), 3.63-3.51 (m, 2H), 3.14-3.03 (m, 2H), 2.07-1.95 (m, 2H), 1.91-1.82 (m, 2H); ESI MS m/z 460 [M+H]$^+$.

Example 18

Preparation of 2-(2-Fluorophenyl)-5-(1-(2-(pyrrolidin-1-yl)ethyl)-1H-indazol-5-yl)furo[3,2-c]pyridin-4(5H)-one hydrochloride

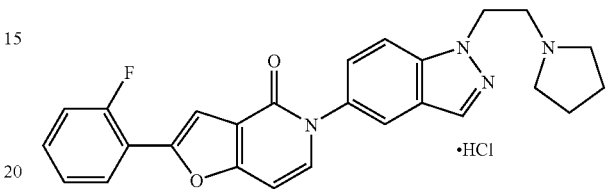

Chemical Formula: C$_{26}$H$_{24}$ClFN$_4$O$_2$
Exact Mass: 478.16
Molecular Weight: 478.95

Following the procedure of Example 11, but substituting 2-fluorophenylboronic acid for 2-chlorophenylboronic acid, the title compound (32 mg, 35%) was prepared as a white powder: mp 264-266° C.; $^1$H NMR (500 MHz, DMSO-$d_6$) δ 10.10-9.92 (br s, 1H, NH), 8.29 (s, 1H), 7.96 (ddd, J=8.0, 8.0, 2.0 Hz, 1H), 7.94-7.89 (m, 2H), 7.72 (d, J=7.5 Hz, 1H), 7.54 (dd, J=8.0, 1.5 Hz, 1H), 7.51-7.46 (m, 1H), 7.45-7.37 (m, 2H), 7.30 (d, J=3.0 Hz, 1H), 6.95 (d, J=7.5 Hz, 1H), 4.88 (t, J=6.0 Hz, 2H), 3.78-3.72 (m, 2H), 3.60-3.51 (m, 2H), 3.12-3.03 (m, 2H), 2.06-1.97 (m, 2H), 1.91-1.80 (m, 2H); ESI MS m/z 443 [M+H]$^+$.

Example 19

Preparation of 2-(2,4-Difluorophenyl)-5-(1-(2-(pyrrolidin-1-yl)ethyl)-1H-indazol-5-yl)furo[3,2-c]pyridin-4(5H)-one hydrochloride

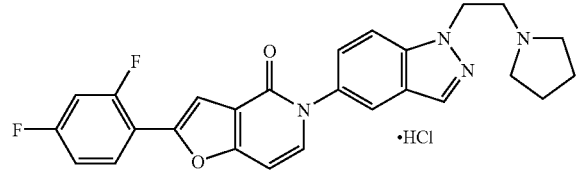

Chemical Formula: C$_{26}$H$_{23}$ClF$_2$N$_4$O$_2$
Exact Mass: 496.15
Molecular Weight: 496.94

Following the procedure of Example 11, but substituting 2,4-difluoro-phenylboronic acid for 2-chlorophenylboronic acid, the title compound (24 mg, 28%) was prepared as a white powder: mp 256-258° C.; $^1$H NMR (500 MHz, DMSO-$d_6$) δ 10.15-9.90 (br s, 1H, NH), 8.29 (s, 1H), 8.03-7.96 (m, 1H), 7.94-7.88 (m, 2H), 7.72 (d, J=7.5 Hz 1H), 7.53 (dd, J=9.0, 15 Hz, 1H), 7.52 (ddd, J=9.5, 9.5, 2.5 Hz, 1H), 7.30 (ddd, J=8.5, 8.5, 2.5 Hz, 1H), 7.28 (d, J=3.0 Hz, 1H), 6.94 (d, J=7.5 Hz, 1H), 4.88 (t, J=6.0 Hz, 2H), 3.78-3.70 (m, 2H), 3.59-3.51 (m, 2H), 3.12-3.01 (m, 2H), 2.06-1.97 (m, 2H), 1.90-1.80 (m, 2H); ESI MS m/z 461 [M+H]⁺.

Example 20

Preparation of 2-(2-Fluoro-4-methylphenyl)-5-(1-(2-(pyrrolidin-1-yl)ethyl)-1H-indazol-5-yl)furo[3,2-c]pyridin-4(5H)-one hydrochloride

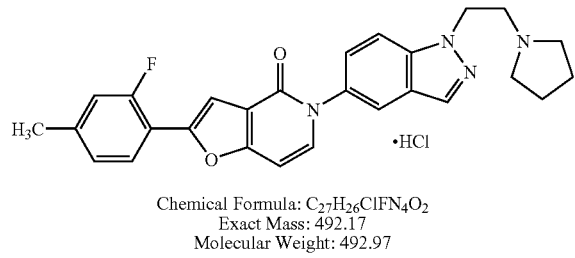

Chemical Formula: $C_{27}H_{26}ClFN_4O_2$
Exact Mass: 492.17
Molecular Weight: 492.97

Following the procedure of Example 11, but substituting 2-fluoro-4-methyl-phenylboronic acid for 2-chlorophenylboronic acid, the title compound (21 mg, 19%) was prepared as a white powder: mp 268-270° C.; ¹H NMR (500 MHz, DMSO-d₆) δ 10.15-10.06 (br s, 1H, NH), 8.28 (s, 1H), 7.92 (d, J=9.0 Hz, 1H), 7.90 (d, J=2.0 Hz, 1H), 7.83 (dd, J=8.0, 8.0 Hz, 1H), 7.70 (d, J=7.5 Hz, 1H), 7.53 (dd, J=9.0, 2.0 Hz, 1H), 7.26 (d, J=12.5 Hz, 1H), 7.23-7.18 (m, 2H), 6.93 (d, J=7.5 Hz, 1H), 4.88 (t, J=6.0 Hz, 2H), 3.78-3.72 (m, 2H), 3.60-3.52 (m, 2H), 3.12-3.03 (m, 2H), 2.39 (s, 3H), 2.07-1.98 (m, 2H), 1.90-1.81 (m, 2H); ESI MS m/z 457 [M+H]⁺.

Example 21

Preparation of 5-(1-(2-(Pyrrolidin-1-yl)ethyl)-1H-indazol-5-yl)-2-p-tolylfuro[3,2-c]pyridin-4(5H)-one hydrochloride

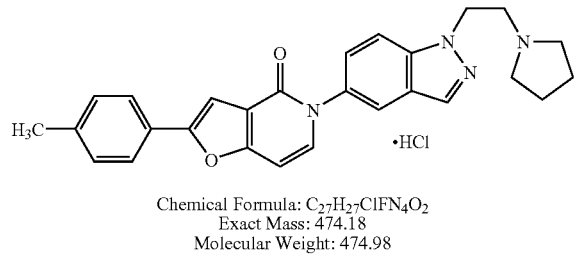

Chemical Formula: $C_{27}H_{27}ClN_4O_2$
Exact Mass: 474.18
Molecular Weight: 474.98

Following the procedure of Example 11, but substituting p-tolylboronic acid for the 2-chlorophenylboronic acid and triturating the free base with EtOAc and toluene, the title compound (19 mg, 19%) was prepared as an off-white powder: mp 262-264° C.; ¹H NMR (500 MHz, DMSO-d₆) δ 10.12-9.99 (br s, 1H, NH), 8.26 (br s, 1H), 7.92-7.75 (m, 2H), 7.79 (d, J=8.0 Hz, 2H), 7.65 (d, J=7.0 Hz, 1H), 7.51 (br d, J=7.5 Hz, 1H), 7.47 (s, 1H), 7.31 (d, J=8.0 Hz, 2H), 6.90 (d, J=7.5 Hz, 1H), 4.91-4.79 (m, 2H), 3.81-3.68 (m, 2H), 3.67-3.45 (m, 2H), 3.15-2.97 (m, 2H), 2.50 (s, 3H), 2.11-1.98 (m, 2H), 1.95-1.79 (m, 2H); ESI MS m/z 439 [M+H]⁺.

Example 22

Preparation of 2(Pyridin-3-yl)-5-(1-(2-(pyrrolidin-1-yl)ethyl)-1H-indazol-5-yl)furo[3,2-c]pyridin-4(5H)-one dihydrochloride

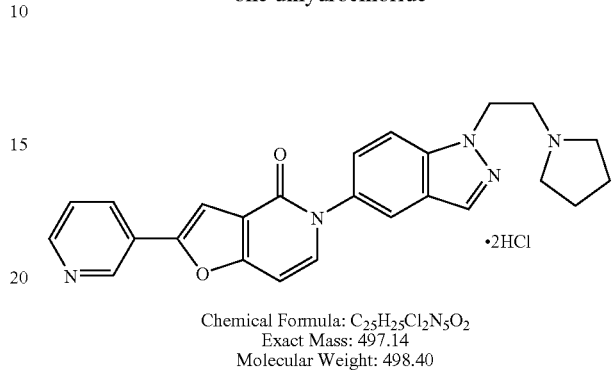

Chemical Formula: $C_{25}H_{25}Cl_2N_5O_2$
Exact Mass: 497.14
Molecular Weight: 498.40

Following the procedure of Example 11, but substituting pyridine-3-boronic acid 1,3-propanediol cyclic ester for 2-chlorophenylboronic acid, the title compound (7 mg, 7%) was prepared as a white powder: mp 188-190° C.; ¹H NMR (500 MHz, DMSO-d₆) δ 10.33-10.22 (br s, 1H, NH), 9.15 (s, 1H), 8.60 (d, J=4.5 Hz, 1H), 8.32-8.27 (m, 2H), 7.93 (d, J=9.0 Hz, 1H), 7.91 (s, 1H), 7.77 (s, 1H), 7.72 (d, J=7.3 Hz, 1H), 7.57 (dd, J=8.0, 4.8 Hz, 1H), 7.53 (br d, J=9.0 Hz, 1H), 6.94 (d, J=7.3 Hz, 1H), 4.90 (t, J=6.0 Hz, 2H), 3.75-3.70 (m, 2H), 3.60-3.48 (m, 2H), 3.10-3.01 (m, 2H), 2.05-1.95 (m, 2H), 1.90-1.79 (m, 2H); ESI MS m/z 426 [M+H]⁺.

Example 23

Preparation of 2-(5-Fluoropyridin-2-yl)-5-(1-(2-(pyrrolidin-1-yl)ethyl)-1H-indazol-5-yl)furo[3,2-c]pyridin-4(5H)-one dihydrochloride

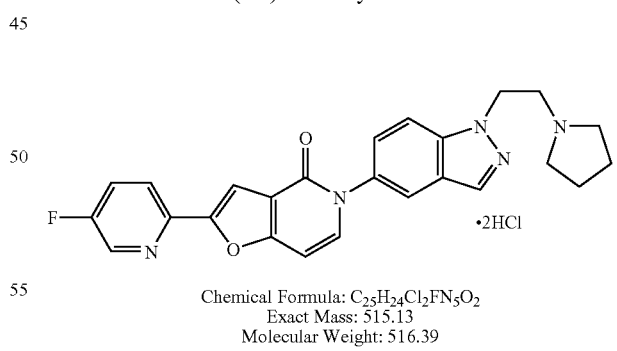

Chemical Formula: $C_{25}H_{24}Cl_2FN_5O_2$
Exact Mass: 515.13
Molecular Weight: 516.39

Following the procedure of Example 17, but substituting 2-bromo-5-fluoropyridine for 2-bromo-5-chloropyridine, the title compound (26 mg, 13%) was prepared as a yellow powder: mp 266-268° C.; ¹H NMR (500 MHz, DMSO-d₆) δ 10.27-10.19 (br s, 1H, NH), 8.68 (d, J=2.5 Hz, 1H), 8.28 (s, 1H), 8.04 (dd, J=9.0, 4.5 Hz, 1H), 7.94-7.87 (m, 3H), 7.73 (d, J=7.5 Hz, 1H), 7.58 (s, 1H), 7.54 (dd, J=9.0, 1.5 Hz, 1H), 6.94 (d, J=7.5 Hz, 1H), 4.89 (t, J=6.0 Hz, 2H), 3.78-3.71 (m, 2H), 3.65-3.49 (m, 2H), 3.11-3.02 (m, 2H), 2.06-1.95 (m, 2H), 1.89-1.81 (m, 2H); ESI MS m/z 444 [M+H]⁺.

Example 24

Preparation of 2-(Pyridin-2-yl)-5-(1-(2-(pyrrolidin-1-yl)ethyl)-1H-indazol-5-yl)furo[3,2-c]pyridin-4(5H)-one dihydrochloride

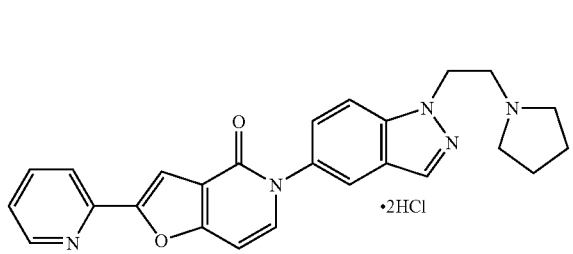

Chemical Formula: $C_{25}H_{25}Cl_2N_5O_2$
Exact Mass: 497.14
Molecular Weight: 498.40

Following the procedure of Example 17, but substituting 2-bromopyridine for 2-bromo-5-chloropyridine, the title compound (11 mg, 1.3%) was prepared as a yellow powder: mp 50-52° C.; ¹H NMR (500 MHz, DMSO-d₆) δ 10.15-10.04 (br s, 1H, NH), 8.69-8.65 (m, 1H), δ 28 (d, J=2.0 Hz, 1H), 7.98-7.88 (m, 4H), 7.75-7.71 (m, 1H), 7.59 (d, J=2.5 Hz, 1H), 7.56-7.52 (m, 1H), 7.43-7.38 (m, 1H), 6.95 (dd, J=7.5, 2.0 Hz, 1H), 4.92-4.85 (m, 2H), 3.78-3.71 (m, 2H), 3.59-3.52 (m, 2H), 3.12-3.03 (m, 2H), 2.07-1.98 (m, 2H), 1.90-1.81 (m, 2H); ESI MS m/z 426 [M+H]⁺.

Example 25

Preparation of 2-(6-Methylpyridazin-3-yl)-5-(1-(2-(pyrrolidin-1-yl)ethyl)-1H-indazol-5-yl)furo[3,2-c]pyridin-4(5H)-one hydrochloride

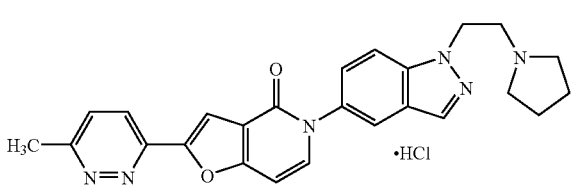

Chemical Formula: $C_{25}H_{25}ClN_6O_2$
Exact Mass: 476.17
Molecular Weight: 476.96

Following the procedure of Example 17, but substituting 3-bromo-6-methylpyridazine for 2-bromo-5-chloropyridine, the title compound (33 mg, 4%) was prepared as a yellow powder: mp 282-284° C.; ¹H NMR (500 MHz, DMSO-d₆) δ 10.32-10.11 (br s, 1H, NH), 8.29 (s, 1H), 8.14 (d, J=9.0 Hz, 1H), 7.96-7.91 (m, 2H), 7.83 (s, 1H), 7.77 (d, J=7.3 Hz, 1H), 7.72 (d, J=9.0 Hz, 1H), 7.55 (dd, J=8.5, 1.5 Hz, 1H), 6.98 (d, J=7.3 Hz, 1H), 4.89 (t, J=5.5 Hz, 2H), 3.78-3.71 (m, 2H), 3.70-3.45 (m, 2H), 3.12-3.01 (m, 2H), 2.68 (s, 3H), 2.06-1.98 (m, 2H), 1.90-1.81 (m, 2H); ESI MS m/z 441 [M+H]⁺.

Example 26

Preparation of 2-(Pyrimidin-2-yl)-5-(1-(2-(pyrrolidin-1-yl)ethyl)-1H-indazol-5-yl)furo[3,2-c]pyridin-4(5H)-one Dihydrochloride

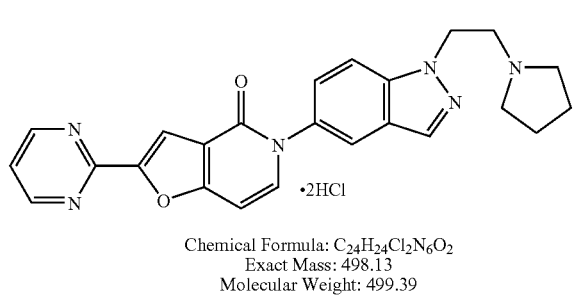

Chemical Formula: $C_{24}H_{24}Cl_2N_6O_2$
Exact Mass: 498.13
Molecular Weight: 499.39

Following the procedure of Example 11, but substituting 2-(tributylstannyl)pyrimidine for 2-chlorophenylboronic acid, the title compound (14 mg, 11%) was prepared as a white powder: mp 272-274° C.; ¹H NMR (500 MHz, DMSO-d₆) δ 9.91-9.82 (br s, 1H, NH), 8.92 (d, J=5.0 Hz, 2H), 8.29 (s, 1H), 7.95-7.90 (m, 2H), 7.79 (d, J=7.5 Hz, 1H), 7.69 (s, 1H), 7.55 (br d, J=9.0 Hz, 1H), 7.49 (d, J=5.0 Hz, 1H), 6.99 (d, J=7.5 Hz, 1H), 4.87 (t, J=6.0 Hz, 2H), 3.80-3.71 (m, 2H), 3.62-3.53 (m, 2H), 3.15-3.04 (m, 2H), 2.07-1.96 (m, 2H), 1.92-1.81 (m, 2H); ESI MS m/z 427 [M+H]⁺.

Example 27

Preparation of 2-(4-Chlorophenyl)-5-(1-(2-morpholinoethyl)-1H-indazol-5-yl)furo[3,2-c]pyridine-4-one hydrochloride a) 2-(4-Chlorophenyl)-5-(1-(2-morpholinoethyl)-1H-indazol-5-yl)furo[3,2-c]pyridine-4-one

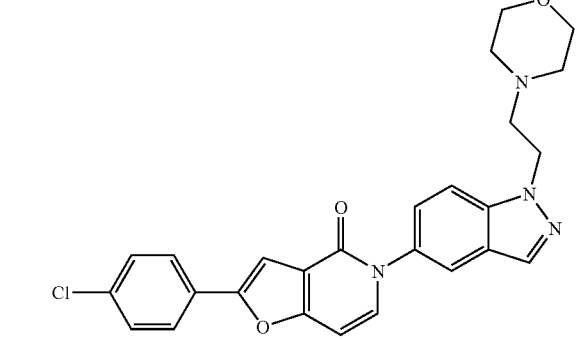

Chemical Formula: $C_{26}H_{23}ClN_4O_3$
Exact Mass: 474.15
Molecular Weight: 474.94

Following the procedure of Example 3 (step d), but substituting morpholine for (R)-2-hydroxymethylpyrrolidine, the title compound (38 mg, 26%) was prepared as a light yellow powder: ¹H NMR (500 MHz, CDCl₃) δ 8.05 (s, 1H), 7.73-7.72 (m, 3H), 7.54 (d, J=9.0 Hz, 1H), 7.47-7.42 (m, 3H), 7.36 (d, J=7.5 Hz, 1H), 7.25 (s, 1H), 6.68 (d, J=7.0 Hz, 1H), 4.56 (t, J=7.0 Hz, 2H), 3.69 (t, J=4.5 Hz, 4H), 2.91 (t, J=7.0 Hz, 2H), 2.53 (t, J=45 Hz, 4H); ESI MS m/z 475 [M+H]⁺.

b) 2-(4-Chlorophenyl)-5-(1-(2-morpholinoethyl)-1H-indazol-5-yl)furo[3,2-c]pyridine-4-one hydrochloride

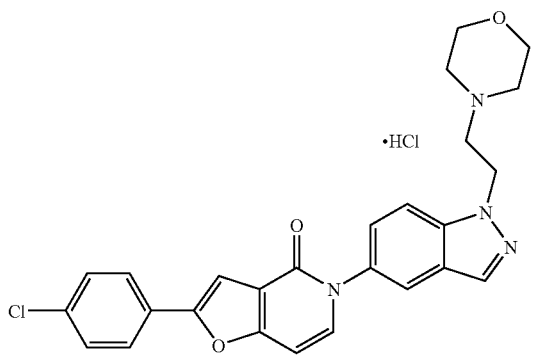

Chemical Formula: $C_{26}H_{24}Cl_2N_4O_3$
Exact Mass: 510.12
Molecular Weight: 511.40

Following the procedure of Example 3 (step e), but substituting 2-(4-chlorophenyl)-5-(1-(2-morpholinoethyl)-1H-indazol-5-yl)furo[3,2-c]pyridine-4-one for (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (34.2 mg, 86%) was prepared as a brown-yellow powder: mp 260-268° C. decompose; $^1$H NMR (500 MHz, DMSO-$d_6$) δ 10.22 (br s, 1H), 8.28 (s, 1H), 7.93-7.90 (m, 4H), 7.69 (d, J=7.5 Hz, 1H), 7.63 (s, 1H), 7.58-7.53 (m, 3H), 6.91 (d, J=7.5 Hz, 1H), 4.93 (br m, 2H), 4.02-4.00 (br m, 2H), 3.71 (br m, 4H), 3.57-3.55 (m, 2H), 3.27-3.22 (m, 2H); ESI MS m/z 475 [M+H]$^+$; HPLC (Method A) 98.0% (AUC), $t_R$=15.6 min.

Example 28

Preparation of 2-(4-Chlorophenyl)-5-(1-(2-piperazin-1-yl)ethyl)-1H-indazol-5-yl)furo[3,2-c]pyridine-4-one hydrochloride a) tert-Butyl-4-(2-(5-(2-(4-chlorophenyl)-4-oxofuro[3,2-c]pyridin-5-(4H)-yl)-1H-indazol-1-yl)ethyl)piperazine-1-carboxylate

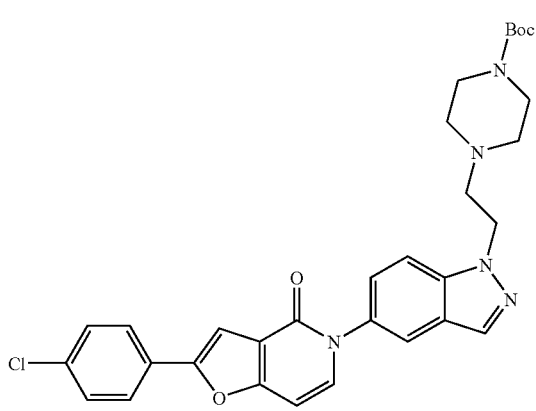

Chemical Formula: $C_{31}H_{32}ClN_5O_4$
Exact Mass: 573.21
Molecular Weight: 574.07

Following the procedure of Example 3 (step d), but substituting tert-butyl-1-piperazinecarboxylate for (R)-2-hydroxymethylpyrrolidine, the title compound (83.7 mg, 56%) was prepared as a light yellow powder: $^1$H NMR (500 MHz, CDCl$_3$) δ 8.04 (d, J=1.0 Hz, 1H), 7.73-7.72 (m, 3H), 7.54 (d, J=9.0 Hz, 1H), 7.47-7.42 (m, 3H), 7.36 (d, J=7.5 Hz, 1H), 7.25 (s, 1H), 6.68 (d, J=7.5 Hz, 1H), 4.55 (t, J=70 Hz, 2H), 3.41-3.40 (m, 4H), 2.91 (t, J=7.0 Hz, 2H), 2.47 (br m, 4H), 1.45 (s, 9H).

b) 2-(4-Chlorophenyl)-5-(1-(2-piperazin-1-yl)ethyl)-1H-indazol-5-yl)furo[3,2-c]pyridine-4-one

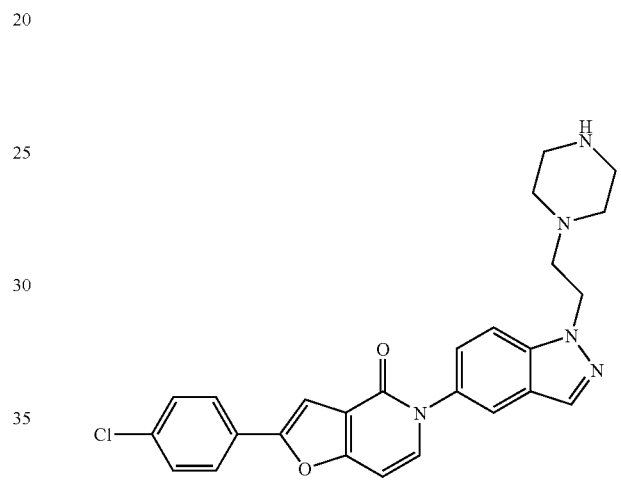

Chemical Formula: $C_{26}H_{24}ClN_5O_2$
Exact Mass: 473.16
Molecular Weight: 473.95

A solution of tert-butyl-4-(2-(5-(2-(4-chlorophenyl)-4-oxofuro[3,2-c]pyridin-5-(4H)-yl)-1H-indazol-1-yl)ethyl)piperazine-1-carboxylate (76 mg, 0.13 mmol) in CH$_2$Cl$_2$ (1.0 mL) was treated with trifluoroacetic acid (1.0 mL). The solution was stirred at ambient temperature for 1 h, and then the solution was concentrated. The resulting film was diluted with CH$_2$Cl$_2$ (5 mL) and neutralized with a saturated solution of NaHCO$_3$. The aqueous layer was extracted with CH$_2$Cl$_2$ (3×20 mL). The organic extracts were washed with brine (2×10 mL), dried (Na$_2$SO$_4$), filtered and concentrated to yield the title compound (32.0 mg, 51%) as an orange-yellow solid: $^1$H NMR (500 MHz, CDCl$_3$) δ 8.05 (s, 1H), 7.80-7.72 (m, 3H), 7.56 (d, J=9.0 Hz, 1H), 7.48-7.39 (m, 3H), 7.36 (d, J=7.5 Hz, 1H), 7.26 (s, 1H), 6.68 (d, J=7.5 Hz, 1H), 4.56 (t, J=7.0 Hz, 2H), 2.91-2.88 (m, 6H), 2.51 (br m, 4H), ESI MS m/z 474 [M+H]$^+$; HPLC (Method A) 96.5% (AUC), $t_R$=14.3 min.

c) 2-(4-chlorophenyl)-5-(1-(2-piperazin-1-yl)ethyl)-1H-indazol-5-yl)furo[3,2-c]pyridine-4-one hydrochloride

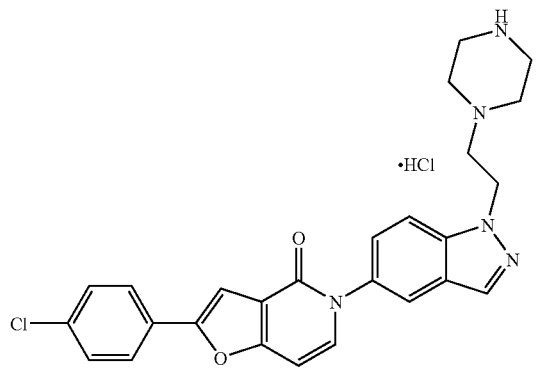

Chemical Formula: C$_{26}$H$_{25}$Cl$_2$N$_5$O$_2$
Exact Mass: 509.14
Molecular Weight: 510.42

Following the procedure of Example 3 (step e), but substituting 2-(4-chlorophenyl)-5-(1-(2-piperazin-1-yl)ethyl)-1H-indazol-5-yl)furo[3,2-c]pyridine-4-one hydrochloride for (R)-2-(4-chlorophenyl)-5-(1-(2-(2-hydroxymethyl)pyrrolidin-1-yl)ethyl)-1H-indazol-5-yl)furo[3,2-c]pyridine-4-one, the title compound (27.0 mg, 78%) was prepared as an orange-yellow powder: mp 298-300° C. decompose; $^1$H NMR (500 MHz, DMSO-d$_6$) δ 8.59 (br s, 2H), 8.18 (s, 1H), 7.92 (d, J=8.5 Hz, 2H), 7.86-7.84 (m, 2H), 7.70 (d, J=7.5 Hz, 1H), 7.64 (s, 1H), 7.57 (d, J=8.5 Hz, 2H), 7.45 d, J=10.0 Hz, 1H), 6.91 (d, J=7.5 Hz, 1H), 4.63 (br s, 2H), 3.05-2.81 (m, 6H), 2.70-2.58 (m, 4H); ESI MS m/z 474 [M+H]$^+$; HPLC (Method A) 96.7% (AUC), t$_R$=14.6 min.

Binding Assay for Human Melanin-Concentrating Hormone (MCH$_1$) Receptor

Evaluation of the affinity of compounds for the human MCH$_1$ receptor was accomplished in transfected Chinese Hamster Ovary (CHO) cells determined in a radioligand binding assay, as described in MacDonald et al., "Molecular characterization of the melanin-concentrating hormone/receptor complex: identification of critical residues involved in binding and activation", Mol. Pharmacol., 58:217 (2000). Cell membrane homogenates (5 μg protein) were incubated for 60 min at 22° C. with 0.1 nM [$^{125}$I][Phe$^{13}$,Tyr$^{19}$]-MCH in the absence or presence of the test compound in a buffer containing 25 mM Hepes/Tris (pH 7.4), 5 mM MgCl$_2$, 1 mM CaCl$_2$ and 0.5% bovine serum albumin (BSA). Nonspecific binding was determined in the presence of 0.1 μM MCH. Following incubation, the samples were filtered rapidly under vacuum through glass fiber filters (GF/B, Packard) and rinsed several times with an ice-cold buffer containing 25 mM Hepes/Tris (pH 7.4), 500 mM NaCl, 5 mM MgCl$_2$, 1 mM CaCl$_2$ and 0.1% BSA using a 96-sample cell harvester (Unifilter, Packard). The filters were dried, then counted for radioactivity in a scintillation counter (Topcount, Packard) using a scintillation cocktail (Microscint 0, Packard).

The results are expressed as a percent inhibition of the control radioligand specific binding. The IC$_{50}$ value (concentration causing a half-maximal inhibition of control specific binding) and Hill coefficient (n$_H$) were determined by non-linear regression analysis of the competition curve using Hill equation curve fitting. The inhibition constant (K$_i$) was calculated from the Cheng Prusoff equation:

$$(K_i = IC_{50}/(1+(L/K_D))),$$

where L=concentration of radioligand in the assay, and K$_D$=affinity of the radioligand for the receptor).

By methods described above, the compounds listed in Table 1 were synthesized and tested for biological activity. All of the compounds in Table 1 exhibited K$_i$ of less than or equal to 2.0 μM in the MCH$_1$ binding assay.

TABLE 1

| Ex. No. | Structure | Mass Spec | $^1$H NMR Data |
|---|---|---|---|
| 1 | 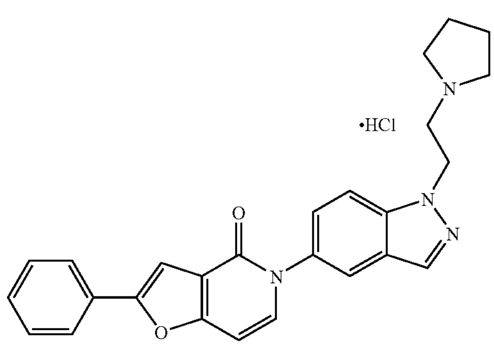 | 425 | $^1$H NMR (500 MHz, DMSO-d$_6$) δ 10.07 (bs, 0.5H), 8.28 (s, 1H), 7.92-7.89 (m, 4H), 7.66 (d, J = 7.5 Hz, 1H), 7.56-7.48 (m, 4H), 7.40 (t, J = 7.5 Hz, 1H), 6.91 (d, J = 7.5 Hz, 1H), 4.87 (t, J = 6.0 Hz, 2H), 3.77-3.73 (m, 2H), 3.56-3.55 (m. 2H), 3.09-3.06 (m, 2H), 2.01 (br m, 2H), 1.89-1.84 (br m, 2H) |

TABLE 1-continued

| Ex. No. | Structure | Mass Spec | ¹H NMR Data |
|---|---|---|---|
| 2 | 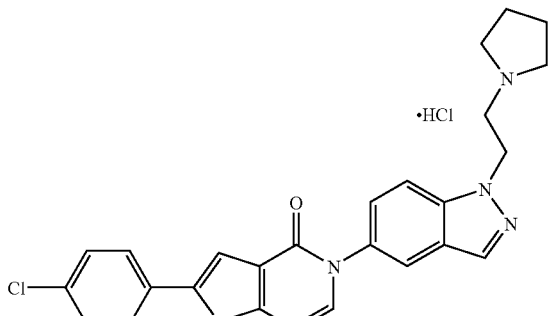 | 459 | ¹H NMR (500 MHz, DMSO-d₆) δ 9.81 (br s, 0.5H), 8.28 (s, 1H), 7.92-7.89 (m, 4H), 7.68 (d, J = 7.5 Hz, 1H), 7.63 (s, 1H), 7.56 (d, J = 8.5 Hz, 2H), 7.53 (dd, J = 9.0, 1.5 Hz, 1H), 6.91 (d, J = 7.5 Hz, 1H), 4.86 (t. J = 6.0 Hz, 2H), 3.76 (t, J = 6.0 Hz, 2H), 3.57-3.56 (m, 2H), 3.11-3.07 (m, 2H), 2.01 (br m, 2H), 1.87-1.84 (br m, 2H) |
| 3 | 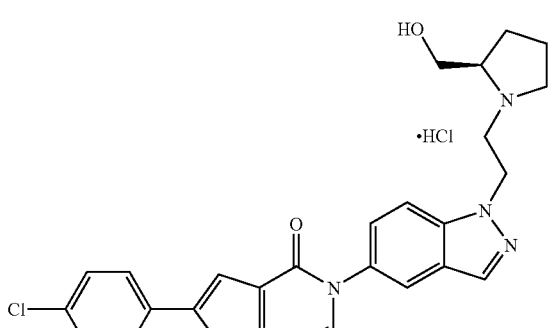 | 489 | ¹H NMR (500 MHz, DMSO-d₆) δ 9.77 (br s, 1H), 8.25 (s, 1H), 7.92-7.89 (m, 4H), 7.69 (d, J = 7.5 Hz, 1H), 7.63 (s, 1H), 7.57-7.51 (m, 3H), 6.91 (d, J = 7.5 Hz, 1H), 5.52-5.51 (m, 1H), 4.94-4.85 (m, 2H), 3.96-3.94 (m, 1H), 3.81-3.78 (m, 1H), 3.71-3.65 (m, 3H), 3.57-3.35 (m, 1H), 3.18-3.13 (m, 1H), 2.11-1.98 (m, 2H), 1.88-1.72 (m, 2H) |
| 4 | 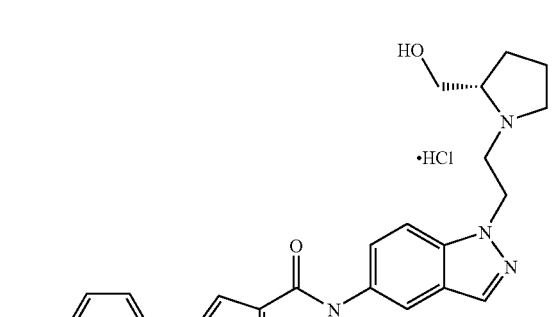 | 489 | ¹H NMR (500 MHz, DMSO-d₆) δ 9.62 (br s, 1H), 8.27 (s, 1H), 7.92-7.88 (m, 4H), 7.68 (d, J = 7.5 Hz, 1H), 7.63 (s, 1H), 7.57-7.52 (m, 3H), 6.91 (d, J = 7.5 Hz, 1H), 5.54-5.53 (m, 1H), 4.93-4.84 (m, 2H), 3.96-3.94 (m, 1H), 3 81-3.78 (m, 1H), 3.70-3.65 (m, 3H), 3.57-3.56 (m, 1H), 3.17-3.14 (m, 1H), 2.12-1.99 (m, 2H), 1.88-1.72 (m, 2H) |
| 5 | 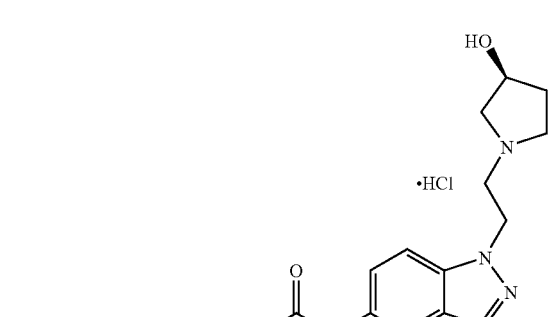 | 475 | ¹H NMR (500 MHz, DMSO-d₆) δ 10.24 (br s, 1H), 8.28-8.27 (m, 1H), 7.92-7.87 (m, 4H), 7.68 (d, J = 7.5 Hz, 1H), 7.55 (dd, J = 7.0, 2.0 Hz, 2H), 7.52 (d, J = 9.0 Hz, 1H), 6.90 (d, J = 7.5 Hz, 1H), 5.48 (s, 1H), 4.88-4.87 (m, 2H), 4.44-4.37 (m, 1H), 3.80-3.61 (m, 3H), 3.41 (br s, 1H), 3.15-3.00 (m, 2H), 2.23 (br s, 1H), 1.96-1.82 (m, 2H) |

TABLE 1-continued

| Ex. No. | Structure | Mass Spec | ¹H NMR Data |
|---|---|---|---|
| 6 | 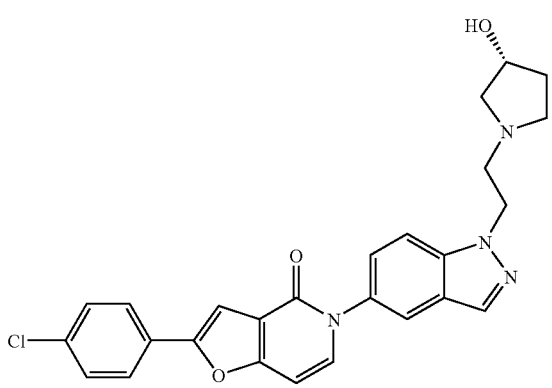 | 475 | Free Base ¹H MNR (300 MHz, CDCl₃) δ 8.05 (s, 1H), 7.74-7.54 (m, 5H), 7.44-7.41 (m, 3H), 7.36 (d, J = 7.8 Hz, 1H), 6.67 (d, J = 7.2 Hz, 1H), 4.57 (t, J = 6.9 Hz, 2H), 4.32 (s, 1H), 3.04 (t, J = 6.9 Hz, 2H), 3.00-2.93 (m, 1H), 2.74 (d, J = 9.9 Hz, 1H), 2.58-2.53 (m, 1H), 2.40-2.32 (m, 1H), 2.20-2.12 (m, 1H), 1.86-1.71 (m, 2H) |
| 7 | 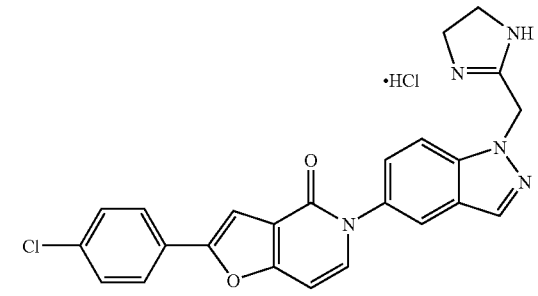 | 444 | ¹H NMR (500 MHz, DMSO-d₆) δ 10.14 (br s, 2H), 8.33 (s, 1H), 7.92-7.87 (m, 4H), 7.66 (d, J = 7.5 Hz, 1H), 7.63 (s, 1H), 7.57-7.54 (m, 3H), 6.92 (d, J = 7.5 Hz, 1H), 5.69 (s, 2H), 3.86 (s, 4H) |
| 8 | 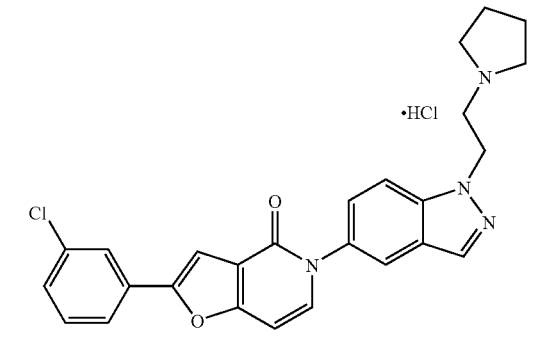 | 459 | ¹H NMR (500 MHz, DMSO-d₆) δ 9.97 (br s, 1H), 8.24 (s, 1H), 7.96 (t, J = 2.0 Hz, 1H), 7.92-7.85 (m, 3H), 7.71 (s, 1H), 7.69 (d, J = 7.5 Hz, 1H), 7.54-7.51 (m, 2H), 7.45 (dd, J = 8.0, 1.5 Hz, 1H), 6.92 (d, J = 8.0 Hz, 1H), 4.87 (t, J = 6.0 Hz, 2H), 3.75-3.74 (m, 2H), 3.55 (br, 2H), 3.08 (br, 2H), 2.01 (br, 2H), 1.85-1.84 (br, 2H) |
| 9 | 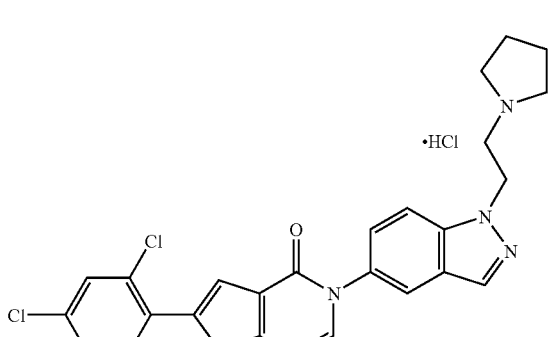 | 493 | ¹H NMR (500 MHz, DMSO-d₆) δ 9.74-9.82 (br s, 1H, NH), 8.29 (s, 1H), 7.99 (d, J = 8.5 Hz, 1H) 7.92-7.87 (m, 2H), 7.84 (d, J = 2.0 Hz, 1H), 7.74 (d, J = 7.5 Hz, 1H), 7.63 (dd, J = 8.5, 2.0 Hz, 1H) 7.59 (s, 1H), 7.53 (br d, J = 9.5 Hz, 1H), 6.94 (d, J = 7.5 Hz, 1H), 4.87 (t, J = 5.5 Hz, 2H), 3.80-3.70 (m, 2H), 3.61-3.52 (m, 2H), 3.15-3.02 (m, 2H), 2.08-1.92 (m, 2H), 1.90-1.79 (m, 2H) |

TABLE 1-continued

| Ex. No. | Structure | Mass Spec | $^1$H NMR Data |
|---|---|---|---|
| 10 | (structure with 4-chloro-2-methoxyphenyl furopyridinone linked to indazole-N-ethyl-pyrrolidine · HCl) | 489 | $^1$H NMR (500 MHz, DMSO-d$_6$) δ 10.15-10.01 (br s, 1H, NH), 8.28 (s, 1H), 7.94-7.85 (m, 3H), 7.69 (d, J = 7.2 Hz, 1H), 7.52 (dd, J = 6.7, 1.8 Hz, 1H), 7.36 (s, 1H), 7.31 (d, J = 1.8 Hz, 1H), 7.19 (dd, J = 8.4, 1.8 Hz, 1H), 6.91 (d, J = 7.2 Hz, 1H), 4.88 (t, J = 6.0 Hz, 2H), 4.03 (s, 3H), 3.78-3.70 (m, 2H), 3.62-3.50 (m, 2H), 3.14-3.00 (m, 2H), 2.08-1.96 (m, 2H), 1.90-1.80 (m, 2H) |
| 11 | (structure with 2-chlorophenyl furopyridinone linked to indazole-N-ethyl-pyrrolidine · HCl) | 459 | $^1$H NMR (500 MHz, DMSO-d$_6$) δ 9.90-9.80 (br s, 1H, NH), 8.29 (s, 1H), 7.98 (dd, J = 8.0, 1.5 Hz, 1H), 7.93-7.89 (m, 2H), 7.73 (d, J = 7.3 Hz, 1H), 7.66 (dd, J = 8.0, 1.5 Hz, 1H), 7.57-7.51 (m, 3H), 7.46 (ddd, J = 8.0, 8.0, 1.5 Hz, 1H), 6.94 (d, J = 7.3 Hz, 1H), 4.87 (t, J = 6.0 Hz, 2H), 3.79-3.72 (m, 2H), 3.60-3.52 (m, 2H), 3.13-3.02 (m, 2H), 2.08-1.97 (m, 2H), 1 90-1.81 (m, 2H) |
| 12 | (structure with 4-fluoro-2-cyanophenyl furopyridinone linked to indazole-N-ethyl-pyrrolidine · HCl) | 468 | $^1$H NMR (500 MHz, DMSO-d$_6$) δ 8.29 (s, 1H), 8.13 (dd, J = 8.8, 5.5 Hz, 1H), 8.07 (dd, J = 8.8, 2.5 Hz, 1H), 7.94-7.89 (m, 2H), 7.79 (dd, J = 8.5, 2.5 Hz, 1H), 7.76 (d, J = 7.5 Hz, 1H), 7.69 (s, 1H), 7.54 (dd, J = 9.0, 1.5 Hz, 1H), 6.94 (d, J = 7.5 Hz, 1H), 4.90-4.82 (m, 2H), 3.81-3.71 (m, 2H), 3.63-3.50 (m, 2H), 3.15-3.03 (m, 2H), 2.08-1.97 (m, 2H), 1.92-1.80 (m, 2H) |
| 13 | (structure with 2-chloro-4-fluorophenyl furopyridinone linked to indazole-N-ethyl-pyrrolidine · HCl) | 477 | $^1$H NMR (500 MHz, DMSO-d$_6$) δ 10.20-10.10 (br s, 1H, NH), 8.29 (s, 1H), 8.01 (dd, J = 8.3, 6.0 Hz, 1H), 7.92 (d, J = 9.0 Hz, 1H), 7.90 (d, J = 1.8 Hz, 1H), 7.71 (d, J = 6.5 Hz, 1H), 7.68 (dd, J = 9.0, 2.8 Hz, 1H), 7.53 (dd, J = 9.0, 1.8 Hz, 1H), 7.51 (s, 1H), 7.44 (ddd, J = 8.3, 8.0, 2.8 Hz, 1H), 6.93 (d, J = 6.5 Hz, 1H), 4.89 (t, J = 6.3 Hz, 2H), 3.76-3.70 (m, 2H), 3.58-3.52 (m, 2H), 3.10-3.02 (m, 2H), 2.05-1.98 (m, 2H), 1.90-1.81 (m, 2H) |

TABLE 1-continued

| Ex. No. | Structure | Mass Spec | $^1$H NMR Data |
|---|---|---|---|
| 14 | (structure: 2-(4-chloro-2-fluorophenyl)-5-(1-(2-(pyrrolidin-1-yl)ethyl)-1H-indazol-5-yl)furo[3,2-c]pyridin-4(5H)-one · HCl) | 477 | $^1$H NMR (500 MHz, DMSO-d$_6$) δ 10.12-10.05 (br s, 1H, NH), 8.28 (s, 1H), 7.96 (dd, J = 8.5, 8.5 Hz, 1H), 7.94-7.88 (m, 2H), 7.74 (d, J = 7.5 Hz, 1H), 7.68 (d, J = 11.0 Hz, 1H), 7.52 (br d, J = 8.5 Hz, 1H), 7.48 (d, J = 8.5 Hz, 1H), 7.36 (s, 1H), 6.94 (d, J = 7.5 Hz, 1H), 4.92-4.80 (m, 2H), 3.80-3.71 (m, 2H), 3.60-3.49 (m, 2H), 3.13-3.01 (m, 2H), 2.07-1.92 (m, 2H), 1.90-1.80 (m, 2H) |
| 15 | (structure: 2-(4-fluorophenyl)-5-(1-(2-(pyrrolidin-1-yl)ethyl)-1H-indazol-5-yl)furo[3,2-c]pyridin-4(5H)-one · HCl) | 443 | $^1$H NMR (500 MHz, DMSO-d$_6$) δ 9.90-9.82 (br s, 1H, NH), 8.28 (s, 1H), 7.95 (dd, J = 9.0, 5.0 Hz, 2H), 7.92-7.89 (m, 2H), 7.67 (d, J = 7.5 Hz, 1H), 7.56 (s, 1H), 7.53 (br d, J = 9.0 Hz, 1H), 7.36 (dd, J = 9.0, 9.0 Hz, 2H), 6.91 (d, J = 7.5 Hz, 1H), 4.91-4.83 (m, 2H), 3.80-3.72 (m, 2H), 3.63-3.51 (m, 2H), 3.14-3.05 (m, 2H), 2.09-1.98 (m, 2H), 1.90-1.80 (m, 2H) |
| 16 | (structure: 5-(1-(2-(pyrrolidin-1-yl)ethyl)-1H-indazol-5-yl)-2-(4-(trifluoromethyl)phenyl)furo[3,2-c]pyridin-4(5H)-one · HCl) | 493 | $^1$H NMR (500 MHz, DMSO-d$_6$) δ 9.79-9.68 (br s, 1H, NH), 8.29 (s, 1H), 8.12 (d, J = 8.0 Hz, 2H), 7.94-7.88 (m, 2H), 7.86 (d, J = 8.0 Hz, 2H), 7.81 (s, 1H), 7.73 (d, J = 7.0 Hz, 1H), 7.56-7.51 (m, 1H), 6.95 (d, J = 7.0 Hz, 1H), 4.90-4.82 (m, 2H), 3.79-3.71 (m, 2H), 3.62-3.53 (m, 2H), 3.15-3.04 (m, 2H), 2.09-1.99 (m, 2H), 1.93-1.81 (m, 2H) |
| 17 | (structure: 2-(5-chloropyridin-2-yl)-5-(1-(2-(pyrrolidin-1-yl)ethyl)-1H-indazol-5-yl)furo[3,2-c]pyridin-4(5H)-one · HCl) | 460 | $^1$H NMR (500 MHz, DMSO-d$_6$) δ 9.72-9.60 (br s, 1H, NH), 8.72 (d, J = 2.5 Hz, 1H), 8.28 (s, 1H), 8.08 (dd, J = 8.5, 2.5 Hz, 1H), 7.98 (d, J = 8.5 Hz, 1H), 7.94-7.89 (m, 2H), 7.74 (d, J = 7.5 Hz, 1H), 7.65 (s, 1H), 7.54 (br d, J = 8.0 Hz, 1H), 6.95 (d, J = 7.5 Hz, 1H), 4.90-4.82 (m, 2H), 3.80-3.73 (m, 2H), 3.63-3.51 (m, 2H), 3.14-3.03 (m, 2H), 2.07-1.95 (m, 2H), 1.91-1.82 (m, 2H) |
| 18 | (structure: 2-(2-fluorophenyl)-5-(1-(2-(pyrrolidin-1-yl)ethyl)-1H-indazol-5-yl)furo[3,2-c]pyridin-4(5H)-one · HCl) | 443 | $^1$H-NMR (500 MHz, DMSO-d$_6$) δ 10.10-9.92 (br s, 1H, NH), 8.29 (s, 1H), 7.96 (ddd, J = 8.0, 8.0, 2.0 Hz, 1H), 7.94-7.89 (m, 2H), 7.72 (d, J = 7.5 Hz, 1H), 7.54 (dd, J = 8.0, 1.5 Hz, 1H), 7.51-7.46 (m, 1H), 7.45-7.37 (m, 2H), 7.30 (d, J = 3.0 Hz, 1H), 6.95 (d, J = 7.5 Hz, 1H), 4.88 (t, J = 6.0 Hz, 2H), 3.78-3.72 (m, 2H), 3.60-3.51 (m, 2H), 3.12-3.03 (m, 2H), 2.06-1.97 (m, 2H), 1.91-1.80 (m, 2H) |

TABLE 1-continued

| Ex. No. | Structure | Mass Spec | ¹H NMR Data |
|---|---|---|---|
| 19 | 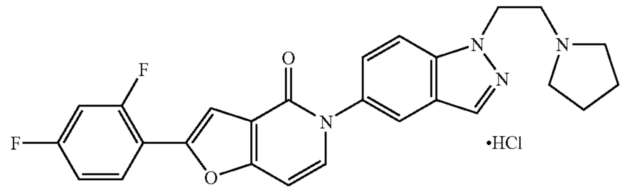 | 461 | ¹H NMR (500 MHz, DMSO-d$_6$) δ 10.15-9.90 (br s, 1H, NH), 8.29 (s, 1H), 8.03-7.96 (m, 1H), 7.94-7.88 (m, 2H), 7.72 (d, J = 7.5 Hz, 1H), 7.53 (dd, J = 9.0, 1.5 Hz, 1H), 7.52 (ddd, J = 9.5, 9.5, 2.5 Hz, 1H), 7.30 (ddd, J = 8.5, 8.5, 2.5 Hz, 1H), 7.28 (d, J = 3.0 Hz, 1H), 6.94 (d, J = 7.5 Hz, 1H), 4.88 (t, J = 6.0 Hz, 2H), 3.78-3.70 (m, 2H), 3.59-3.51 (m, 2H), 3.12-3.01 (m, 2H), 2.06-1.97 (m, 2H), 1.90-1.80 (m, 2H) |
| 20 | 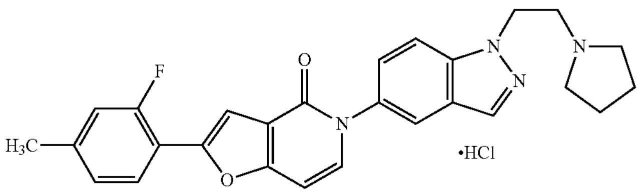 | 457 | ¹H-NMR (500 MHz, DMSO-d$_6$) δ 10.15-10.06 (br s, 1H, NH), 8.28 (s, 1H), 7.92 (d, J = 9.0 Hz, 1H), 7.90 (d, J = 2.0 Hz, 1H), 7.83 (dd, J = 8.0, 8.0 Hz, 1H), 7.70 (d, J = 7.5 Hz, 1H), 7.53 (dd, J = 9.0, 2.0 Hz, 1H), 7.26 (d, J = 12.5 Hz, 1H), 7.23-7.18 (m, 2H), 6.93 (d, J = 7.5 Hz, 1H), 4.88 (t, J = 6.0 Hz, 2H), 3.78-3.72 (m, 2H), 3.60-3.52 (m, 2H), 3.12-3.03 (m, 2H), 2.39 (s, 3H), 2.07-1.98 (m, 2H), 1.90-1.81 (m, 2H) |
| 21 | 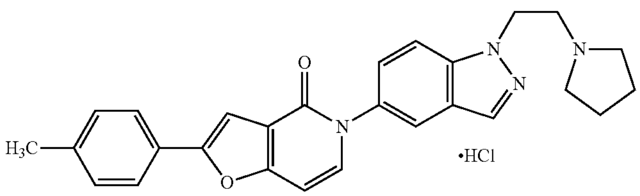 | 439 | ¹H NMR (500 MHz, DMSO-d$_6$) δ 10.12-9.99 (br s, 1H, NH), 8.26 (br s, 1H), 7.92-7.75 (m, 2H), 7.79 (d, J = 8.0 Hz, 2H), 7.65 (d, J = 7.0 Hz, 1H), 7.51 (br d, J = 7.5 Hz, 1H), 7.47 (s, 1H), 7.31 (d, J = 8.0 Hz, 2H), 6.90 (d, J = 7.5 Hz, 1H), 4.91-4.79 (m, 2H), 3.81-3.68 (m, 2H), 3.67-3.45 (m, 2H), 3.15-2.97 (m, 2H), 2.50 (s, 3H), 2.11-1.98 (m, 2H), 1.95-1.79 (m, 2H) |
| 22 | 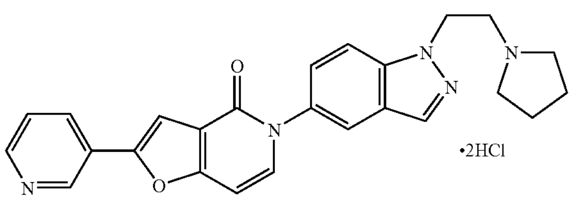 | 426 | ¹H NMR (500 MHz, DMSO-d$_6$) δ 10.33-10.22 (br s, 1H, NH), 9.15 (s, 1H), 8.60 (d, J = 4.5 Hz, 1H), 8.32-8.27 (m, 2H), 7.93 (d, J = 9.0 Hz, 1H), 7.91 (s, 1H), 7.77 (s, 1H), 7.72 (d, J = 7.3 Hz, 1H), 7.57 (dd, J = 8.0, 4.8 Hz, 1H), 7.53 (br d, J = 9.0 Hz, 1H), 6.94 (d, J = 7.3 Hz, 1H), 4.90 (t, J = 6.0 Hz, 2H), 3.75-3.70 (m, 2H), 3.60-3.48 (m, 2H), 3.10-3.01 (m, 2H), 2.05-1.95 (m, 2H), 1.90-1.79 (m, 2H) |
| 23 | 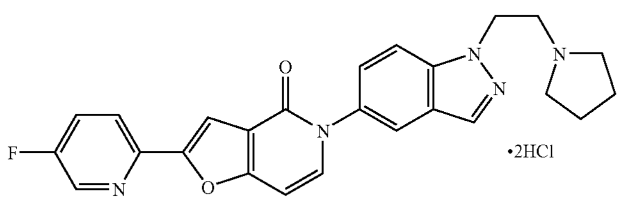 | 444 | ¹H NMR (500 MHz, DMSO-d$_6$) δ 10.27-10.19 (br s, 1H, NH), 8.68 (d, J = 2.5 Hz, 1H), 8.28 (s, 1H), 8.04 (dd, J = 9.0, 4.5 Hz, 1H), 7.94-7.87 (m, 3H), 7.73 (d, J = 7.5 Hz, 1H), 7.58 (s, 1H), 7.54 (dd, J = 9.0, 1.5 Hz, 1H), 6.94 (d, J = 7.5 Hz, 1H), 4.89 (t, J = 6.0 Hz, 2H), 3.78-3.71 (m, 2H), 3.65-3.49 (m, 2H), 3.11-3.02 (m, 2H), 2.06-1.95 (m, 2H), 1.89-1.81 (m, 2H) |
| 24 | 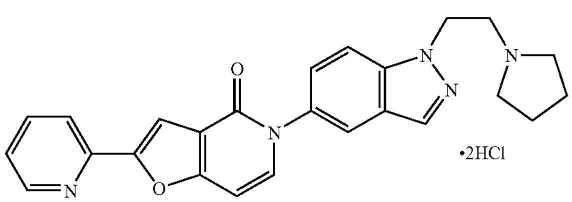 | 426 | ¹H NMR (500 MHz, DMSO-d$_6$) δ 10.15-10.04 (br s, 1H, NH), 8.69-8.65 (m, 1H), 8.28 (d, J = 2.0 Hz, 1H), 7.98-7.88 (m, 4H), 7.75-7.71 (m, 1H), 7.59 (d, J = 2.5 Hz, 1H), 7.56-7.52 (m, 1H), 7.43-7.38 (m, 1H), 6.95 (dd, J = 7.5, 2.0 Hz, 1H), 4.92-4.85 (m, 2H), 3.78-3.71 (m, 2H), 3.59-3.52 (m, 2H), 3.12-3.03 (m, 2H), 2.07-1.98 (m, 2H), 1.90-1.81 (m, 2H) |
| 25 | 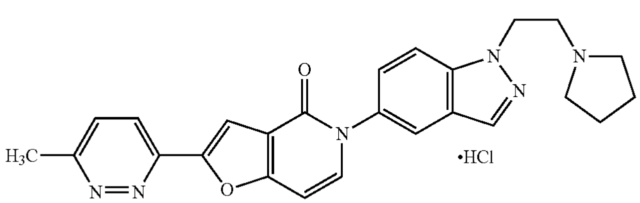 | 441 | ¹H NMR (500 MHz, DMSO-d$_6$) δ 10.32-10.11 (br s, 1H, NH), 8.29 (s, 1H), 8.14 (d, J = 9.0 Hz, 1H), 7.96-7.91 (m, 2H), 7.83 (s, 1H), 7.77 (d, J = 7.3 Hz, 1H), 7.72 (d, J = 9.0 Hz, 1H), 7.55 (dd, J = 8.5, 1.5 Hz, 1H), 6.98 (d, J = 7.3 Hz, 1H), 4.89 (t, J = 5.5 Hz, 2H), 3.78-3.71 (m, 2H), 3.70-3.45 (m, 2H), 3.12-3.01 (m, 2H), 2.68 (s, 3H), 2.06-1.98 (m, 2H), 1.90-1.81 (m, 2H) |

TABLE 1-continued

| Ex. No. | Structure | Mass Spec | $^1$H NMR Data |
|---|---|---|---|
| 26 | 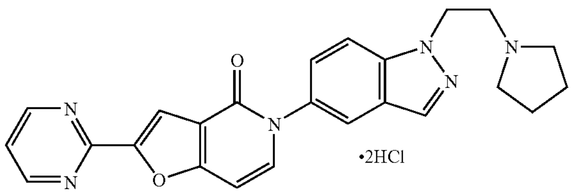 | 427 | $^1$H NMR (500 MHz, DMSO-d$_6$) δ 9.91-9.82 (br s, 1H, NH), 8.92 (d, J = 5.0 Hz, 2H), 8.29 (s, 1H), 7.95-7.90 (m, 2H), 7.79 (d, J = 7.5 Hz, 1H), 7.69 (s, 1H), 7.55 (br d, J = 9.0 Hz, 1H), 7.49 (d, J = 5.0 Hz, 1H), 6.99 (d, J = 7.5 Hz, 1H), 4.87 (t, J = 6.0 Hz, 2H), 3.80-3.71 (m, 2H), 3.62-3.53 (m, 2H), 3.15-3.04 (m, 2H), 2.07-1.96 (m, 2H), 1.92-1.81 (m, 2H) |
| 27 | 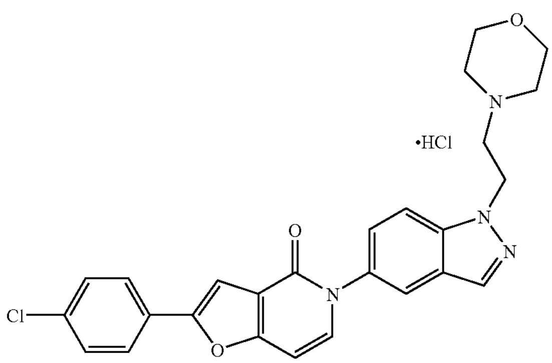 | 475 | $^1$H NMR (500 MHz, DMSO-d$_6$) δ 10.22 (br s, 1H), 8.28 (s, 1H), 7.93-7.90 (m, 4H), 7.69 (d, J = 7.5 Hz, 1H), 7.63 (s, 1H), 7.58-7.53 (m, 3H), 6.91 (d, J = 7.5 Hz, 1H), 4.93 (br m, 2H), 4.02-4.00 (br m, 2H), 3.71 (br m, 4H), 3.57-3.55 (m, 2H), 3.27-3.22 (m, 2H) |
| 28 | 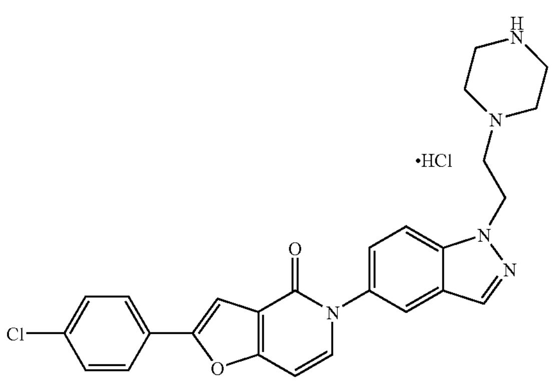 | 474 | $^1$H NMR (500 MHz, DMSO-d$_6$) δ 8.59 (br s, 2H), 8.18 (s, 1H), 7.92 (d, J = 8.5 Hz, 2H), 7.86-7.84 (m, 2H), 7.70 (d, J = 7.5 Hz, 1H), 7.64 (s, 1H), 7.57 (d, J = 8.5 Hz, 2H), 7.45 d, J = 10.0 Hz, 1H), 6.91 (d, J = 7.5 Hz, 1H), 4.63 (br s, 2H), 3.05-2.81 (m, 6H), 2.70-2.58 (m, 4H) |

The present invention is not limited to the compounds found in the above examples, and many other compounds falling within the scope of the invention may also be prepared using the procedures set forth in the above synthetic schemes. The preparation of additional compounds of formula I using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

The invention claimed is:

1. A compound of formula I:

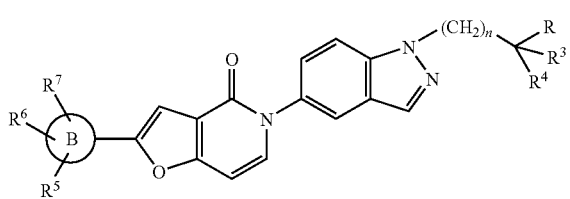

or a pharmaceutically acceptable salt form wherein
- n is 1 or 2;
- R is NR$^1$R$^2$, wherein R$^1$ and R$^2$ are each independently selected from H and optionally substituted alkyl, or R$^1$ and R$^2$, together with the N atom to which they are attached, form a 4-7 membered optionally substituted heterocyclic ring which optionally contains 1 or 2 heteroatoms in addition to the N atom shown;
- R$^3$ and R$^4$ are each independently selected from H and alkyl, or R, R$^3$ and R$^4$ may combine to form an optionally substituted imidazolin-2-yl;
- B is aryl or heteroaryl; and
- R$^5$, R$^6$, R$^7$ are each independently selected from H, —OH, —O-alkyl, alkyl, halo, —CF$_3$, and —CN;

provided that the compound is not one of the following:

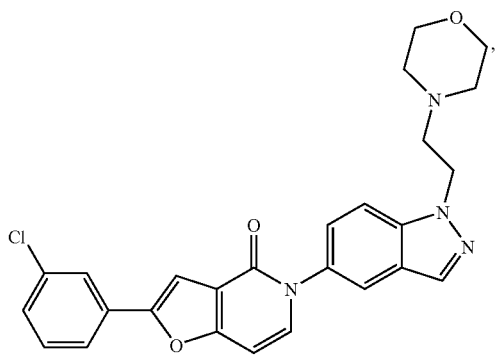

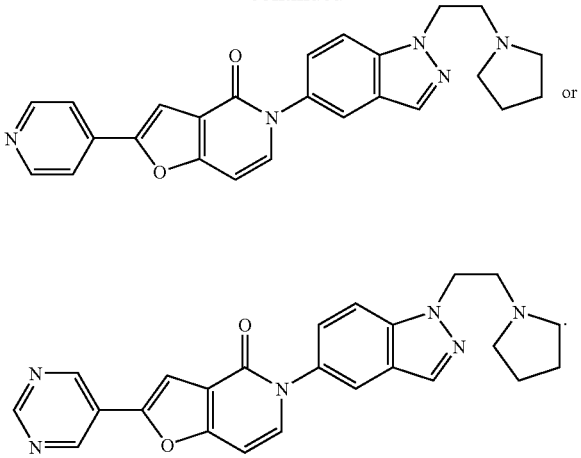

2. A compound according to claim 1, wherein R is selected from the group consisting of pyrrolidin-1-yl, 2-hydroxymethylpyrrolidin-1-yl, 3-hydroxypyrrolidin-1-yl, and morpholin-4-yl and piperazin-1-yl.

3. A compound according to claim 1, wherein R is selected from S-2-hydroxymethylpyrrolidin-1-yl, R-2-hydroxymethylpyrrolidin-1-yl, S-3-hydroxypyrrolidin-1-yl and R-3-hydroxypyrrolidin-1-yl.

4. A compound according to claim 1, wherein R$^3$ and R$^4$ are both H.

5. A compound according claim 1, wherein R, R$^3$ and R$^4$ combine to form an imidazolin-2-yl which is optionally independently substituted at each of the 1-, 4- and 5- positions with alkyl.

6. A compound according to claim 1, wherein n is 1.

7. A compound according to claim 1, wherein n is 2.

8. A compound according to claim 1, wherein B is phenyl.

9. A compound according to claim 8 wherein B, taken together with R$^5$, R$^6$ and R$^7$, is selected from the group consisting of phenyl, 4-chlorophenyl, 4-fluorophenyl, 3-chlorophenyl, 2-chlorophenyl, 4-trifluoromethylphenyl, 2-cyano-4-fluorophenyl, 2,4-dichlorophenyl, 4-chloro-2-fluorophenyl, 2-chloro-4-fluorophenyl, 4-chloro-2-methoxyphenyl, 2-fluorophenyl, 2,4-difluorophenyl, 2-fluoro-4-methylphenyl and 4-methylphenyl.

10. A compound according to claim 1, wherein B is pyridine.

11. A compound according to claim 10 wherein B, taken together with R$^5$, R$^6$ and R$^7$, is selected from the group consisting of 5-chloropyridin-2-yl, pyridin-3-yl, 5-fluoropyridin-2-yl, and pyridin-2-yl.

12. A compound according to claim 1 wherein B is pyridazine.

13. A compound according to claim 12 wherein B, taken together with R$^5$, R$^6$ and R$^7$, is 6-methylpyridazine-3-yl.

14. A compound according to claim 1 wherein B is pyrimidine.

15. A compound according to claim 14 wherein B, taken together with R$^5$, R$^6$ and R$^7$, is pyrimidin-2-yl.

16. A compound according to claim 1, wherein R$^5$, R$^6$, R$^7$ are each independently selected from H, —O-alkyl, alkyl, halo, —CF$_3$, and —CN.

17. A compound according claim 1 which is selected from the following:
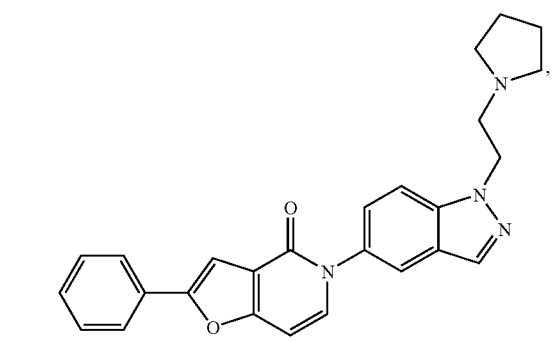
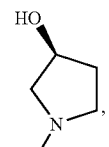
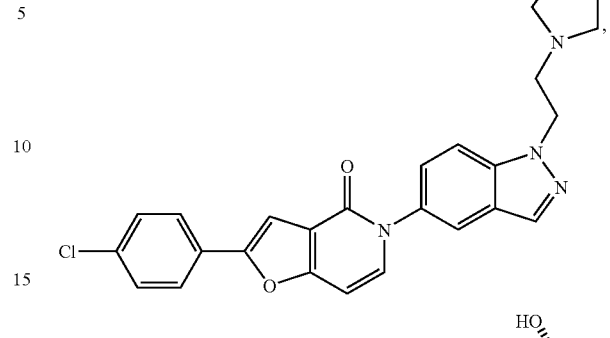
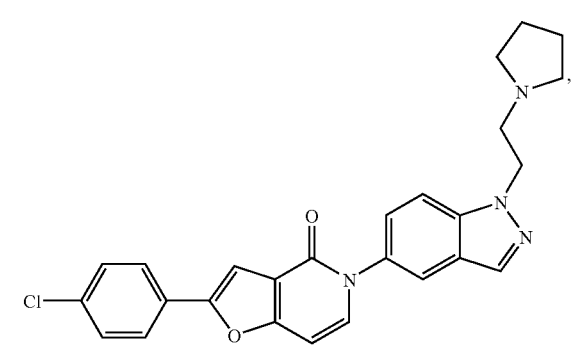
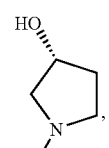
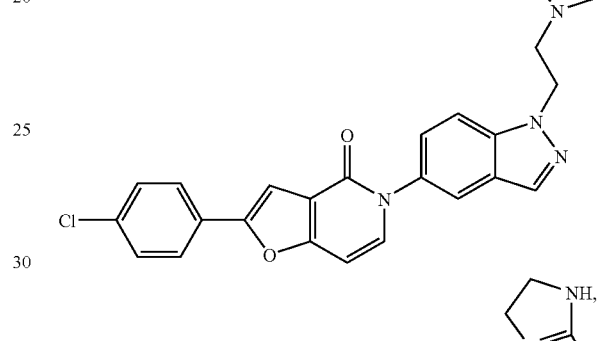
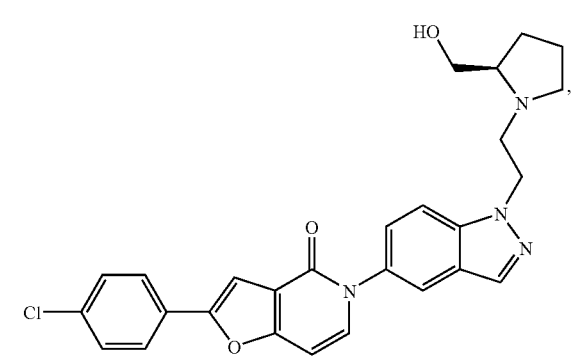
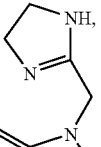
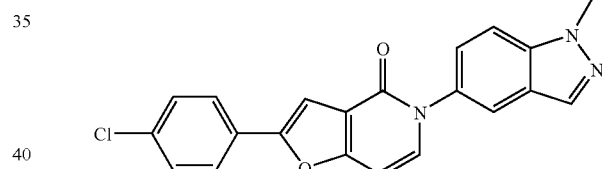
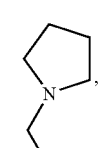
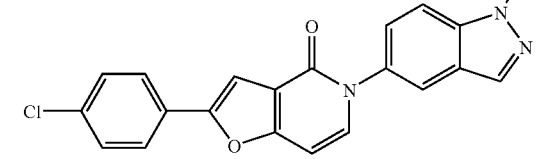
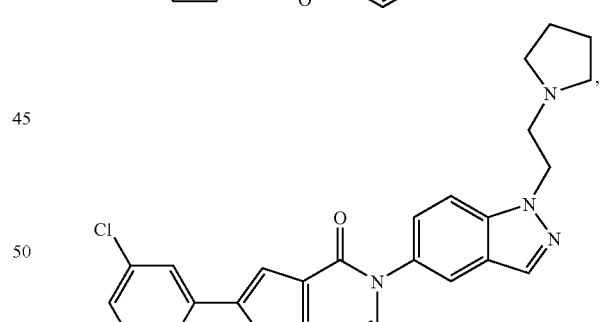
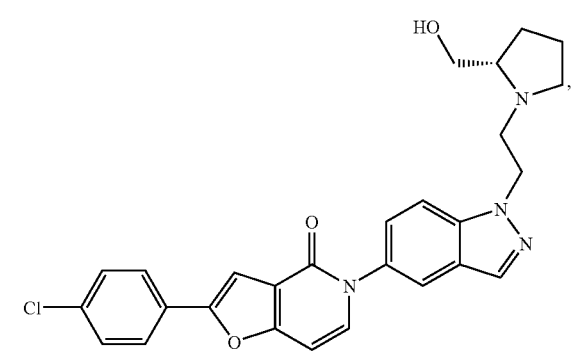
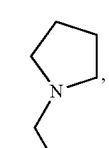
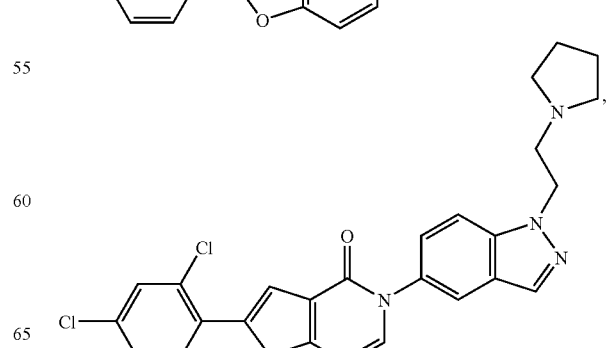

-continued
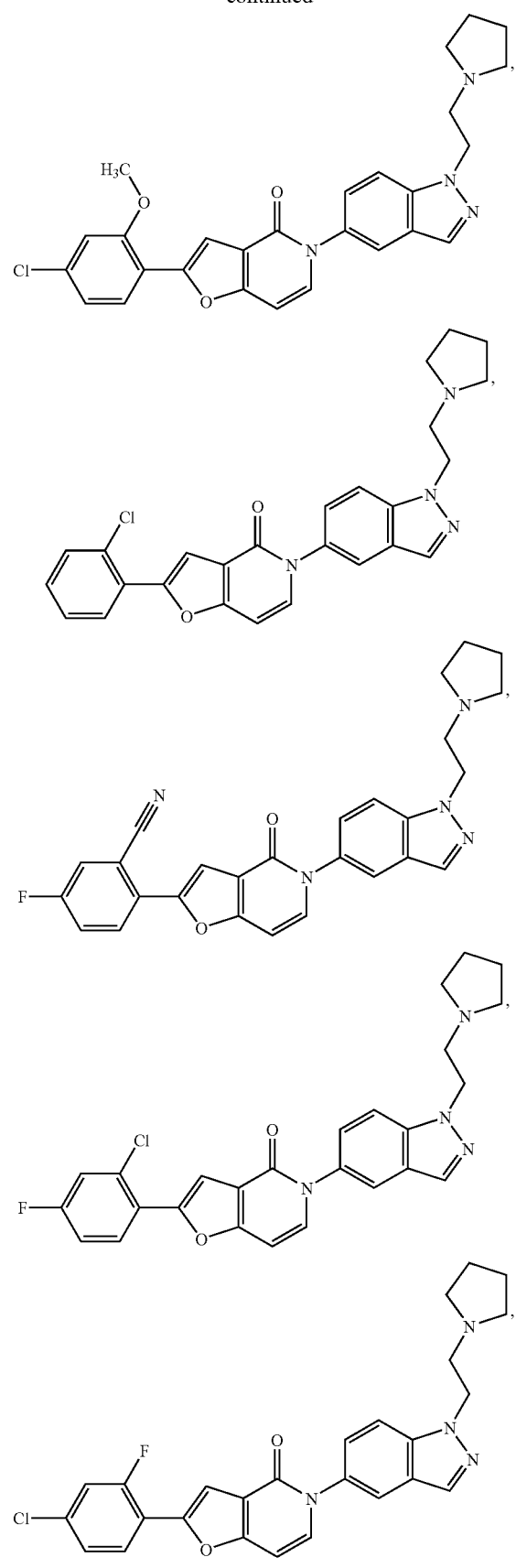
-continued
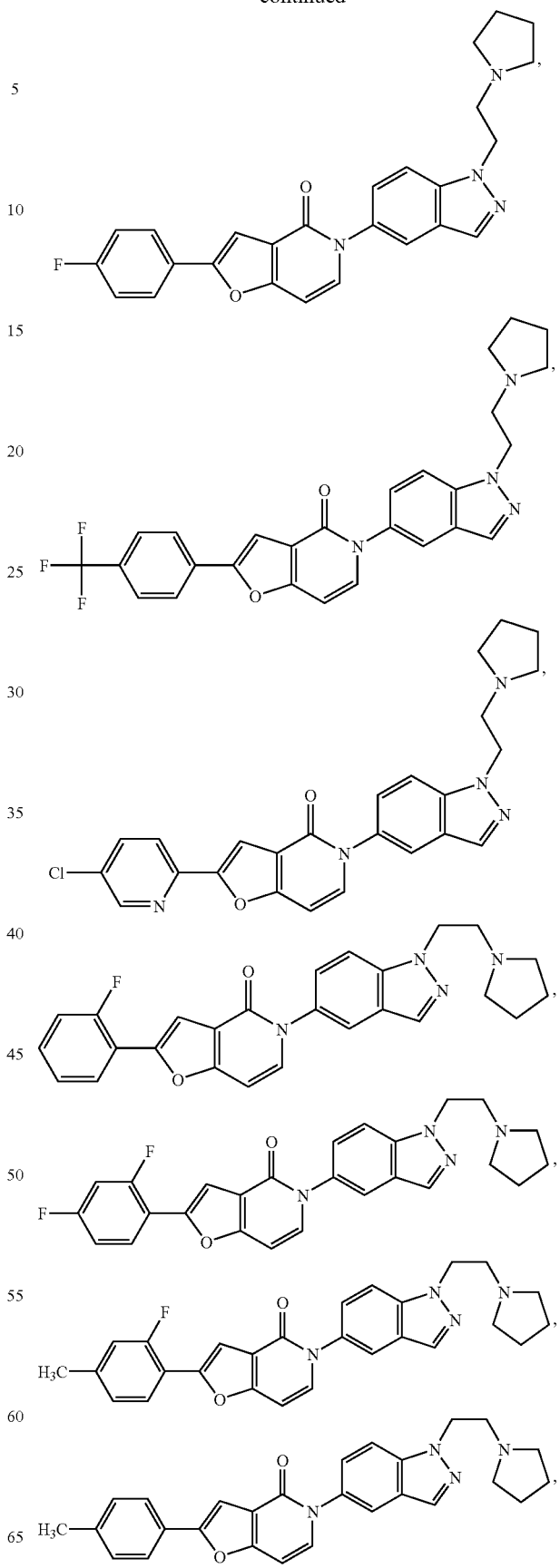

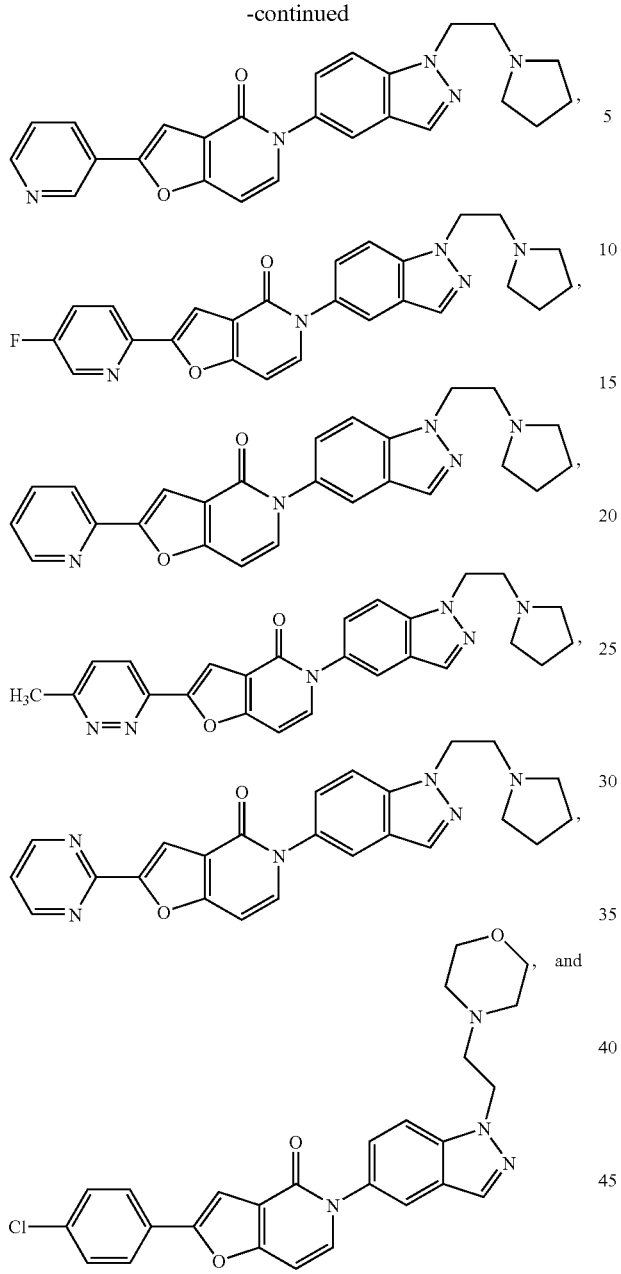

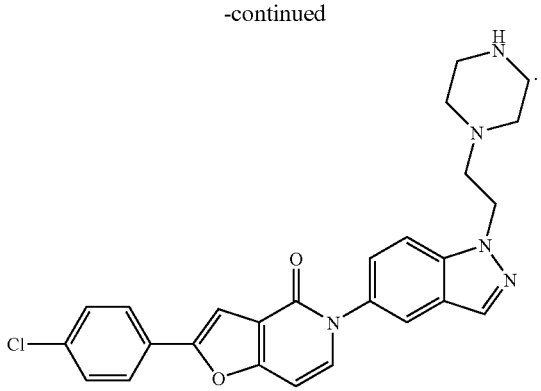

18. A compound according to claim 1 which is in pharmaceutically acceptable salt form.

19. A compound according to claim 18 which is the HCl salt form.

20. A pharmaceutical composition comprising a compound according to claim 1 and a pharmaceutically acceptable carrier, excipient or diluent therefore.

21. A method of treating obesity, comprising administering to a patient in need of obesity reduction an obesity-reducing effective amount of a compound according to claim 1, wherein treating does not include prevention.

22. A method of treating anxiety, comprising administering to a patient in need of such treatment a therapeutically effective amount of a compound according to claim 1, wherein treating does not include prevention.

23. A method of treating depression, comprising administering to a patient in need of such treatment a therapeutically effective amount of a compound according to claim 1, wherein treating does not include prevention.

24. A method of treating non-alcoholic fatty liver disease, comprising administering to a patient in need of such treatment a therapeutically effective amount of a compound according to claim 1, wherein treating does not include prevention.

* * * * *